United States Patent
Shyjan

(12)
(10) Patent No.: US 6,458,939 B1
(45) Date of Patent: Oct. 1, 2002

(54) COMPOSITIONS AND METHODS FOR THE DIAGNOSIS, PREVENTION, AND TREATMENT OF NEOPLASTIC CELL GROWTH AND PROLIFERATION

(75) Inventor: Andrew W. Shyjan, Nahant, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 08/818,829

(22) Filed: Mar. 14, 1997

Related U.S. Application Data
(60) Provisional application No. 60/013,438, filed on Mar. 15, 1996.

(51) Int. Cl.$^7$ .................. C07H 21/04; C12N 15/63; C12N 15/85
(52) U.S. Cl. ............... 536/23.1; 536/23.5; 536/24.31; 435/435; 435/252.3; 435/320.1; 435/325; 435/91.4; 435/91.1
(58) Field of Search ............... 536/23.1, 23.5, 536/24.31; 435/252.3, 320.1, 325, 91.1, 91.4

(56) References Cited

U.S. PATENT DOCUMENTS
4,835,255 A 5/1989 Weissman et al. .......... 530/350

FOREIGN PATENT DOCUMENTS
WO   WO 94/12881   6/1994
WO   WO 96/00289   1/1996

OTHER PUBLICATIONS

Auffray, C. et al. GenBank. Accession No. 225283, 1995.*
Beale, EG. et al. JBC. 260 : 10748–10760, 1985.*
Liang, P. et al. Cancer Res. 52(24): 6966–6968, 1992.*
Hillier. et al. Accession No. AA 196 387, 1995.*
MP Search, Accession No. E03314.
Alonso et al., "cDNA cloning and sequence of MAL, a hydrophobic protein associated with human T–cell differentiation", Proc. Natl. Acad. Sci. USA 84:1997–2001, 1987.
Boring et al., "Cancer Statistics, 1993", CA–A Cancer Journal For Clinicians 43:7–26, 1993.
Donalies et al., "Expression of M–cadherin, a member of the cadherin multigene family, correlates with differentiation of skeletal muscle cells", Proc. Natl. Acad. Sci USA 88:8024–8028, 1991.
Gross et al., "cDNA sequence coding for a translationally controlled human tumor protein", Nucleic Acids Research 17:8367, 1989.
Hoffman, "Orthotopic Is Orthodox: Why Are Orthotopic—Transplant Metastatic Models Different From All Other Models?", Journal of Cellular Biochemistry 56:1–3, 1994.
Hunter, "Cooperation between Oncogenes", Cell 64:249–260, 1991.
Land, "Cellular Oncogenes and Multistep Carcinogenesis", Science 222:771–778, 1983.
Pallanck et al., "Cloning and characterization of human and mouse homologs of the Drosophila calcium–activated potassium channel gene, slowpoke", Human Molecular Genetics 3:1239–1243, 1994.
Robishaw et al., "Existence of Two Y Subunits of the G Proteins in Brain", The Journal of Biological Chemistry 264:15758–15761, 1989.
Ruley, "A denovirus early region 1A enables viral and cellular transforming genes to transform primary cells in culture", Nature 304:602–606, 1983.
Sano et al., "Protocadherins: a Large family of cadherin–related molecules in central nervous system", The EMBO Journal 12:2249–2256, 1993.
Togo et al., "Host Organ Specifically Determines Cancer Progression", Cancer Research 55:681–684, 1995.
Vogelstein et al., "Alletotype of Colorectal Carcinomas", Science 244:207–211, 1989.
Vogelstein et al., "The multistep nature of cancer", Trends in Genetics 9:138–141, 1993.
Wang et al., "Matrix Metalloproteinase Inhibitor BB–94 (Batimastat) Inhibits Human Colon Tumor Growth and Spread in a Patient–Like Orthotopic Model in Nude Mice", Cancer Research 54:4726–4728, 1994.
Seaver, Monoclonal Antibodies in Industry: More Difficult Than Originally Thought, Genetics Engineering News, Aug., 1994, vol. 14, No. 14, pp. 10 and 14.

* cited by examiner

*Primary Examiner*—Geetha P. Bansal
(74) *Attorney, Agent, or Firm*—Fish & Richardson, P.C.

(57) ABSTRACT

The present invention relates to methods and compositions for the diagnosis, prevention, and treatment of tumors and cancers (e.g., colon cancer) in mammals, e.g., humans. The invention is based on the discovery of genes that ate differentially expressed in tumor cells relative to normal cells. The genes identified can be used diagnostically or as targets for therapy, and can be used to identify compounds useful in the diagnosis, prevention, and therapy of tumors and cancers.

27 Claims, 13 Drawing Sheets

FIG. 1a (SEQ ID NO: 1)

rohc029

AGGTGACCGTGGGGCATGAGGTGACTGGGGAAGGGAGACCTCTCCTGGCAGC
ATTTCTAGGACCCAACAAGATCTGGAGGTGCCGGCTCTGGTTCCATCTCTAATC
CCCTGCTGTGGCCTGGCCAGTGTACTGCCCGGAGCTGGAAACCAATAAACCTG
TGATTTGCCCCC

FIG. 1b (SEQ ID NO: 2)

rohc030

AGGTGACCGTGACCTGAGAAGGAAAGAAAGATCCTCTGCTGACCCCTGGAGC
AGCTCTCGAGAACTACCTGTTGGTATTGTCCACAAGCTCTCCCGAGCGCCCCAT
CTTGTGCCATGTTTTAAGTCTTCATGGATGTTCTGCATGTCATGGGGACTAAA
ACTCACCCAACAGATCTTTCCAGAGGTCCATGGTGGAAGACGATAACCCTGTG
AAATACTTTATAAAATGTCTTAATGTCCAAAAAAAAAAA

FIG. 1c (SEQ ID NO: 3)

rohc036

TTTTTTTTTTTTGGCGAGGTGGGAATGCCCACAGGCACTGGGGATGCACTGAC
TGGTGAGGAGGCCTCTGCAAAGAAGGAAGGAGGAGAGGTATAGGCTGGTACC
GAGTACACTGACGAAGCCTGCACATTCGTAGGTGAGGCAGCATTCACTGGCCG
GGGAGGAAGAGCTTGCTTCATGGCCAGGGCTGAATTGACCTTGACTGATGACT
TCTGGGGGAGGCCATCCTTTGCATCTGGAGGTTGGAAAGTAAACAAGGATGC
ATTGAGCTGATACGGTTGGTGCTTCATGACATCTAATGCATTGAGGGGTTTCT
TTCCCTTTTTTTGCCCATTTTGGAGGGCTGTGCAGCTGATGGCTGAGAYYTKG
MRAGCAGCCAGTGGGTAAGACGGCGATTGAAG

FIG. 1d (SEQ ID NO: 4)

rohc038, rohc102

TTTTTTTTTTTGGGAAGGGAGAAAAAGATTGCTTTGGTCTTTATTTTCTCAACT
CATGAAAAACTAAAAACACTATTATTTTCCCTTAGAATTTTGATTTGGAACA
TCTCTACAAATGCTGAAGCTTTGTCATTTTATGTGTGTTTCTGAAGTAATATG
GTTTTAACAGAGTTTATCAAACATTAGCATAGCTTCATCAATTTTTCCTAGGA
GAACTCCCTGGATATCAGGAACAGTGTGTTGTGTTGTGTATGTGGTGTG
TGTATGTGAAGGGCCTG

FIG. 1e (SEQ ID NO: 5)

rohc048

GGAGTGCCTCAGTAAGATACAAATGAGTTGAATTGCCTTATCTGGACTTAATT
CATGTATGTTTGGTTCTTGAGGTACACGCTTACTGGAAGAGGTCCCCCAACCC
ATCTTCCCTTTTAAAACTGGTGTTTGGAAACATCAAACACTACTAATAAACTC
GAAACAACAACCTACCCCCCCACCCCAAAAAAAAAAAAA

FIG. 1f (SEQ ID NO: 6)

rohc056

GGCTAACCGAGAGAGCCGTATATTAATTAATCCTGGAAACCATCTTAAGATC
CAAGAAGGTACTTTAGGATTTTTCATCGCAAGTGATGCCAAAGAAGTTAAAA
GGGCATTTTTTTACTGCAAGGCCTGTCATGATGACATCACAGATCCCAAAAGA
ATAAAAAAATGTGGCTGCAAACGGCTCAAGGTTGCAGCTAGATCACGCTATT
CCAAAGATCCATTTGAGTTCAAGAAGGAGACTCCCAATTCTCGGCTTGTGACC
GAGCCAGTTGAAGATGAGCAGCCGTCAACACTATCACCAAAAAAAAAAA

FIG. 1g (SEQ ID NO: 7)

rohc075

GGNNATCAGATGTCTGGTAACTGCTGCTTCTTGTTACTATGATTATTTGATGG
AGGCCAGTATTTCATTTAATTGCTAANTCTGTCATAGTTTTATACTAGTAGCC
ACTAAGGTAGGTAGTAATAGATTATCTCCTTAATGAAAATCCCTTTTATKAA
ATGCGTAACAAGCTGTAATACAGGGCCTAGTGTGTCATACATNATNTTGGCT
GCCCGNTAAATTCACAATCTAGG

FIG. 1h (SEQ ID NO: 8)

rohc082

TTGGCACGGGGACCATTTACTCCACAATGTCTTTTGACCGGGAACATCAGACC
ACATACACTTTCAGAGTCAAGGCTGTAGATGGGGGAGATCCTCCCAGATCTGC
CACAGCTACAGTCTCGCTTTTTGTGATGGATGAAAATGACAATGCTCCCACAG
TTACCCTTCCC

FIG. 1i (SEQ ID NO: 9)

rohc083

TTCTTCCCCAAGCACCACATCACAGCAGGCAAACTCTCAGTCAACTCCTGAGC
CTTCACCATCACAGACATTTCCCGAGTCTGTGGTAGCCGAGAAGCAGTATTTT
ATTGAAAAATTAACGGCGACAATCTGGAAGAACCTTTCTAATCCAGAAATG
ACTTCTGGATCTGATAAAATTAATTATACATATATGTTAACTCGTTGTATTCA
GGCGTGTAAGACAAATCCTGAGTATATATGCTCCTTTAAAGAAAATTCCT
CCTGCCGACATCCCCAAAAAAAAAAAGGCCGATTTCCSGVACACTGGGGGC
CGTTAATNGTGG

FIG. 1j (SEQ ID NO: 10)

rohc090

AGCTTAGGGATGTTCTGCACTAAGGATTTAGCCAAGTGAGGATTAGCCCAGA
GTGGCACAATGGGCTGCCAGCCGCCTTGTGAGCACGAGATCTAGGCAGTCCCT
GCGCAGACTGGTTAGGAGAGGAAATAGATGGCTCTTCCCTAGGGCCTCGTCTG
TGTTTCTCTCAATGAGTTGAGGCCTGAAAGAGGCCACACTGGGACTCCCACTT
GTGGCCCAGGCTAGAGAAGGCCTGGTCTGGAGAGAAGTCACAATTTTGAGAG
TCATATATAGTTTCTTCTGCAAAATGAGAGCTTATGAAAGGTTTATTCACAA
ATAGTGTATGGAATAGAACTACCCTGGCNCAATCCTGTTACTGAGCATCTGCC
CAAAAAAAAAAAAA

FIG. 1k (SEQ ID NO: 11)

rohc092

TTTCTCCGCTTGAATATCTAATGGGCGTCTCAAACTTAATATGGCTAGGATAA
TTTTTTAATTTCTAACCCCTATGCTCACAAATCTCCTTGCAAGTCTTCCCTATC
AGTAAATGACATTAATGTCTCAGGCTTGGGGATTAGACCCAAGTACTCCATG
GCTCCAGGAGAGAGTCTAAGCAGCATACTTGATTCTTTCCTTCTTCTTACCACC
CTCCGCCTAATTCCTAGATGAATCCTCTTGGCTACCACCTTAGTTCATCATGTC
TGATTGGGCTGTTATAGTCGCCTTCTAATTTCCTCCCTGCCAAAAAA

FIG. 1l (SEQ ID NO: 12)

rohc093

CGGCTTAAGCCCGAGGGAAGGAGGAGTTTCTTCAAATGGGAATAATAGCATG
ACCAAAGATTTGGACTTGACACTGAATGTTTATGTGAGGGTTATATTGGAAT
CAACTTGACCTGAATGGAATTGTGAACAAGTCATGGAGATAAATGTGGTGT
TTACAAGTGGAACAGAGTTGTTCTTTTGAAAGGCAACAAGCTATCATCAGAA
AGGTACCATATTGGGAGTTGGCATGGAAATATGTGATCTTAATTAAGTCATT
TATTTTCTCCAGCTCTGTTTTCTCATCCAAAAAAAAAA

FIG. 1m (SEQ ID NO: 13)

rohc095

CTTACACAGAGGGGACAAGGTGGAGATGTTACCAGACACCACAGGCAAGGG
AGCCCTCATGTTTGTCAAGAGGAGGGAGAGAATGGATCAGATCACAGCCCAA
AAAAAAAAAAA

FIG. 1n (SEQ ID NO: 14)

rohc096, rohc105

TGTCTACGGCATTTGAAGAGAGCGAGGAGAACCATTCTGGAAACTCTAGGCT
ATGCATGTTTAAAGATCTGGTCCCCTTTATGAGAATGCAAGCCGATCCACATC
CTGACTTAAGAGATCTGATTCTGACGAACTGCCTGGAGGAGGGGAATATATA
AAAATAAAATTGGTGTCACTTCTTTTCTGCTATCCCCCAGCCCCCCCCCAAAA
AAAAAAAA

FIG. 1o (SEQ ID NO: 15)

rohc097

GGCTTGGACGACAAGCAGAAGCCAGTTATGATGACAGGTGATAGATCCAAA
ATAATTGCCACATTTGTTAACATTTTTCCATTTCTAAACCATCCTTAAAGAAA
ATCATATATGGGGTCACACCATCCTCACGGTAGTCCAATAGAGCAACCATGCC
ATCTGGATTCATGTTTTCACCAATAAAGAACTGGTAGTTTTTGAAATTAGCA
AGGATGTGCTTGATTTGTTCTGCAGCCCTGTCATAAAAGGTTTTACTCTTTCT
GGTCTCTGTTCTTCAAGTTTCCCTTTGATTGATTTCATGTAATCTTTGATGTACT
TCTTGTCGTCCAAGC

FIG. 1p (SEQ ID NO: 16)

rohc101

GCTTTTCCCCCCAGCACCTAGAAATGAGACAGAATAAATGCTCAATAAGCGA
CCATCTACAAACAGACAAAATAAATGCCCAATAAATGCTCACTGGATAAAG
GAATCAAATCCTGAGGGTGCACAACATTTCCCAAGCAAGTGGCAAGAAGAGT
CCAGAGCCGTCTCGCTCCCGATGCTGGCAGCTCTGTGTCCTCTCCTGCTTCTCTCT
ATGTGTTCCCTCGTTCATACTCTGTTCTCATCTGCATCTTTTCCGTTTCTCCACTT
TCAACAGCTTCCCCACCCCAACCCATCCCCAAAAAAAAAAAA fohc082

```
  P   S   I   E   I   R   K   I   G   R   I   P   L   K   D   G   V   A   N   V    20
CCG TCC ATT GAA ATC CGC AAG ATT GGG CGC ATC CCC CTC AAG GAC GGG GTG GCC AAC GTG    60

A   E   D   V   L   V   D   T   P   I   A   L   V   Q   V   S   D   R   D   Q    40
GCC GAG GAC GTT CTG GTC GAC ACC CCC ATC GCT CTG GTG CAG GTG TCC GAC CGA GAC CAA   120

G   E   N   G   V   V   T   C   T   V   V   G   D   V   P   F   Q   L   K   P    60
GGC GAG AAC GGG GTG GTC ACC TGC ACC GTG GTG GGC GAC GTG CCC TTC CAG CTC AAG CCA   180

A   S   D   T   E   G   D   Q   N   K   K   K   Y   F   L   H   T   S   T   P    80
GCC AGC GAC ACC GAG GGC GAC CAG AAC AAG AAA AAG TAC TTC TTG CAC ACC TCG ACC CCT   240

L   D   Y   E   A   T   R   E   F   N   V   V   I   V   A   V   D   S   G   S   100
CTG GAC TAT GAG GCC ACC CGG GAG TTC AAC GTG GTC ATC GTG GCG GTG GAC TCA GGC AGC   300

P   S   L   S   S   N   N   S   L   I   V   K   V   G   D   T   N   D   N   P   120
CCC AGC CTC TCG AGC AAC AAC TCC CTG ATT GTC AAG GTG GGA GAC ACC AAC GAC AAC CCG   360

P   M   F   G   Q   S   V   V   E   V   Y   F   P   E   N   N   I   P   G   E   140
CCC ATG TTC GGC CAG TCG GTG GTG GAG GTT TAC TTC CCT GAG AAC AAC ATC CCG GGC GAG   420

R   V   A   T   V   L   A   T   D   A   D   S   G   K   N   A   E   I   A   Y   160
AGG GTG GCC ACG GTG CTG GCG ACA GAC GCA GAC AGC GGT AAG AAC GCC GAG ATC GCC TAC   480

S   L   D   S   S   V   M   G   I   F   A   I   D   P   D   S   G   D   I   L   180
TCG CTG GAC TCC TCT GTG ATG GGG ATC TTT GCC ATC GAT CCC GAT TCT GGG GAC ATC CTG   540

V   N   T   V   L   D   R   E   Q   T   D   R   Y   E   F   K   V   N   A   K   200
GTC AAT ACC GTG CTG GAC CGC GAG CAG ACT GAC AGG TAT GAG TTT AAA GTT AAC GCC AAA   600

D   K   G   I   P   V   L   Q   G   S   T   T   V   I   V   Q   V   A   D   K   220
GAC AAA GGC ATC CCC GTG CTG CAG GGC AGC ACT ACG GTG ATT GTG CAG GTG GCT GAT AAA   660

N   D   N   D   P   K   F   M   Q   D   V   F   T   F   Y   V   K   E   N   L   240
AAT GAC AAT GAC CCT AAG TTT ATG CAG GAC GTC TTC ACC TTT TAT GTG AAA GAA AAC TTG   720

Q   P   N   S   P   V   G   M   V   T   V   M   D   A   D   K   G   R   N   A   260
CAG CCC AAC AGC CCT GTG GGG ATG GTC ACC GTG ATG GAT GCT GAC AAG GGG CGG AAT GCA   780

E   M   S   L   Y   I   E   E   N   N   N   I   F   S   I   E   N   D   T   G   280
GAG ATG AGC CTG TAC ATA GAG GAG AAC AAT AAC ATT TTT TCT ATT GAA AAT GAC ACG GGG   840

T   I   Y   S   T   M   S   F   D   R   E   H   Q   T   T   Y   T   F   R   V   300
ACC ATT TAC TCC ACA ATG TCT TTT GAC CGG GAA CAT CAG ACC ACA TAC ACT TTC AGA GTC   900

K   A   V   D   G   G   D   P   P   R   S   A   T   A   T   V   S   L   F   V   320
AAG GCT GTG GAT GGG GGA GAT CCT CCC AGA TCT GCC ACA GCT ACA GTC TCG CTT TTT GTG   960

M   D   E   N   D   N   A   P   T   V   T   L   P   K   N   I   S   Y   T   L   340
ATG GAT GAA AAT GAC AAT GCT CCC ACA GTT ACC CTT CCC AAA AAC ATT TCC TAC ACT TTA  1020

L   P   P   S   S   N   V   R   T   V   V   A   T   V   L   A   T   D   S   D   360
CTG CCA CCT TCG AGT AAT GTC AGG ACA GTA GTA GCT ACA GTG TTG GCA ACA GAC AGT GAT  1080

D   G   I   N   A   D   L   N   Y   S   I   V   G   G   N   P   F   K   L   F   380
GAT GGC ATC AAT GCA GAC CTG AAC TAC AGC ATT GTG GGA GGA AAT CCC TTC AAG CTG TTT  1140

E   I   D   P   T   S   G   V   V   S   L   V   G   K   L   T   Q   K   H   Y   400
GAA ATT GAT CCC ACT AGT GGT GTG GTT TCC TTA GTG GGA AAA CTC ACC CAA AAG CAT TAT  1200

G   L   H   R   L   V   V   Q   V   N   D   S   G   Q   P   S   Q   S   T   T   420
GGC TTG CAC AGG TTG GTG GTG CAA GTG AAT GAC AGT GGG CAG CCT TCC CAG TCC ACC ACG  1260
```

FIG. 2a foh-c082

```
  T   L   V   H   V   F   V   N   E   S   V   S   N   A   T   A   I   D   S   Q    440
 ACT CTG GTG CAC GTG TTT GTC AAT GAA AGT GTT TCT AAT GCA ACT GCG ATT GAC TCC CAG   1320

I   A   R   S   L   H   I   P   L   T   Q   D   I   A   G   D   P   S   Y   E    460
 ATA GCT AGA AGT TTG CAC ATC CCA CTC ACC CAG GAT ATA GCT GGT GAC CCA AGC TAT GAA   1380

I   S   K   Q   R   L   S   I   V   I   G   V   V   A   G   I   M   T   V   I    480
 ATT AGC AAA CAG AGA CTC AGT ATT GTC ATT GGC GTG GTT GCT GGC ATT ATG ACG GTG ATT   1440

L   I   I   L   I   V   V   M   A   R   Y   C   R   S   K   N   K   N   G   Y    500
 CTA ATC ATC TTA ATT GTA GTG ATG GCA AGG TAC TGC AGG TCC AAA AAT AAA AAT GGC TAT   1500

E   A   G   K   K   D   H   E   D   F   F   T   P   Q   Q   H   D   K   S   K    520
 GAA GCC GGC AAA AAA GAT CAC GAA GAC TTT TTT ACA CCC CAA CAG CAT GAC AAA TCT AAA   1560

K   P   K   K   D   K   K   N   K   K   S   K   Q   P   L   Y   S   S   I   V    540
 AAG CCT AAA AAG GAC AAG AAA AAC AAA AAA TCT AAG CAG CCT CTC TAC AGC AGC ATT GTC   1620

T   V   E   A   S   K   P   N   G   Q   R   Y   D   S   V   N   E   K   L   S    560
 ACT GTG GAG GCT TCT AAG CCA AAT GGA CAG AGG TAT GAT AGT GTC AAT GAG AAG CTG TCA   1680

D   S   P   S   M   G   R   Y   R   S   V   N   G   G   P   G   S   P   D   L    580
 GAC AGC CCA AGC ATG GGG CGA TAC AGG TCC GTT AAT GGT GGG CCC GGC AGT CCT GAC CTG   1740

A   R   H   Y   K   S   S   S   P   L   P   T   V   Q   L   H   P   Q   S   P    600
 GCA AGG CAT TAC AAA TCT AGT TCC CCA TTG CCT ACT GTT CAG CTT CAT CCC CAG TCA CCA   1800

T   A   G   K   K   H   Q   A   V   Q   D   L   P   P   A   N   T   F   V   G    620
 ACT GCA GGA AAA AAA CAC CAG GCC GTA CAA GAT CTA CCA CCA GCC AAC ACA TTT GTG GGA   1860

A   G   D   N   I   S   I   G   S   D   H   C   S   E   Y   S   C   Q   T   N    640
 GCA GGA GAC AAC ATT TCA ATT GGA TCA GAT CAC TGC TCT GAG TAC AGC TGT CAA ACC AAT   1920

N   K   Y   S   K   Q   P   F   R   R   V   T   F   S   V   V   S   Q   P   Q    660
 AAC AAG TAC AGC AAA CAG CCA TTT CGT AGA GTG ACG TTT TCT GTT GTG AGT CAG CCT CAG   1980

D   P   H   Q   G   S   L   Q   S   C   Y   D   S   G   L   E   E   S   E   T    680
 GAC CCA CAT CAG GGG TCA CTG CAG AGT TGC TAT GAC AGC GGG CTG GAG GAG TCA GAA ACA   2040

P   S   S   K   S   S   S   G   P   R   L   G   A   L   P   L   P   E   D   N    700
 CCA AGC AGT AAG AGT TCA TCA GGG CCA AGA CTG GGT GCG CTT CCA CTC CCA GAG GAC AAC   2100

Y   E   R   T   T   P   D   G   S   V   G   E   A   E   H   M   E   N   G   V    720
 TAT GAA AGG ACC ACG CCG GAT GGC AGT GTT GGT GAG GCA GAG CAT ATG GAA AAT GGT GTT   2160

A   A   I   T   T   F   P   F   L   P   F   P   H   G   K   T   H   G   R   R    740
 GCT GCC ATC ACT ACC TTT CCC TTC CTC CCC TTT CCT CAT GGC AAG ACG CAT GGA AGA AGA   2220

V   L   L   R   P   L   H   *                                                    747
 GTG CTG TTA AGG CCT CTC CAT TAA    (SEQ ID NO:18)                                  2241
```

TCAACAGATTCAAGGCCTCTTCCAGATGTAGCCCTGACTGGGAAGTGCACTCGTGAGTGTGATGAGTATGGCCACTCAGA

CTCCTGCTGGATGCCGGTCCGCACTTCTCCGGAGAGGAAGAAGAGCCAGCCTAAACTGTCCACTTNCATGCCTGTTGATG

AACGAGGAAGCCAGGAAAAGCTGGCCAATGGGAGGCCGCCATCATGGGTGACCGCAACAGAAACCTCCTGAACAAAAAG

TTGACCTCATCCTATGAGACCTTCAGTGCAGCTAGTTTCAGCAAAAATGAGGAAGCCAACCCTGAGGATATTCCCCTTAC

AAAAACAGGGGAATATAAGCCATCTCCTGTCAATACTCTCACTAGAAGAGAAGTTTACCTGTAGGTTATAAAGGAGCAAC

AGCAAAGTTCTTTACATGTATGAAAAGGAGAATAAGGGGCAAAAACCTTACAAAGCAAAACGTTTAATCACAAAGAGGGG

GCTACCAAAGAGACAAAGCTTTGCCTGCCACTTCTGCCTCCAGATCAGGCCTTTAGTGATACTGTTAGCCTGATTCTACT

FIG. 2b fohc082

GTACAATGTAGAAACCATCCTTGTTACTTGCATGTCTAACCCCTTCACTGATTCCCAACACTCACTTTCTCTTCCCCACC
CCTCTCCMMAAAAAAAAAAAAAAAAAAGAAAAGAAAAAAAAAAGGGGGATAGTTGCAAGTTTCTTTCACAGTAACTGTACG
AAGCCTGATTAGCAGAACACAACACACCCTCATTATCCCTAAGCTGAAGCATGATTTTAGTCACTTTGATTTTGTTCGAG
TGTCATCTGGCTGGTCAAAAATAAGCAGGACAGATAAAATGTATTTCAGACATACCATCAGAAAATGGTTTATCACCATC
AAAGGCAATCCTTTGAAAGTGATAGAGTCCCTCTAAAGGTACAGTCCTTAGAAAGAGGGACTGTATTAAAAAGTATGGTG
GGAATATCAAAGCTTTAATATTCCAACAAAGACTAAGAGAAAAACAATACTCAGTGGGTGATTGCAGTCCTAAATTGTCA
TATGTTGTTATTTTCAGGTCAAGAGCATCAACTTCAATTCCATACATTCACCAAATATTCTCAGTATACACACAGTCTTG
ATTACATGTATCAATTTCACCAGTTATGACTTCTAAAAATTATATATATTTTTTCAGAACAAGACCACTATTATTAACTA
ACTTGAACAATTGTATCATCCAAAGGCCAAAGATCATATGGCAGATCAGGGAAGTCATGAAGTTGATTTGGTCTTGACGT
GGAAAACCATTAAACAACAAAAGCAACTGAACCCATGTATGCACAGAAACAATCAAACACTAGTTCATTTTATAGTGCCC
AGGAAAATGTTCCTTCTTTTAAAATGGATTTTATTTGAAAGCGCAGAAAATGAAAACTAGTGAGATATATTTTTGGTATT
ATAATAGGCAATTGGTTGAGGTTCAAGTTTAGTTTCAGGTAATATTATCAGGGAAGATTCCATGTTTTAAAATAGTATTT
ATGGATCATGGGTAGGTTAAGAAAGATGCATTGGCATATAGTCTTGATAGTTAAGTCCACGATTATCATTTTAGAATCCA
GGCTATGCTTGCTGCTCTTTTTATCCACATTTTAAATTACAATTGCATTTTTTACTTGTTCAGTGCACACTTTGATGCAC
CACAAGTGCATTAATTTTGAATCGTGTGCAATATAGAAATATTTTGAGACTCACAACATTGAAACAAGGTGACACCCTAG
TTGACTTTATCACTAATGTGATTTGAACATTATTTAAACAAATCTAGACTGAACATGAAAGAAAGGAGTTTTGGGCAGTG
ACATTTTTCACAGAATGTATATCTCAAAGGTGAAAGCAGAGTTTTTCCAGTGCAATAAAAAGAAACAGAATATGCAGATT
TTGAGCTACTCGCTCTATAGAGGATAACCTAACACGGCTGAAAATTGAGCTGGGACATTCAGACGAAAGTGACAATCCAT
GGACAGAATAGGGAATAACAGGTGTGAAGAGAACAAACTTATCACTGAATGTTTGCAAGCTGGTTAAGGCATAGCCTTGA
TGGCTCTCTAGCAAACTGTAGAAACAATGTAGCTTTGGGTAGTTTCATGCTTTGCAGAATTTCTTAGACTATAAAGTGAC
ACAGCCTGGAATATAGGTTGATAATTCACTATAGGTCTTCNAAATACTTATCTTTGAAAACCGCTTCTCTGTNTGGTGGG
GTACAATTTGGGGGTCATTTCCTTATGCTCTTTCTTAAATGGAGTTTTCATTTTGATGTTAGTTTATGTATAATAGGTAG
GATGCAAAAAGATATGTAATTGAAACAAAAAACATTGGACTAAAATATCAGTAATTGAACATGTTTATGTTTGATTATTA
TTTACACTATGGAAAGATGCAATTCTAGTACTTTGTTAGGAAACTGCATTAAAGCAGTTCTGCCTTGTATAATCTGTAAG
TACCTATTAAGACAAAATACTTCTAAAGATACTTATGAAATGTATACATATTTTTTCTTGCACGTTACAAAGAAAATACT
CAATTGCATAACACGGATGTTTGACAAACTTTTTTTTTTTAATGCATTTCTTTCTTTCATGAGACATTGAAACCACTGAT
AGCTCATTTCACCCTATCTTAAACCCTTCTCTTGTCTATAAAACTAATACGGGTCACACCGGACCTTCGGATTAATTGGAT
CCACATT (SEQ ID NO:17)

FIG. 2c fohc048

GGCTTCTTTCCCAGTAAGCGTGTACCTCAAGAACCAAACATACATGAATT
AAGTCCAGATAAGGCAATTCAACTCATTTGTATCTTACTGGAGGCA:CAT
CCAAGCAAGGAAGAATAGAGACTTAGTTATATTAGGCTCTCTCCCAGCTC
TGAGATGAGTATATTCTTTGGGGGGCTTGCTAATGTTGCAAGTTTGCATT
CAAAATAAATTCTAGGCACTCACATAATCCCCCAGTCTCCTCCAAACTTT
CTTTGATGTCCAACAACTAAGGACAAGGATCTTTGATTATAAAACAATTT
CTTTGGTTGGAAGAAAATTCTTTGCAGGGCGTGAACAGCCGGAGAAAGAA
AAGGTTTTTCTGAAGTGCAAACTAGTTGGAAACCCCTGGGGAAAGAATC
TGATTCCCAGTCTTTGAGAGGACCAGGCCTGCCTGTACAAGTTGCCTCTG
CTGAAGGCCTCTAAGAAGGCGCTTTTGNGTCTACTGTATGGCCCTCAGCA
ACAGCACGGCRGCCCTTCTCTTTTTTTTTGGCAGCGGAAGTTTTCCATCT
CTGGGAATACACAATGCAGAAAGTCACGGTTTAATAACAAGGCATAGTTA
CTAATCAGATGGCCCCATTTCCACTCTTCCCAGTTGCCTCCAGATGCTTA
CATACTAGAGCTCTATCCCCCTCACCCCATGGGTGAACACCCACCAGCTG
CTCTGAAATCTTATTTTAGTATAAGTATTCAGCTTATCTCTAATAATTC
ACTTCACAGAGTACTTAGGATCAGAAGCATCCTACTCCTTTTACTTTCAT
CCAGACTGGTTCTAGGTTGTCTCTGGCTCTTTCAGGTTTTTCCAAAGGTT
AGATTCACTTAGGTGCAGGACCTGCCCGGGCGGCCGCTCGAGCCCTATAG
TGAGTAAGCC
(SEQ ID NO:19)

FIG. 3 fohc090

TTACTCACTATAGGGCTCGAGCGGCCGCCCGGGCAGGTCACACACATAAA
ATTAGCTGGCATGGTGTTATGTGCCTGTAGTCCCAGCTACTCAGGAGGCT
GAGAGGCAGAAGGATTGCTTGAGCCCAGGAGTTCGAGGCTACAGTGAGCT
ATGATCATGCTACTGCACTCCAGCCTGGGTGGCAGAGAGAGACCTTGTCT
CTCTAAAAAATAAAAAATAATAAATTTCTTTACAAAATTTGTGATCAAGT
CAGGGCTTATTTCACTTAAGATGAAGACCTCTGGTTATACTACCAT:GTT
GCTGCAAAAGACAGGATTTCATTATTTTTTGTGGCTGAATAATATTCCAT
TGCATATATATACATTTTCTTTATCCATTCATCCATTGATGGACACTTAG
ATTGATT:CCATATCTTTGCTATTGTCAATAATACTGTAATAAAAATATA
AGTGCAAGTATGTCTTTGATACTAATATATTGATTTCTTTTCCTTTGGGC
AGATGCTCAGTAACAGGACTGTGCAGGGTAGTTCTATTCCATACACTATT
TGTGAATAAACCTTTCATAAGCTCTCATTTTGCAGAAGAAACTATATATG
ACTCTCAAAATTGTGACTTCTCTCCAGACCAGGCCTTCCCTAGCCTGGGC
CACAAGTGGGAGTCCCAGTGTGGCCTCTTTCAGGCCTCAACTCATTGAGA
GAAACACAGACGAGGCCCTAGGGAAGAGCCATCTATTTCCTCTCCTAACC
AGTGCTGCGCAGGGACTGCCTAGATCTCGTGCTCACAAGGCGGCTGGCAG
CCCATTGTGCCACTCTGGGCTAATCCTCACTTGGCTAAATCCTTAGTGCA
GAACATCCCTAAGCTGACCACATCTCTGCAAAACCTGAGACATACCCAGG
CCTGGTCTGCTAAGATGGAATCTGTGAAGTTTGCCCAGATGGTCAGATCA
AATGTCTGGCTGAATTCCCACTGTGCTAGCTTTATCTCATTCCTGTCATC
TTCCACACTGGTAACTGGATCAAATAAGCTTTTACTGGCAGGACAAATCA
ACGGATAAAGGAAAGACTGTTCCATGAAGCTGTCCTGGGATAGCAAGTTA
GTAAATTGAAGGGAAAAGTGTGTTAGAGTTTCTTCTTGCACTATGAACTG
AAGTAAATTTGAGACAGGTCAAAGAACTTAAAAATCAATCCACGGAACCT
CTAGAAGACTCTAGAATTGTACATTAAAAAATAAATCAATATGTAAATGA
TCAACACATTGAACTGCATGAAAATATTTTACATATTTTTCAAAATAACT
GAAAGGGAAGAATGGGAGAGAAAACTTCAAATATGTAATGAGATCAGACC
TACTGATAAGAAAAATATGAATACCCCATCAATAGGTATATGATATGAAT
ACATAATTCCAAAAACTAAAAATAACTAGTAAACAAATACATAGGATGGC
TTTCAACCTCTCCAGTTATCAAAGAAATACAAACCTATTAGCTATGAATT
TTCACCTGTTAAAATGATTTTTTAAGTTATAGTAATATCAAATATCAGTG
TAAATAACACTGTTGTACACAATTAGTGAGACTGTTAATTTGAATAAATC
TTTGGAGGCCATTTTCTTGTTTACTTATACTTCTAGAAATCATTCTATGG
AAATCAGCAAAACTTGGGAAAAACATATAAAACGGTCATTTTAAATGTT
AATAGTAAAAATTTAGAAAAATTTGATGTTATTTTATAGCAATTAAAAAG
ACGAATTTGAAAACTGAAAATGCTTATGAATAAACTTTAAGATGTGTTAC
GTATAAGGTAAAATTCTATCAACGTTATGTAAAAAATATACAGTAATAAC
ACTAGAAAAATATTCATCAAAATTCCTATAGTGTCTATCT
(SEQ ID NO:20)

FIG. 4 fohc093

CTCTGTTCCACTTGTAAACACCACATTTATCTCCCATGACTTGTTCACAA
TTCCATTCAGGTCAAGTTGATTCCAATATAACCCTCACATAAACATTCAG
TGTCAAGTCCAAATCTTTGTTCATGCTATTATTCCCATTTGAAGAAACTC
CTCCTTCCCTCGGGCCTCTGTATTCTACGTTCTTTGAAATCCAGGTCAAG
TGTCACTCCAACCCCTCCAAGATGTATCAAGGCTGTAACTTCAGCCGACC
TAGACAATATCCCTCTACTATAGCATTTGAATTGTACTATACCAATGTGA
GACATGTAATCATATTATTTCATGTTTACTCAACATTTTTGTGTATGGGG
ACTTCACTTCTTGACTAAACTCAACTTCTTAAGTGAGCTGGATCATGTCT
TTTCTATTGTGTTATCCTTCACAGTGAGTATAGCTCTTTGCAAAGTAGGT
ACTTTACCGTTTGTTGAAAATATAAAGAATCTAAAAATAGAATTTGAAAC
AAAATTTTCAATAGGTAATCCAAGAGCCCAGAGAAAATCAAGTCCATAGA
CAAATCAAGCTTAATTTCACAATTAGCTTAAGTTAATTCACTCATTTGAC
AAGTATATAATGAGTGCCTGCACTGAGCTCATTAAAGTGCTAAGCATTAA
ACTGCAATGGTGAGTGAAACAGACACATCCCTGCCAACGTGGAGCTAACA
GTCTAGTTAGAGGAACACACACATATATTAAAAGTTTAACCAGGACTCTA
GAGAACATGAAAAGAAGTGAACAGATTTGGGATACATGATTAAAGGAAAG
GAGTGAGGGCCAGGAAAGAATAAAAAATAACTTGTGAATTTCTGGTACGT
GCAACAGGAAGGATAACCATGCCATTTCCCCTGAGTTGGAGAAAACCAGT
GGAGGACAAGGTTTATGGGGGTATATCAGGAAAACTCAACCTTGGGCATG
CTGAACAATTCCATTAGCAGAACCTATTAGGTAAAAGAAGTTGACCCCAA
ATGGTTTCAAGTTTTTTTTTTTGACCTTTACCCTATTCATTGTCATAA
ACACCCTATACTTCCCCAAAAGTAAAAGCTCTACCAAGTAGGCCTGAGAA
GAGGAAAGCAGAATCAAGGACTCAGACAGCCCAGAATTGGGTAATTAAAC
TAACTGGGTAGGTTAGGGTTCACTGAGGCAAGGAGAATATAAAATAAATC
TTTTCAATCAAAGAAAATAAAATCTGGCCTATTTATTTCTCTTTATCGAG
TGAATCAAAAGCTTGGCTAAATTGAAAACCCTAAAACCCAATCTAAAAAA
GAGGATGGCTCCTGGTGTTTGTATACATCCATGCAAGAGGTAGGCTTGCG
TAGAGGCTCTTAATCTTCACTCCCCCTCTGAGACAYTGTTGGCTGCTGTA
TAATATTGTGGTATAAATGAGGCCAGCGTTCTGGATTAAAATCTCTTCAA
GCCTCTTCATTGATCACAGGGTTGGAAAGAAACATAGAAGTTCAATACCT
CATATAATCAAAAAATCAAAAAACTTTGGAATCAGAAGGAACGTAGGGCT
CACGTCTTCTAAATTCTTTCTTTCCAAGTAAGCATCTCTTGTAAGACATT
ATTTTACAGAGAAGAAAACCAATCAAAGTCTGAAAAGGTAAAATGACTTG
CCTGCCTAAGGTAACACAGCAAATTAGTGACAAAGCTGGGAAAAGAACCA
TGCTCTCTTGCTTCTTGCCACTATACCATACAGTCTGGAGGGAAAAGAGA
AGGGTCTGCCTAGAGAACAGTTCCTTTCGGAAAGTAATTTGAGATCAAGT
TGATGATATCTAGGGATGATAATTTCCATTCTAAGTTTCAATTTGCTAAA
TGAAGCCCCCATAGGTACTTAATCACATGAGTAAAATGACCGAAATGATA
CTTGAAAAATACAAAATTCATAGTAGATGATTTTGTGATATTCAAGATAT
GGGAAATAGAGCAGCTTGTTATAGAAATCTAGGCACAAGCTAATGAGGAT
AGTGACTCTGCAGGTGGCAAGAAAAGATGACTTAACTTAGGGGCACTGTG
CAGGGTGATGGGCGTCTGACTGATGCAGATATAAAAGGAATAAAGA
(SEQ ID NO:21)

FIG. 5 fohc095

```
TTCCTCGCCCCTGTCAAGACTGAAGTTCCCCTAGCTGAGAACCATAGTGG
TCCCGACTGTGCAGCCAGCTTGAAAGAAGAAACAGGCCCGAGCTACCAAA
GGGCTCCCCNAATGCCTGACTCCCAAAGAGGACGCGTGGCAGAANAGCTG
ATCTTAAGGGAGAAGGTAGAAGCGGTACAGCCTGGGCCTGTGGTTGANCT
GCAACTGTCCCTTTCNCAGGAGAGACATANGGGCGCTNGTGNCCCTTTAG
TGGNTCTCCCGGGAGCTGAAAAATCTAAGTCTCCTGACCCANACCCTAAC
TTGTCACNTGACNGGATTGTCCACATNAATTCGATCCCTACTAATGAGAA
AGCAGACCCTTTCCTGAGGTCCAGCAAGATAATCCAGATCTCCAGTGGCA
GAGAGTTGAGAGTGATCCAGGAAAGTGAAGCAGGAGATGCGGGACTGCCC
CGGGTGGAAGTGATCCWCGACTGCTCTGACAGGCAGAAGACAGAAGGGTG
CAGGCTTCAGRCAGGAAAGGAGTGTGTGGATTCTCCAGTGGAAGGAGGGC
AGTCAGAAGCACCTCCTTCTCTGGTATCCTTTGCCGTCTCATCAGAAGGC
ACAGAGCAGGGAGAAGATCCACGCTCGGAAAAAGATCACAGCAGACCTC
ACAAGCACCGAGCGCGGCATGCACGGCTCAGGANGAAGTGAAAGCCTGTC
AGAAAAACAAGTGAAGGAAGCAAAATCTAAATGCAAAAGCATTGCCCTTC
TTCTAACGGATGCTCCCAACCCCAACTCCAAGGGGGTGTTGATGTTTAAG
AAGCGACGTCGGAGGGCCAGGAAATACACCCTAGTTAGCTACGGTACTGG
CGAGCTTGAGCGAGAGGCGGACGAGGAGGAAGAAGGTGACAAGGAGGATA
CATGTGAAGTAGCATTTCTTGGTGCAAGCGAATCAGAGGTGGATGAAGAG
TTATTGTCTGACGTTGACGACAACACACAAGTTGTGAACTTTGACTGGGA
TTCTGGACTGGTGGACATTGAAAAGAAACTGAACAGAGGGGACAAGATGG
AGATGTTACCAGACACCACAGGCAAGGGAGCCCTCATGTTTGTMAAGAGG
AGGGAGAGAATGGATCAGATCACAGCCCAAAAAGAAGAGGACAAGGTAGG
TGGAACGCCAAGCAGAGAACAAGATGCTGCCCAGACCGATGGCCTGAGAA
CCACGACTTCTTACCAAAGAAAGGAGGAAGAGTCGGTAAGAACGCAGAGC
TCTGTGAGCAAAAGCTACATCGAGGTGAGTCATGGTCTTGGCCATGTTCC
CCAACAGAATGGCTTCAGTGGGGCATCTGAGACAGCAAACATCCAGAGGA
TGGTCCCCATGAATAGAACGGCCAAACCCTTCCCAGGGTCTGTGAATCAG
CCAGCTACCCCCTTCTCGCCAACCCGAAACATGACGAGTCCCATTGCTGA
CTTTCCTGCACCTCCACCTTNCTCTGCNGTCNCTCCTCCCCCTGACGCCT
TCTCCAGAGGGGTTTCAAGTCCGATTGCTGGCCCAGCACAGCCCCCTCCA
TGGCCCCAGCCTGCCCCGTGGTCCCAGCCAGCCTTTTACGATTCGTCTGA
GCGAATAGCTTCCCGAGATGAGAGGATCTCAGTGCCAGCAAAAAGAACAG
GAATATTGCAGGAGGCCAAAAGGAGAAGCACGACAAAACCCATGTTTACT
TTTAAAGAGCCCAAAGTAAGCCCAAATCCTGAACTCTTGTCACTCCTTCA
AAATTCAGAAGGCAAACGGGGCACTGGAGCTGGAGGTGATTCCGGACCGG
AAGAAGACTACCTCAGCTTGGGGGCAGAGGCTTGTAATTTCATGCAAAGC
TCCTCTGCCAAACAAAAGACCCCTCCTCCTGTTGCTCCAAAACCTGCAGT
CAAGTCCTCATCCTCCCAACCAGTAACTCCAGTTTCCCCAGTCTGGTCTC
CAGGAGTGGCTCCCACCCAACCTCCTGCCTTCCCCACATCCAACCCATCA
AAGGGCACCGTTGTCTCCTCCATCAAAATAGCCCAGCCTTCTTACCCTCC
TGCCCGGCCTGCAAGTACTTTGAACGTGGCTGGTCCCTTCAAAGGACCAC
AAGCAGCAGTAGCCAGTCAGAATTACACACCCAAACCAACAGTTTCCACA
CCAACAGTCAATGCTGTTCAGCCTGGTGCAGTGGGACCATCCAATGAGCT
TCCAGGAATGAGTGGGAGAGGAGCTCAGCTCTTTGCTAAAAGGCAGTCGA
GAATGGAGAAGTATGTGGTCGATTCAGACACGGTGCAGGCCCACGCTGCT
CGAGCTCAGTCTCCCACTCCATCTCTCCCGGCCAGTTGGAAGTACTCCTC
CAATGTCCGAGCACCTCCTCCTGTGGCCTATAATCCTATCCACTCGCCGT
CTTACCCACTGGCTGCTCTCAAGTCTCAGCCATCAGCTGCACAGCCCTCC
AAAATGGGCAAGAAAAAGGGAAAGAAACCCCTCAATGCATTAGATGTCAT
GAAGCACCAACCGTATCAGCTCAATGCATCCTTGTTTACTTTCCAACCTC
CAGATGCAAAGGATGGCCTCCCCCAGAAGTCATCAGTCAAGGTCAATTCA
```

FIG. 6a fohc 095
GCCCTGGCCATGAAGCAAGCTCTTCCTCCCCGGCCAGTGAATGCTGCCTC
ACCTACGAATGTGCAGGCTTCGTCAGTGTACTCGGTACCAGCCTATACCT
CTCCTCCTTCCTTCTTTGCAGAGGCCTCCTCACCAGTCAGTGCATCCCCA
GTGCCTGTGGGCATTCCCACCTCGCCAAAGCAAGAATCAGCCTCATCATC
TTATTTTGTGGCACCAAGGCCAAAGTTCTCAGCCAAGAAAAGTGGTGTCA
CAATTCAGGTGTGGAAACCATCTGTTGTGGAAGAGTAATCTTGTAGCTGA
AGCTGAGTGTCCACTTTGCTTGAAATGAATTGTTTGCAGTGTTTCTTGAG
TCCCTGAGAATGCCTAGCAAAGTCCTCAACTTACTTAATTTCAGATATGT
CACCTCCTAATCTGGGTCCAAGGAGTATAATATTTTTAATGAGTCAAAAA
TCCAACTCAGATTGACCTAAAATATATTTATCTTCTTTGCACACTTAAAA
AATCCAGGAGCACCCCAAAATAGACATGTACCGTTATATTAAGTAAGCAG
GAGACTTAGGATTTGTGCTGTAGCCACAAGAAAGACAGTGATCAGTGATA
TCAAACATCAGGAATCAGCCTTTATGTAACATAACAGCTGTCCTCCTATG
GTGAAAGGTTCAAATGTAGTGAAGGTATAACSTATATTGACTGAGATTTC
CCTTTTAGGTAGTGCCTTATCTCTATTACTAGTGTTAAAGGAGGGGGGGC
C   (SEQ ID NO:22)

FIG. 6b fohc101

AGACACCCGAGCTTATGACTCCTGTCATAAGCTGCGGATAGCAGGTCATC
CCTTATGTATGATTTCCATGTCCAGACCTTTCAGGAAGCTACAGGCAGAG
CCAGGTGATTGTCTCAAAATATGCCAGACAATTCTTGTGATATCAGATCC
AGAAAGGAGCCCTGGACCAGAGGAGCAGGAGAAAGGCGTTAAGAAGGCAA
CCATGAGCAAACACATCTTCCCCCCCCTAGAACGTGAGCTCAGTGTCTGC
AGGGGCCTGGTCTGACTGGCTAACATTATACCCCCAGCACCTAGAAATG
AGACAGAATAAATGCTCAATAAGCGACCATCTACAAACAGACAAAATAAA
TGCCCAATAAATGCTCACTGGATAAAGGAATCAAATCCTGAGGGTGCACA
ACATTTCCCAAGCAAGTGGCAAGAAGAGTCCAGAGCCGTCTCGCTCCCGA
TGCTGGCAGGTCTGTGTCCTCTCCTGCTTCTCTCTATGTGTTCCCTCGTT
CATACTCTGTTCTCATCTGCATCTTTTCCGTTTCTCCACTTTCAACAGCT
TCCCCACCCCAACCCAACCCCAATAACAAAACACTGGATTTAAAGTTAAA
AGGATATGATATTTTACTGTTGAATATATACAACTTCCCAAAGAAGCATA
GTAAAATTAATCACTTGCATTCTTTTCAGGTTAGTGTGACTGAGTCCACC
CACACAAGCTCTGGGGCTTCAGAAGGCTTGAATAAAGTGATACGTTAGAG
TAACACATATCCTGCCTTTACTAAAAACCTATAACATTTAATTTTATAAA
AAGTCAGGAAAGTCAGAGAATCCTAGGTATATAATCACCTTTTAAAAAAA
TTTTTCATTTTAACTTAAACATAGGGATAATGGCAAGCCACTCATAATGT
TGTCATTTGAAGATCACACCTTTTAATGTAGCTGAATTTGGAAGAGAGAA
GGAGAGAAACAGAAATGAGAAGGTTTGCTTAAAAAACAGATGCCAGTGCA
CAAATCTTAAAGAATTATAAGGCCTGGTGCGATGGCTCACACCTGTAATC
CCAGCACTTTGGGAGACAGAGGTGGGCGAATCACAAGGTCAGGAGTTCGA
GACCATCCTGGCCAACATGGTGTAACCCCATGTCTACCAAAAATACAAAA
AATTAGCTGGGCATGGTGGCGGGCACCTGTAATCCCAGCTACTGGGGAGG
CTGAGGCAGGAGAATCGCCTGAGCCTGGGAGGCGGAGGTTGTAGTGAGCT
GAGATCATGCCACTGCAACAAGCGTGAGACTCCATCTCAAAAAAAAAAAA
AAAAAAAAAAAA (SEQ ID NO:23)

FIG. 7

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
        (A) LENGTH: 171 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
AGGTGACCGT GGGGCATGAG GTGACTGGGG AAGGGAGACC TCTCCTGGCA GCATTTCTAG      60

GACCCAACAA GATCTGGAGG TGCCGGCTCT GGTTCCATCT CTAATCCCCT GCTGTGGCCT     120

GGCCAGTGTA CTGCCCGGAG CTGGAAACCA ATAAACCTGT GATTTGCCCC C             171
```

(2) INFORMATION FOR SEQ ID NO:2:

(i) SEQUENCE CHARACTERISTICS:
        (A) LENGTH: 251 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

```
AGGTGACCGT GACCTGAGAA GGAAAGAAAG ATCCTCTGCT GACCCCTGGA GCAGCTCTCG      60

AGAACTACCT GTTGGTATTG TCCACAAGCT CTCCCGAGCG CCCCATCTTG TGCCATGTTT     120

TAAGTCTTCA TGGATGTTCT GCATGTCATG GGGACTAAAA CTCACCCAAC AGATCTTTCC     180

AGAGGTCCAT GGTGGAAGAC GATAACCCTG TGAAATACTT TATAAAATGT CTTAATGTCC     240

AAAAAAAAA A                                                          251
```

(2) INFORMATION FOR SEQ ID NO:3:

(i) SEQUENCE CHARACTERISTICS:
        (A) LENGTH: 403 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:3:

TTTTTTTTTT TTTGGCGAGG TGGGAATGCC CACAGGCACT GGGGATGCAC TGACTGGTGA    60

GGAGGCCTCT GCAAAGAAGG AAGGAGGAGA GGTATAGGCT GGTACCGAGT ACACTGACGA   120

AGCCTGCACA TTCGTAGGTG AGGCAGCATT CACTGGCCGG GGAGGAAGAG CTTGCTTCAT   180

GGCCAGGGCT GAATTGACCT TGACTGATGA CTTCTGGGGG AGGCCATCCT TTGCATCTGG   240

AGGTTGGAAA GTAAACAAGG ATGCATTGAG CTGATACGGT TGGTGCTTCA TGACATCTAA   300

TGCATTGAGG GGTTTCTTTC CCTTTTTTTT GCCCATTTTG GAGGGCTGTG CAGCTGATGG   360

CTGAGAYYTK GMRAGCAGCC AGTGGGTAAG ACGGCGATTG AAG                     403

(2) INFORMATION FOR SEQ ID NO:4:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

TTTTTTTTTT TGGGAAGGGA GAAAAAGATT GCTTTGGTCT TTATTTTCTC AACTCATGAA    60

AAACTAAAAA CACTATTATT TTCCCTTAGA ATTTTGATTT GGAACATCTC TACAAATGCT   120

GAAGCTTTGT CATTTTATGT GTGTTTCTGA AGTAATATGG TTTTAACAGA GTTTATCAAA   180

CATTAGCATA GCTTCATCAA TTTTTCCTAG GAGAACTCCC TGGATATCAG GAACAGTGTG   240

TGTTGTGTTG TGTGTATGTG GTGTGTGTAT GTGAAGGGCC TG                      282

(2) INFORMATION FOR SEQ ID NO:5:

(i) SEQUENCE CHARACTERISTICS:
        (A) LENGTH: 198 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GGAGTGCCTC AGTAAGATAC AAATGAGTTG AATTGCCTTA TCTGGACTTA ATTCATGTAT    60

GTTTGGTTCT TGAGGTACAC GCTTACTGGA AGAGGTCCCC CAACCCATCT TCCCTTTTAA   120

AACTGGTGTT TGGAAACATC AAACACTACT AATAAACTCG AAACAACAAC CTACCCCCCC   180

ACCCCAAAAA AAAAAAAA                                                 198

(2) INFORMATION FOR SEQ ID NO:6:

(i) SEQUENCE CHARACTERISTICS:
        (A) LENGTH: 311 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GGCTAACCGA GAGAGCCGTA TATTAATTAA TCCTGGAAAC CATCTTAAGA TCCAAGAAGG    60

```
TACTTTAGGA TTTTTCATCG CAAGTGATGC CAAAGAAGTT AAAAGGGCAT TTTTTTACTG      120

CAAGGCCTGT CATGATGACA TCACAGATCC CAAAAGAATA AAAAAATGTG GCTGCAAACG      180

GCTCAAGGTT GCAGCTAGAT CACGCTATTC CAAAGATCCA TTTGAGTTCA AGAAGGAGAC      240

TCCCAATTCT CGGCTTGTGA CCGAGCCAGT TGAAGATGAG CAGCCGTCAA CACTATCACC      300

AAAAAAAAAA A                                                          311
```

(2) INFORMATION FOR SEQ ID NO:7:

(i) SEQUENCE CHARACTERISTICS:
        (A) LENGTH: 233 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
GGNNATCAGA TGTCTGGTAA CTGCTGCTTC TTGTTACTAT GATTATTTGA TGGAGGCCAG       60

TATTTCATTT AATTGCTAAN TCTGTCATAG TTTTATACTA GTAGCCACTA AGGTAGGTAG      120

TAATAGATTA TCTCCTTAAT GAAAATCCCT TTTATKAAAT GCGTAACAAG CTGTAATACA      180

GGGCCTAGTG TGTCATACAT NATNTTGGCT GCCCGNTAAA TTCACAATCT AGG             233
```

(2) INFORMATION FOR SEQ ID NO:8:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
TTGGCACGGG GACCATTTAC TCCACAATGT CTTTTGACCG GGAACATCAG ACCACATACA       60

CTTTCAGAGT CAAGGCTGTA GATGGGGGAG ATCCTCCCAG ATCTGCCACA GCTACAGTCT      120

CGCTTTTTGT GATGGATGAA AATGACAATG CTCCCACAGT TACCCTTCCC                 170
```

(2) INFORMATION FOR SEQ ID NO:9:

(i) SEQUENCE CHARACTERISTICS:
        (A) LENGTH: 326 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
TTCTTCCCCA AGCACCACAT CACAGCAGGC AAACTCTCAG TCAACTCCTG AGCCTTCACC       60

ATCACAGACA TTTCCCGAGT CTGTGGTAGC CGAGAAGCAG TATTTTATTG AAAAATTAAC     120

GGCGACAATC TGGAAGAACC TTTCTAATCC AGAAATGACT TCTGGATCTG ATAAAATTAA     180

TTATACATAT ATGTTAACTC GTTGTATTCA GGCGTGTAAG ACAAATCCTG AGTATATATA     240

TGCTCCTTTA AGAAAATTC CTCCTGCCGA CATCCCCAAA AAAAAAAAAG GCCGATTTCC      300

SGVACACTGG GGGCCGTTAA TNGTGG                                          326
```

(2) INFORMATION FOR SEQ ID NO:10:

(i) SEQUENCE CHARACTERISTICS:

(A) LENGTH: 382 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

AGCTTAGGGA TGTTCTGCAC TAAGGATTTA GCCAAGTGAG GATTAGCCCA GAGTGGCACA    60

ATGGGCTGCC AGCCGCCTTG TGAGCACGAG ATCTAGGCAG TCCCTGCGCA GACTGGTTAG   120

GAGAGGAAAT AGATGGCTCT TCCCTAGGGC CTCGTCTGTG TTTCTCTCAA TGAGTTGAGG   180

CCTGAAAGAG GCCACACTGG GACTCCCACT TGTGGCCCAG GCTAGAGAAG GCCTGGTCTG   240

GAGAGAAGTC ACAATTTTGA GAGTCATATA TAGTTTCTTC TGCAAAATGA GAGCTTATGA   300

AAGGTTTATT CACAAATAGT GTATGGAATA GAACTACCCT GGCNCAATCC TGTTACTGAG   360

CATCTGCCCA AAAAAAAAA AA                                            382

(2) INFORMATION FOR SEQ ID NO:11:

(i) SEQUENCE CHARACTERISTICS:
            (A) LENGTH: 314 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:11:

TTTCTCCGCT TGAATATCTA ATGGGCGTCT CAAACTTAAT ATGGCTAGGA TAATTTTTTA    60

ATTTCTAACC CCTATGCTCA CAAATCTCCT TGCAAGTCTT CCCTATCAGT AAATGACATT   120

AATGTCTCAG GCTTGGGGAT TAGACCCAAG TACTCCATGG CTCCAGGAGA GAGTCTAAGC   180

AGCATACTTG ATTCTTTCCT TCTTCTTACC ACCCTCCGCC TAATTCCTAG ATGAATCCTC   240

TTGGCTACCA CCTTAGTTCA TCATGTCTGA TTGGGCTGTT ATAGTCGCCT TCTAATTTCC   300

TCCCTGCCAA AAAA                                                    314

(2) INFORMATION FOR SEQ ID NO:12:

(i) SEQUENCE CHARACTERISTICS:
            (A) LENGTH: 297 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:12:

CGGCTTAAGC CCGAGGGAAG GAGGAGTTTC TTCAAATGGG AATAATAGCA TGACCAAGAT    60

TTGGACTTGA CACTGAATGT TTATGTGAGG GTTATATTGG AATCAACTTG ACCTGAATGG   120

AATTGTGAAC AAGTCATGGG AGATAAATGT GGTGTTTACA AGTGGAACAG AGTTGTTCTT   180

TTGAAAGGCA ACAAGCTATC ATCAGAAAGG TACCATATTG GGAGTTGGCA TGGAAATATG   240

TGATCTTAAT TAAGTCATTT ATTTTCTCCA GCTCTGTTTT CTCATCCAAA AAAAAAA     297

(2) INFORMATION FOR SEQ ID NO:13:

(i) SEQUENCE CHARACTERISTICS:
            (A) LENGTH: 114 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:13:

```
CTTACACAGA GGGGACAAGG TGGAGATGTT ACCAGACACC ACAGGCAAGG GAGCCCTCAT      60

GTTTGTCAAG AGGAGGGAGA GAATGGATCA GATCACAGCC CAAAAAAAAA AAAA           114
```

(2) INFORMATION FOR SEQ ID NO:14:

(i) SEQUENCE CHARACTERISTICS:
        (A) LENGTH: 218 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

```
TGTCTACGGC ATTTGAAGAG AGCGAGGAGA ACCATTCTGG AAACTCTAGG CTATGCATGT      60

TTAAAGATCT GGTCCCCTTT ATGAGAATGC AAGCCGATCC ACATCCTGAC TTAAGAGATC     120

TGATTCTGAC GAACTGCCTG GAGGAGGGGA ATATATAAAA ATAAAATTGG TGTCACTTCT     180

TTTCTGCTAT CCCCCAGCCC CCCCCCAAAA AAAAAAAA                            218
```

(2) INFORMATION FOR SEQ ID NO:15:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
GGCTTGGACG ACAAGCAGAA GCCAGTTATG ATGACAGGTG ATAGATCCAA ATAATTGCC       60

ACATTTGTTA ACATTTTTCC ATTTCTAAAC CATCCTTAAA GAAAATCATA TATGGGGTCA     120

CACCATCCTC ACGGTAGTCC AATAGAGCAA CCATGCCATC TGGATTCATG TTTTCACCAA     180

TAAAGAACTG GTAGTTTTTG AAATTAGCAA GGATGTGCTT GATTTGTTCT GCAGCCCCTG     240

TCATAAAAGG TTTTACTCTT TCTGGTCTCT GTTCTTCAAG TTTCCCTTTG ATTGATTTCA     300

TGTAATCTTT GATGTACTTC TTGTCGTCCA AGC                                 333
```

(2) INFORMATION FOR SEQ ID NO:16:

(i) SEQUENCE CHARACTERISTICS:
        (A) LENGTH: 308 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

```
GCTTTTCCCC CCAGCACCTA GAAATGAGAC AGAATAAATG CTCAATAAGC GACCATCACA      60

AACAGACAAA ATAAATGCCC AATAAATGCT CACTGGATAA AGGAATCAAA TCCTGAGGGT     120

GCACAACATT TCCCAAGCAA GTGGCAAGAA GAGTCCAGAC CGTCTCGCTC CCGATGCTGG     180

CAGCTCTGTG TCCTCTCCTG CTTCTCTCTA TGTGTTCCCT CGTTCATACT CTGTTCTCAT     240

CTGCATCTTT TCCGTTTCTC CACTTTCAAC AGCTTCCCCA CCCCAACCCA TCCCCAAAAA     300

AAAAAAAA                                                             308
```

(2) INFORMATION FOR SEQ ID NO:17:

(i) SEQUENCE CHARACTERISTICS:
        (A) LENGTH: 4972 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...2241

(xi) SEQUENCE DESCRIPTION: SEQ ID NO:17:

```
CCG TCC ATT GAA ATC CGC AAG ATT GGG CGC ATC CCC CTC AAG GAC GGG      48
Pro Ser Ile Glu Ile Arg Lys Ile Gly Arg Ile Pro Leu Lys Asp Gly
 1               5                  10                  15

GTG GCC AAC GTG GCC GAG GAC GTT CTG GTC GAC ACC CCC ATC GCT CTG      96
Val Ala Asn Val Ala Glu Asp Val Leu Val Asp Thr Pro Ile Ala Leu
             20                  25                  30

GTG CAG GTG TCC GAC CGA GAC CAA GGC GAG AAC GGG GTG GTC ACC TGC     144
Val Gln Val Ser Asp Arg Asp Gln Gly Glu Asn Gly Val Val Thr Cys
         35                  40                  45

ACC GTG GTG GGC GAC GTG CCC TTC CAG CTC AAG CCA GCC AGC GAC ACC     192
Thr Val Val Gly Asp Val Pro Phe Gln Leu Lys Pro Ala Ser Asp Thr
     50                  55                  60

GAG GGC GAC CAG AAC AAG AAA AAG TAC TTC TTG CAC ACC TCG ACC CCT     240
Glu Gly Asp Gln Asn Lys Lys Lys Tyr Phe Leu His Thr Ser Thr Pro
 65                  70                  75                  80

CTG GAC TAT GAG GCC ACC CGG GAG TTC AAC GTG GTC ATC GTG GCG GTG     288
Leu Asp Tyr Glu Ala Thr Arg Glu Phe Asn Val Val Ile Val Ala Val
                 85                  90                  95

GAC TCA GGC AGC CCC AGC CTC TCG AGC AAC AAC TCC CTG ATT GTC AAG     336
Asp Ser Gly Ser Pro Ser Leu Ser Ser Asn Asn Ser Leu Ile Val Lys
            100                 105                 110

GTG GGA GAC ACC AAC GAC AAC CCG CCC ATG TTC GGC CAG TCG GTG GTG     384
Val Gly Asp Thr Asn Asp Asn Pro Pro Met Phe Gly Gln Ser Val Val
        115                 120                 125

GAG GTT TAC TTC CCT GAG AAC AAC ATC CCG GGC GAG AGG GTG GCC ACG     432
Glu Val Tyr Phe Pro Glu Asn Asn Ile Pro Gly Glu Arg Val Ala Thr
    130                 135                 140

GTG CTG GCG ACA GAC GCA GAC AGC GGT AAG AAC GCC GAG ATC GCC TAC     480
Val Leu Ala Thr Asp Ala Asp Ser Gly Lys Asn Ala Glu Ile Ala Tyr
145                 150                 155                 160

TCG CTG GAC TCC TCT GTG ATG GGG ATC TTT GCC ATC GAT CCC GAT TCT     528
Ser Leu Asp Ser Ser Val Met Gly Ile Phe Ala Ile Asp Pro Asp Ser
                165                 170                 175

GGG GAC ATC CTG GTC AAT ACC GTG CTG GAC CGC GAG CAG ACT GAC AGG     576
Gly Asp Ile Leu Val Asn Thr Val Leu Asp Arg Glu Gln Thr Asp Arg
            180                 185                 190

TAT GAG TTT AAA GTT AAC GCC AAA GAC AAA GGC ATC CCC GTG CTG CAG     624
Tyr Glu Phe Lys Val Asn Ala Lys Asp Lys Gly Ile Pro Val Leu Gln
        195                 200                 205

GGC AGC ACT ACG GTG ATT GTG CAG GTG GCT GAT AAA AAT GAC AAT GAC     672
Gly Ser Thr Thr Val Ile Val Gln Val Ala Asp Lys Asn Asp Asn Asp
    210                 215                 220

CCT AAG TTT ATG CAG GAC GTC TTC ACC TTT TAT GTG AAA GAA AAC TTG     720
Pro Lys Phe Met Gln Asp Val Phe Thr Phe Tyr Val Lys Glu Asn Leu
225                 230                 235                 240

CAG CCC AAC AGC CCT GTG GGG ATG GTC ACC GTG ATG GAT GCT GAC AAG     768
```

```
               Gln Pro Asn Ser Pro Val Gly Met Val Thr Val Met Asp Ala Asp Lys
                                245                 250                 255

GGG CGG AAT GCA GAG ATG AGC CTG TAC ATA GAG GAG AAC AAT AAC ATT           816
Gly Arg Asn Ala Glu Met Ser Leu Tyr Ile Glu Glu Asn Asn Asn Ile
            260                 265                 270

TTT TCT ATT GAA AAT GAC ACG GGG ACC ATT TAC TCC ACA ATG TCT TTT           864
Phe Ser Ile Glu Asn Asp Thr Gly Thr Ile Tyr Ser Thr Met Ser Phe
        275                 280                 285

GAC CGG GAA CAT CAG ACC ACA TAC ACT TTC AGA GTC AAG GCT GTG GAT           912
Asp Arg Glu His Gln Thr Thr Tyr Thr Phe Arg Val Lys Ala Val Asp
    290                 295                 300

GGG GGA GAT CCT CCC AGA TCT GCC ACA GCT ACA GTC TCG CTT TTT GTG           960
Gly Gly Asp Pro Pro Arg Ser Ala Thr Ala Thr Val Ser Leu Phe Val
305                 310                 315                 320

ATG GAT GAA AAT GAC AAT GCT CCC ACA GTT ACC CTT CCC AAA AAC ATT          1008
Met Asp Glu Asn Asp Asn Ala Pro Thr Val Thr Leu Pro Lys Asn Ile
                325                 330                 335

TCC TAC ACT TTA CTG CCA CCT TCG AGT AAT GTC AGG ACA GTA GTA GCT          1056
Ser Tyr Thr Leu Leu Pro Pro Ser Ser Asn Val Arg Thr Val Val Ala
            340                 345                 350

ACA GTG TTG GCA ACA GAC AGT GAT GAT GGC ATC AAT GCA GAC CTG AAC          1104
Thr Val Leu Ala Thr Asp Ser Asp Asp Gly Ile Asn Ala Asp Leu Asn
        355                 360                 365

TAC AGC ATT GTG GGA GGA AAT CCC TTC AAG CTG TTT GAA ATT GAT CCC          1152
Tyr Ser Ile Val Gly Gly Asn Pro Phe Lys Leu Phe Glu Ile Asp Pro
    370                 375                 380

ACT AGT GGT GTG GTT TCC TTA GTG GGA AAA CTC ACC CAA AAG CAT TAT          1200
Thr Ser Gly Val Val Ser Leu Val Gly Lys Leu Thr Gln Lys His Tyr
385                 390                 395                 400

GGC TTG CAC AGG TTG GTG GTG CAA GTG AAT GAC AGT GGG CAG CCT TCC          1248
Gly Leu His Arg Leu Val Val Gln Val Asn Asp Ser Gly Gln Pro Ser
                405                 410                 415

CAG TCC ACC ACG ACT CTG GTG CAC GTG TTT GTC AAT GAA AGT GTT TCT          1296
Gln Ser Thr Thr Thr Leu Val His Val Phe Val Asn Glu Ser Val Ser
            420                 425                 430

AAT GCA ACT GCG ATT GAC TCC CAG ATA GCT AGA AGT TTG CAC ATC CCA          1344
Asn Ala Thr Ala Ile Asp Ser Gln Ile Ala Arg Ser Leu His Ile Pro
        435                 440                 445

CTC ACC CAG GAT ATA GCT GGT GAC CCA AGC TAT GAA ATT AGC AAA CAG          1392
Leu Thr Gln Asp Ile Ala Gly Asp Pro Ser Tyr Glu Ile Ser Lys Gln
    450                 455                 460

AGA CTC AGT ATT GTC ATT GGC GTG GTT GCT GGC ATT ATG ACG GTG ATT          1440
Arg Leu Ser Ile Val Ile Gly Val Val Ala Gly Ile Met Thr Val Ile
465                 470                 475                 480

CTA ATC ATC TTA ATT GTA GTG ATG GCA AGG TAC TGC AGG TCC AAA AAT          1488
Leu Ile Ile Leu Ile Val Val Met Ala Arg Tyr Cys Arg Ser Lys Asn
                485                 490                 495

AAA AAT GGC TAT GAA GCC GGC AAA AAA GAT ACG AAG ACT TTT TTT ACA          1536
Lys Asn Gly Tyr Glu Ala Gly Lys Lys Asp Thr Lys Thr Phe Phe Thr
            500                 505                 510

CCC CAA CAG CAT GAC AAA TCT AAA AAG CCT AAA AAG GAC AAG AAA AAC          1584
Pro Gln Gln His Asp Lys Ser Lys Lys Pro Lys Lys Asp Lys Lys Asn
        515                 520                 525

AAA AAA TCT AAG CAG CCT CTC TAC AGC AGC ATT GTC ACT GTG GAG GCT          1632
Lys Lys Ser Lys Gln Pro Leu Tyr Ser Ser Ile Val Thr Val Glu Ala
    530                 535                 540

TCT AAG CCA AAT GGA CAG AGG TAT GAT AGT GTC AAT GAG AAG CTG TCA          1680
Ser Lys Pro Asn Gly Gln Arg Tyr Asp Ser Val Asn Glu Lys Leu Ser
545                 550                 555                 560
```

```
GAC AGC CCA AGC ATG GGG CGA TAC AGG TCC GTT AAT GGT GGG CCC GGC    1728
Asp Ser Pro Ser Met Gly Arg Tyr Arg Ser Val Asn Gly Gly Pro Gly
                565                 570                 575

AGT CCT GAC CTG GCA AGG CAT TAC AAA TCT AGT TCC CCA TTG CCT ACT    1776
Ser Pro Asp Leu Ala Arg His Tyr Lys Ser Ser Ser Pro Leu Pro Thr
            580                 585                 590

GTT CAG CTT CAT CCC CAG TCA CCA ACT GCA GGA AAA AAA CAC CAG GCC    1824
Val Gln Leu His Pro Gln Ser Pro Thr Ala Gly Lys Lys His Gln Ala
        595                 600                 605

GTA CAA GAT CTA CCA CCA GCC AAC ACA TTT GTG GGA GCA GGA GAC AAC    1872
Val Gln Asp Leu Pro Pro Ala Asn Thr Phe Val Gly Ala Gly Asp Asn
    610                 615                 620

ATT TCA ATT GGA TCA GAT CAC TGC TCT GAG TAC AGC TGT CAA ACC AAT    1920
Ile Ser Ile Gly Ser Asp His Cys Ser Glu Tyr Ser Cys Gln Thr Asn
625                 630                 635                 640

AAC AAG TAC AGC AAA CAG CCA TTT CGT AGA GTG ACG TTT TCT GTT GTG    1968
Asn Lys Tyr Ser Lys Gln Pro Phe Arg Arg Val Thr Phe Ser Val Val
                645                 650                 655

AGT CAG CCT CAG GAC CCA CAT CAG GGG TCA CTG CAG AGT TGC TAT GAC    2016
Ser Gln Pro Gln Asp Pro His Gln Gly Ser Leu Gln Ser Cys Tyr Asp
            660                 665                 670

AGC GGG CTG GAG GAG TCA GAA ACA CCA AGC AGT AAG AGT TCA TCA GGG    2064
Ser Gly Leu Glu Glu Ser Glu Thr Pro Ser Ser Lys Ser Ser Ser Gly
        675                 680                 685

CCA AGA CTG GGT GCG CTT CCA CTC CCA GAG GAC AAC TAT GAA AGG ACC    2112
Pro Arg Leu Gly Ala Leu Pro Leu Pro Glu Asp Asn Tyr Glu Arg Thr
    690                 695                 700

ACG CCG GAT GGC AGT GTT GGT GAG GCA GAG CAT ATG GAA AAT GGT GTT    2160
Thr Pro Asp Gly Ser Val Gly Glu Ala Glu His Met Glu Asn Gly Val
705                 710                 715                 720

GCT GCC ATC ACT ACC TTT CCC TTC CTC CCC TTT CCT CAT GGC AAG ACG    2208
Ala Ala Ile Thr Thr Phe Pro Phe Leu Pro Phe Pro His Gly Lys Thr
                725                 730                 735

CAT GGA AGA AGA GTG CTG TTA AGG CCT CTC CAT TAATCAACAG ATTCAAGGCC  2261
His Gly Arg Arg Val Leu Leu Arg Pro Leu His
            740                 745

TCTTCCAGAT GTAGCCCTGA CTGGGAAGTG CACTCGTGAG TGTGATGAGT ATGGCCACTC  2321

AGACTCCTGC TGGATGCCGG TCCGCACTTC TCCGGAGAGG AAGAAGAGCC AGCCTAAACT  2381

GTCCACTTWC ATGCCTGTTG ATGAACGAGG AAGCCAGGAA AAGCTGGCCA ATGGGGAGGC  2441

CGCCATCATG GGTGACCGCA ACAGAAACCT CCTGAACAAA AGTTGACCT CATCCTATGA   2501

GACCTTCAGT GCAGCTAGTT TCAGCAAAAA TGAGGAAGCC AACCCTGAGG ATATTCCCCT  2561

TACAAAAACA GGGGAATATA AGCCATCTCC TGTCAATACT CTCACTAGAA GAGAAGTTTA  2621

CCTGTAGGTT ATAAAGGAGC AACAGCAAAG TTCTTTACAT GTATGAAAAG GAGAATAAGG  2681

GGCAAAAACC TTACAAAGCA AAACGTTTAA TCACAAAGAG GGGGCTACCA AAGAGACAAA  2741

GCTTTGCCTG CCACTTCTGC CTCCAGATCA GGCCTTTAGT GATACTGTTA GCCTGATTCT  2801

ACTGTACAAT GTAGAAACCA TCCTTGTTAC TTGCATGTCT AACCCCTTCA CTGATTCCCA  2861

ACACTCACTT TCTCTTCCCC ACCCCTCTCC MMAAAAAAAA AAAAAAAAAG AAAAGAAAAA  2921

AAAAAGGGGG ATAGTTGCAA GTTTCTTTCA CAGTAACTGT ACGAAGCCTG ATTAGCAGAA  2981

CACAACACAC CCTCATTATC CCTAAGCTGA AGCATGATTT TAGTCACTTT GATTTGTTC   3041

GAGTGTCATC TGGCTGGTCA AAAATAAGCA GGACAGATAA AATGTATTTC AGACATACCA  3101

TCAGAAAATG GTTTATCACC ATCAAAGGCA ATCCTTTGAA AGTGATAGAG TCCCTCTAAA  3161

GGTACAGTCC TTAGAAAGAG GGACTGTATT AAAAAGTATG GTGGGAATAT CAAAGCTTTA  3221
```

```
ATATTCCAAC AAAGACTAAG AGAAAAACAA TACTCAGTGG GTGATTGCAG TCCTAAATTG    3281

TCATATGTTG TTATTTTCAG GTCAAGAGCA TCAACTTCAA TTCCATACAT TCACCAAATA    3341

TTCTCAGTAT ACACACAGTC TTGATTACAT GTATCAATTT CACCAGTTAT GACTTCTAAA    3401

AATTATATAT ATTTTTTCAG AACAAGACCA CTATTATTAA CTAACTTGAA CAATTGTATC    3461

ATCCAAAGGC CAAAGATCAT ATGGCAGATC AGGGAAGTCA TGAAGTTGAT TTGGTCTTGA    3521

CGTGGAAAAC CATTAAACAA CAAAAGCAAC TGAACCCATG TATGCACAGA AACAATCAAA    3581

CACTAGTTCA TTTTATAGTG CCCAGGAAAA TGTTCCTTCT TTTAAAATGG ATTTTATTTG    3641

AAAGCGCAGA AAATGAAAAC TAGTGAGATA TATTTTTGGT ATTATAATAG GCAATTGGTT    3701

GAGGTTCAAG TTTAGTTTCA GGTAATATTA TCAGGGAAGA TTCCATGTTT TAAAATAGTA    3761

TTTATGGATC ATGGGTAGGT TAAGAAAGAT GCATTGGCAT ATAGTCTTGA TAGTTAAGTC    3821

CACGATTATC ATTTTAGAAT CCAGGCTATG CTTGCTGCTC TTTTTATCCA CATTTTAAAT    3881

TACAATTGCA TTTTTTACTT GTTCAGTGCA CACTTTGATG CACCACAAGT GCATTAATTT    3941

TGAATCGTGT GCAATATAGA AATATTTTGA GACTCACAAC ATTGAAACAA GGTGACACCC    4001

TAGTTGACTT TATCACTAAT GTGATTTGAA CATTATTTAA ACAAATCTAG ACTGAACATG    4061

AAAGAAAGGA GTTTTGGGCA GTGACATTTT TCACAGAATG TATATCTCAA AGGTGAAAGC    4121

AGAGTTTTTC CAGTGCAATA AAAAGAAACA GAATATGCAG ATTTTGAGCT ACTCGCTCTA    4181

TAGAGGATAA CCTAACACGG CTGAAAATTG AGCTGGGACA TTCAGACGAA AGTGACAATC    4241

CATGGACAGA ATAGGGAATA ACAGGTGTGA AGAGAACAAA CTTATCACTG AATGTTTGCA    4301

AGCTGGTTAA GGCATAGCCT TGATGGCTCT CTAGCAAACT GTAGAAACAA TGTAGCTTTG    4361

GGTAGTTTCA TGCTTTGCAG AATTTCTTAG ACTATAAAGT GACACAGCCT GGAATATAGG    4421

TTGATAATTC ACTATAGGTC TTCNAAATAC TTATCTTTGA AAACCGCTTC TCTGTNTGGT    4481

GGGGTACAAT TTGGGGGTCA TTTCCTTATG CTCTTTCTTA AATGGAGTTT TCATTTTGAT    4541

GTTAGTTTAT GTATAATAGG TAGGATGCAA AAAGATATGT AATTGAAACA AAAAACATTG    4601

GACTAAAATA TCAGTAATTG AACATGTTTA TGTTTGATTA TTATTTACAC TATGGAAAGA    4661

TGCAATTCTA GTACTTTGTT AGGAAACTGC ATTAAAGCAG TTCTGCCTTG TATAATCTGT    4721

AAGTACCTAT TAAGACAAAA TACTTCTAAA GATACTTATG AAATGTATAC ATATTTTTTC    4781

TTGCACGTTA CAAAGAAAAT ACTCAATTGC ATAACACGGA TGTTTGACAA ACTTTTTTTT    4841

TTTAATGCAT TTCTTTCTTT CATGAGACAT TGAAACCACT GATAGCTCAT TTCACCCTAT    4901

CTTAAACCCT TCTCTTGTCT ATAAAACTAA TACGGGTCAC ACCGGACCTT CGGATTAATT    4961

GGATCCACAT T                                                        4972
```

(2) INFORMATION FOR SEQ ID NO:18:

(i) SEQUENCE CHARACTERISTICS:
        (A) LENGTH: 747 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:18:

```
Pro Ser Ile Glu Ile Arg Lys Ile Gly Arg Ile Pro Leu Lys Asp Gly
  1               5                  10                  15

Val Ala Asn Val Ala Glu Asp Val Leu Val Asp Thr Pro Ile Ala Leu
```

```
                20                  25                  30
Val Gln Val Ser Asp Arg Asp Gln Gly Glu Asn Gly Val Val Thr Cys
            35                  40                  45
Thr Val Val Gly Asp Val Pro Phe Gln Leu Lys Pro Ala Ser Asp Thr
        50                  55                  60
Glu Gly Asp Gln Asn Lys Lys Lys Tyr Phe Leu His Thr Ser Thr Pro
65                  70                  75                  80
Leu Asp Tyr Glu Ala Thr Arg Glu Phe Asn Val Ile Val Ala Val
                85                  90                  95
Asp Ser Gly Ser Pro Ser Leu Ser Ser Asn Asn Ser Leu Ile Val Lys
            100                 105                 110
Val Gly Asp Thr Asn Asp Asn Pro Pro Met Phe Gly Gln Ser Val Val
            115                 120                 125
Glu Val Tyr Phe Pro Glu Asn Asn Ile Pro Gly Glu Arg Val Ala Thr
            130                 135                 140
Val Leu Ala Thr Asp Ala Asp Ser Gly Lys Asn Ala Glu Ile Ala Tyr
145                 150                 155                 160
Ser Leu Asp Ser Ser Val Met Gly Ile Phe Ala Ile Asp Pro Asp Ser
                165                 170                 175
Gly Asp Ile Leu Val Asn Thr Val Leu Asp Arg Glu Gln Thr Asp Arg
            180                 185                 190
Tyr Glu Phe Lys Val Asn Ala Lys Asp Lys Gly Ile Pro Val Leu Gln
            195                 200                 205
Gly Ser Thr Thr Val Ile Val Gln Val Ala Asp Lys Asn Asp Asn Asp
            210                 215                 220
Pro Lys Phe Met Gln Asp Val Phe Thr Phe Tyr Val Lys Glu Asn Leu
225                 230                 235                 240
Gln Pro Asn Ser Pro Val Gly Met Val Thr Val Met Asp Ala Asp Lys
            245                 250                 255
Gly Arg Asn Ala Glu Met Ser Leu Tyr Ile Glu Glu Asn Asn Ile
            260                 265                 270
Phe Ser Ile Glu Asn Asp Thr Gly Thr Ile Tyr Ser Thr Met Ser Phe
            275                 280                 285
Asp Arg Glu His Gln Thr Thr Tyr Thr Phe Arg Val Lys Ala Val Asp
            290                 295                 300
Gly Gly Asp Pro Pro Arg Ser Ala Thr Ala Thr Val Ser Leu Phe Val
305                 310                 315                 320
Met Asp Glu Asn Asp Asn Ala Pro Thr Val Thr Leu Pro Lys Asn Ile
            325                 330                 335
Ser Tyr Thr Leu Leu Pro Pro Ser Ser Asn Val Arg Thr Val Val Ala
            340                 345                 350
Thr Val Leu Ala Thr Asp Ser Asp Asp Gly Ile Asn Ala Asp Leu Asn
            355                 360                 365
Tyr Ser Ile Val Gly Gly Asn Pro Phe Lys Leu Phe Glu Ile Asp Pro
            370                 375                 380
Thr Ser Gly Val Val Ser Leu Val Gly Lys Leu Thr Gln Lys His Tyr
385                 390                 395                 400
Gly Leu His Arg Leu Val Val Gln Val Asn Asp Ser Gly Gln Pro Ser
            405                 410                 415
Gln Ser Thr Thr Thr Leu Val His Val Phe Val Asn Glu Ser Val Ser
            420                 425                 430
Asn Ala Thr Ala Ile Asp Ser Gln Ile Ala Arg Ser Leu His Ile Pro
            435                 440                 445
```

```
Leu Thr Gln Asp Ile Ala Gly Asp Pro Ser Tyr Glu Ile Ser Lys Gln
    450                 455                 460

Arg Leu Ser Ile Val Ile Gly Val Val Ala Gly Ile Met Thr Val Ile
465                 470                 475                 480

Leu Ile Ile Leu Ile Val Val Met Ala Arg Tyr Cys Arg Ser Lys Asn
                485                 490                 495

Lys Asn Gly Tyr Glu Ala Gly Lys Lys Asp Thr Lys Thr Phe Phe Thr
                500                 505                 510

Pro Gln Gln His Asp Lys Ser Lys Pro Lys Lys Asp Lys Lys Asn
            515                 520                 525

Lys Lys Ser Lys Gln Pro Leu Tyr Ser Ser Ile Val Thr Val Glu Ala
    530                 535                 540

Ser Lys Pro Asn Gly Gln Arg Tyr Asp Ser Val Asn Glu Lys Leu Ser
545                 550                 555                 560

Asp Ser Pro Ser Met Gly Arg Tyr Arg Ser Val Asn Gly Gly Pro Gly
                565                 570                 575

Ser Pro Asp Leu Ala Arg His Tyr Lys Ser Ser Ser Pro Leu Pro Thr
                580                 585                 590

Val Gln Leu His Pro Gln Ser Pro Thr Ala Gly Lys Lys His Gln Ala
            595                 600                 605

Val Gln Asp Leu Pro Pro Ala Asn Thr Phe Val Gly Ala Gly Asp Asn
    610                 615                 620

Ile Ser Ile Gly Ser Asp His Cys Ser Glu Tyr Ser Cys Gln Thr Asn
625                 630                 635                 640

Asn Lys Tyr Ser Lys Gln Pro Phe Arg Arg Val Thr Phe Ser Val Val
                645                 650                 655

Ser Gln Pro Gln Asp Pro His Gln Gly Ser Leu Gln Ser Cys Tyr Asp
            660                 665                 670

Ser Gly Leu Glu Glu Ser Glu Thr Pro Ser Ser Lys Ser Ser Ser Gly
                675                 680                 685

Pro Arg Leu Gly Ala Leu Pro Leu Pro Glu Asp Asn Tyr Glu Arg Thr
    690                 695                 700

Thr Pro Asp Gly Ser Val Gly Glu Ala Glu His Met Glu Asn Gly Val
705                 710                 715                 720

Ala Ala Ile Thr Thr Phe Pro Phe Leu Pro Phe His Gly Lys Thr
                725                 730                 735

His Gly Arg Arg Val Leu Leu Arg Pro Leu His
            740                 745
```

(2) INFORMATION FOR SEQ ID NO:19:

(i) SEQUENCE CHARACTERISTICS:
        (A) LENGTH: 909 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

```
GGCTTCTTTC CCAGTAAGCG TGTACCTCAA GAACCAAACA TACATGAATT AAGTCCAGAT     60

AAGGCAATTC AACTCATTTG TATCTTACTG GAGGCACATC CAACCAAGGA AGAATAGAGA    120

CTTAGTTATA TTAGGCTCTC TCCCAGCTCT GAGATGAGTA TATTCTTTGG GGGGCTTGCT    180

AATGTTGCAA GTTTGCATTC AAAATAAATT CTAGGCACTC ACATAATCCC CCAGTCTCCT    240
```

```
CCAAACTTTC TTTGATGTCC AACAACTAAG GACAAGGATC TTTGATTATA AAACAATTTC    300

TTTGGTTGGA AGAAAATTCT TTGCAGGGCG TGAACAGCCG GAGAAAGAAA AGGTTTTTCT    360

GAAGTGCAAA CTAGTTGGAA ACCCCCTGGG GAAAGAATCT GATTCCCAGT CTTTGAGAGG    420

ACCAGGCCTG CCTGTACAAG TTGCCTCTGC TGAAGGCCTC TAAGAAGGCG CTTTTGNGTC    480

TACTGTATGG CCCTCAGCAA CAGCACGGCR GCCCTTCTCT TTTTTTTTGG CAGCGGAAGT    540

TTTCCATCTC TGGGAATACA CAATGCAGAA AGTCACGGTT AATAACAAG GCATAGTTAC     600

TAATCAGATG GCCCCATTTC CACTCTTCCC AGTTGCCTCC AGATGCTTAC ATACTAGAGC    660

TCTATCCCCC TCACCCCATG GGTGAACACC CACCAGCTGC TCTGAAATCT TATTTTTAGT    720

ATAAGTATTC AGCTTATCTC TAATAATTCA CTTCACAGAG TACTTAGGAT CAGAAGCATC    780

CTACTCCTTT TACTTTCATC CAGACTGGTT CTAGGTTGTC TCTGGCTCTT TCAGGTTTTT    840

CCAAAGGTTA GATTCACTTA GGTGCAGGAC CTGCCCGGGC GGCCGCTCGA GCCCTATAGT    900

GAGTAAGCC                                                           909

(2) INFORMATION FOR SEQ ID NO:20:

(i) SEQUENCE CHARACTERISTICS:
        (A) LENGTH: 1888 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

TTACTCACTA TAGGGCTCGA GCGGCCGCCC GGGCAGGTCA CACACATAAA ATTAGCTGGC     60

ATGGTGTTAT GTGCCTGTAG TCCCAGCTAC TCAGGAGGCT GAGAGGCAGA AGGATTGCTT    120

GAGCCCAGGA GTTCGAGGCT ACAGTGAGCT ATGATCATGC TACTGCACTC CAGCCTGGGT    180

GGCAGAGAGA GACCTTGTCT CTCTAAAAAA TAAAAAATAA TAAATTTCTT TACAAAATTT    240

GTGATCAAGT CAGGGCTTAT TTCACTTAAG ATGAAGACCT CTGGTTATAC TACCATGTTG    300

CTGCAAAAGA CAGGATTTCA TTATTTTTTG TGGCTGAATA ATATTCCATT GCATATATAT    360

ACATTTTCTT TATCCATTCA TCCATTGATG GACACTTAGA TTGATTCCAT ATCTTTGCTA    420

TTGTCAATAA TACTGTAATA AAAATATAAG TGCAAGTATG TCTTTGATAC TAATATATTG    480

ATTTCTTTTC CTTTGGGCAG ATGCTCAGTA ACAGGACTGT GCAGGGTAGT TCTATTCCAT    540

ACACTATTTG TGAATAAACC TTTCATAAGC TCTCATTTTG CAGAAGAAAC TATATATGAC    600

TCTCAAAATT GTGACTTCTC TCCAGACCAG GCCTTCCCTA GCCTGGGCCA CAAGTGGGAG    660

TCCCAGTGTG GCCTCTTTCA GGCCTCAACT CATTGAGAGA AACACAGACG AGGCCCTAGG    720

GAAGAGCCAT CTATTTCCTC TCCTAACCAG TGCTGCGCAG GGACTGCCTA GATCTCGTGC    780

TCACAAGGCG GCTGGCAGCC CATTGTGCCA CTCTGGGCTA ATCCTCACTT GGCTAAATCC    840

TTAGTGCAGA ACATCCCTAA GCTGACCACA TCTCTGCAAA ACCTGAGACA TACCCAGGCC    900

TGGTCTGCTA AGATGGAATC TGTGAAGTTT GCCCAGATGG TCAGATCAAA TGTCTGGCTG    960

AATTCCCACT GTGCTAGCTT TATCTCATTC CTGTCATCTT CCACACTGGT AACTGGATCA   1020

AATAAGCTTT TACTGGCAGG ACAAATCAAC GGATAAAGGA AAGACTGTTC CATGAAGCTG   1080

TCCTGGGATA GCAAGTTAGT AAATTGAAGG GAAAAGTGTG TTAGAGTTTC TTCTTGCACT   1140

ATGAACTGAA GTAAATTTGA GACAGGTCAA AGAACTTAAA AATCAATCCA CGGAACCTCT   1200

AGAAGACTCT AGAATTGTAC ATTAAAAAAT AAATCAATAT GTAAATGATC AACACATTGA   1260
```

-continued

```
ACTGCATGAA AATATTTTAC ATATTTTTCA AAATAACTGA AAGGGAAGAA TGGGAGAGAA    1320

AACTTCAAAT ATGTAATGAG ATCAGACCTA CTGATAAGAA AAATATGAAT ACCCCATCAA    1380

TAGGTATATG ATATGAATAC ATAATTCCAA AAACTAAAAA TAACTAGTAA ACAAATACAT    1440

AGGATGGCTT TCAACCTCTC CAGTTATCAA AGAAATACAA ACCTATTAGC TATGAATTTT    1500

CACCTGTTAA AATGATTTTT TAAGTTATAG TAATATCAAA TATCAGTGTA AATAACACTG    1560

TTGTACACAA TTAGTGAGAC TGTTAATTTG AATAAATCTT TGGAGGCCAT TTTCTTGTTT    1620

ACTTATACTT CTAGAAATCA TTCTATGGAA ATCAGCAAAA CTTGGGAAAA AACATATAAA    1680

ACGGTCATTT TAAATGTTAA TAGTAAAAAT TTAGAAAAAT TTGATGTTAT TTTATAGCAA    1740

TTAAAAAGAC GAATTTGAAA ACTGAAAATG CTTATGAATA AACTTTAAGA TGTGTTACGT    1800

ATAAGGTAAA ATTCTATCAA CGTTATGTAA AAAATATACA GTAATAACAC TAGAAAAATA    1860

TTCATCAAAA TTCCTATAGT GTCTATCT                                       1888
```

(2) INFORMATION FOR SEQ ID NO:21:

(i) SEQUENCE CHARACTERISTICS:
        (A) LENGTH: 2096 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

```
CTCTGTTCCA CTTGTAAACA CCACATTTAT CTCCCATGAC TTGTTCACAA TTCCATTCAG      60

GTCAAGTTGA TTCCAATATA ACCCTCACAT AAACATTCAG TGTCAAGTCC AAATCTTTGT     120

TCATGCTATT ATTCCCATTT GAAGAAACTC CTCCTTCCCT CGGGCCTCTG TATTCTACGT     180

TCTTTGAAAT CCAGGTCAAG TGTCACTCCA ACCCCTCCAA GATGTATCAA GGCTGTAACT     240

TCAGCCGACC TAGACAATAT CCCTCTACTA TAGCATTTGA ATTGTACTAT ACCAATGTGA     300

GACATGTAAT CATATTATTT CATGTTTACT CAACATTTTT GTGTATGGGG ACTTCACTTC     360

TTGACTAAAC TCAACTTCTT AAGTGAGCTG GATCATGTCT TTTCTATTGT GTTATCCTTC     420

ACAGTGAGTA TAGCTCTTTG CAAAGTAGGT ACTTTACCGT TTGTTGAAAA TATAAAGAAT     480

CTAAAAATAG AATTTGAAAC AAAATTTTCA ATAGGTAATC CAAGAGCCCA GAGAAAATCA     540

AGTCCATAGA CAAATCAAGC TTAATTTCAC AATTAGCTTA AGTTAATTCA CTCATTTGAC     600

AAGTATATAA TGAGTGCCTG CACTGAGCTC ATTAAAGTGC TAAGCATTAA ACTGCAATGG     660

TGAGTGAAAC AGACACATCC CTGCCAACGT GGAGCTAACA GTCTAGTTAG AGGAACACAC     720

ACATATATTA AAAGTTTAAC CAGGACTCTA GAGAACATGA AAAGAAGTGA ACAGATTTGG     780

GATACATGAT TAAAGGAAAG GAGTGAGGGC CAGGAAAGAA TAAAAAATAA CTTGTGAATT     840

TCTGGTACGT GCAACAGGAA GGATAACCAT GCCATTTCCC CTGAGTTGGA GAAAACCAGT     900

GGAGGACAAG GTTTATGGGG GTATATCAGG AAAACTCAAC CTTGGGCATG CTGAACAATT     960

CCATTAGCAG AACCTATTAG GTAAAAGAAG TTGACCCCAA ATGGTTTCAA GTTTTTTTTT    1020

TTTTGACCTT TACCCTATTC ATTGTCATAA ACACCCTATA CTTCCCCAAA AGTAAAAGCT    1080

CTACCAAGTA GGCCTGAGAA GAGGAAAGCA GAATCAAGGA CTCAGACAGC CCAGAATTGG    1140

GTAATTAAAC TAACTGGGTA GGTTAGGGTT CACTGAGGCA AGGAGAATAT AAAATAAATC    1200

TTTTCAATCA AAGAAAATAA AATCTGGCCT ATTTATTTCT CTTTATCGAG TGAATCAAAA    1260

GCTTGGCTAA ATTGAAAACC CTAAAACCCA ATCTAAAAAA GAGGATGGCT CCTGGTGTTT    1320
```

-continued

```
GTATACATCC ATGCAAGAGG TAGGCTTGCG TAGAGGCTCT TAATCTTCAC TCCCCCTCTG    1380

AGACAYTGTT GGCTGCTGTA TAATATTGTG GTATAAATGA GGCCAGCGTT CTGGATTAAA    1440

ATCTCTTCAA GCCTCTTCAT TGATCACAGG GTTGGAAAGA AACATAGAAG TTCAATACCT    1500

CATATAATCA AAAAATCAAA AAACTTTGGA ATCAGAAGGA ACGTAGGGCT CACGTCTTCT    1560

AAATTCTTTC TTTCCAAGTA AGCATCTCTT GTAAGACATT ATTTTACAGA GAAGAAAACC    1620

AATCAAAGTC TGAAAGGTA AAATGACTTG CCTGCCTAAG GTAACACAGC AAATTAGTGA     1680

CAAAGCTGGG AAAAGAACCA TGCTCTCTTG CTTCTTGCCA CTATACCATA CAGTCTGGAG    1740

GGAAAAGAGA AGGGTCTGCC TAGAGAACAG TTCCTTTCGG AAAGTAATTT GAGATCAAGT    1800

TGATGATATC TAGGGATGAT AATTTCCATT CTAAGTTTCA ATTTGCTAAA TGAAGCCCCC    1860

ATAGGTACTT AATCACATGA GTAAAATGAC CGAAATGATA CTTGAAAAAT ACAAAATTCA    1920

TAGTAGATGA TTTTGTGATA TTCAAGATAT GGGAAATAGA GCAGCTTGTT ATAGAAATCT    1980

AGGCACAAGC TAATGAGGAT AGTGACTCTG CAGGTGGCAA GAAAAGATGA CTTAACTTAG    2040

GGGCACTGTG CAGGGTGATG GGCGTCTGAC TGATGCAGAT ATAAAAGGAA TAAAGA       2096
```

(2) INFORMATION FOR SEQ ID NO:22:

(i) SEQUENCE CHARACTERISTICS:
        (A) LENGTH: 1313 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

```
AGACACCCGA GCTTATGACT CCTGTCATAA GCTGCGGATA GCAGGTCATC CCTTATGTAT      60

GATTTCCATG TCCAGACCTT TCAGGAAGCT ACAGGCAGAG CCAGGTGATT GTCTCAAAAT     120

ATGCCAGACA ATTCTTGTGA TATCAGATCC AGAAAGGAGC CCTGGACCAG AGGAGCAGGA     180

GAAAGGCGTT AAGAAGGCAA CCATGAGCAA ACACATCTTC CCCCCCCTAG AACGTGAGCT     240

CAGTGTCTGC AGGGGCCTGG TCTGACTGGC TCAACATTAT ACCCCCAGCA CCTAGAAATG     300

AGACAGAATA AATGCTCAAT AAGCGACCAT CTACAAACAG ACAAAATAAA TGCCCAATAA     360

ATGCTCACTG GATAAAGGAA TCAAATCCTG AGGGTGCACA ACATTTCCCA AGCAAGTGGC     420

AAGAAGAGTC CAGAGCCGTC TCGCTCCCGA TGCTGGCAGG TCTGTGTCCT CTCCTGCTTC     480

TCTCTATGTG TTCCCTCGTT CATACTCTGT TCTCATCTGC ATCTTTTCCG TTTCTCCACT     540

TTCAACAGCT TCCCCACCCC AACCCAACCC CAATAACAAA ACACTGGATT TAAAGTTAAA     600

AGGATATGAT ATTTTACTGT TGAATATATA CAACTTCCCA AGAAGCATA GTAAAATTAA      660

TCACTTGCAT TCTTTTCAGG TTAGTGTGAC TGAGTCCACC CACACAGCT CTGGGGCTTC      720

AGAAGGCTTG AATAAAGTGA TACGTTAGAG TAACACATAT CCTGCCTTTA CTAAAAACCT     780

ATAACATTTA ATTTTATAAA AAGTCAGGAA AGTCAGAGAA TCCTAGGTAT ATAATCACCT     840

TTTAAAAAAA TTTTTCATTT TAACTTAAAC ATAGGGATAA TGGCAAGCCA CTCATAATGT     900

TGTCATTTGA AGATCACACC TTTTAATGTA GCTGAATTTG GAAGAGAGAA GGAGAGAAAC    960

AGAAATGAGA AGGTTTGCTT AAAAAACAGA TGCCAGTGCA CAAATCTTAA AGAATTATAA    1020

GGCCTGGTGC GATGGCTCAC ACCTGTAATC CCAGCACTTT GGGAGACAGA GGTGGGCGAA    1080

TCACAAGGTC AGGAGTTCGA GACCATCCTG GCCAACATGG TGTAACCCCA TGTCTACCAA    1140

AAATACAAAA AATTAGCTGG GCATGGTGGC GGGCACCTGT AATCCCAGCT ACTGGGGAGG    1200
```

-continued

```
CTGAGGCAGG AGAATCGCCT GAGCCTGGGA GGCGGAGGTT GTAGTGAGCT GAGATCATGC      1260

CACTGCAACA AGCGTGAGAC TCCATCTCAA AAAAAAAAAA AAAAAAAAAA AAA             1313
```

(2) INFORMATION FOR SEQ ID NO:23:

(i) SEQUENCE CHARACTERISTICS:
    (A) LENGTH: 3131 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: Coding Sequence
    (B) LOCATION: 449...2665

(xi) SEQUENCE DESCRIPTION: SEQ ID NO:23:

```
GGAGAGACTA NCGGCGCTAG TGGCCCTTTA GTGGCTCTCC CGGGAGCTGA AAAATCTAAG       60

TCTCCTGACC CAGACCCTAA CTTGTCACAT GACAGGATTG TCCACATAAA TTCGATCCCT      120

ACTAATGAGA AAGCAGACCC TTTCCTGAGG TCCAGCAAGA TAATCCAGAT CTCCAGTGGC      180

AGAGAGTTGA GAGTGATCCA GGAAAGTGAA GCAGGAGATG CGGGACTGCC CCGGGTGGAA      240

GTGATCCTCG ACTGCTCTGA CAGGCAGAAG ACAGAAGGGT GCAGGCTTCA GGCAGGAAAG      300

GAGTGTGTGG ATTCTCCAGT GGAAGGAGGG CAGTCAGAAG CACCTCCTTC TCTGGTATCC      360

TTTGCCGTCT CATCAGAAGG CACAGAGCAG GGAGAAGATC CACGCTCGGA AAAAGATCAC      420

AGCAGACCTC ACAAGCACCG AGCGCGGC ATG CAC GGC TCA GGA GGA AGT GAA         472
                              Met His Gly Ser Gly Gly Ser Glu
                                1               5

AGC CTG TCA GAA AAA CAA GTG AAG GAA GCA AAA TCT AAA TGC AAA AGC        520
Ser Leu Ser Glu Lys Gln Val Lys Glu Ala Lys Ser Lys Cys Lys Ser
     10              15                  20

ATT GCC CTT CTT CTA ACG GAT GCT CCC AAC CCC AAC TCC AAG GGG GTG        568
Ile Ala Leu Leu Leu Thr Asp Ala Pro Asn Pro Asn Ser Lys Gly Val
 25              30                  35                  40

TTG ATG TTT AAG AAG CGA CGT CGG AGG GCC AGG AAA TAC ACC CTA GTT        616
Leu Met Phe Lys Lys Arg Arg Arg Arg Ala Arg Lys Tyr Thr Leu Val
             45                  50                  55

AGC TAC GGT ACT GGC GAG CTT GAG CGA GAG GCG GAC GAG GAG GAA GAA        664
Ser Tyr Gly Thr Gly Glu Leu Glu Arg Glu Ala Asp Glu Glu Glu Glu
         60                  65                  70

GGT GAC AAG GAG GAT ACA TGT GAA GTA GCA TTT CTT GGT GCA AGC GAA        712
Gly Asp Lys Glu Asp Thr Cys Glu Val Ala Phe Leu Gly Ala Ser Glu
     75                  80                  85

TCA GAG GTG GAT GAA GAG TTA TTG TCT GAC GTT GAC GAC AAC ACA CAA        760
Ser Glu Val Asp Glu Glu Leu Leu Ser Asp Val Asp Asp Asn Thr Gln
 90                  95                  100

GTT GTG AAC TTT GAC TGG GAT TCT GGA CTG GTG GAC ATT GAA AAG AAA        808
Val Val Asn Phe Asp Trp Asp Ser Gly Leu Val Asp Ile Glu Lys Lys
105                 110                 115                 120

CTG AAC AGA GGG GAC AAG ATG GAG ATG TTA CCA GAC ACC ACA GGC AAG        856
Leu Asn Arg Gly Asp Lys Met Glu Met Leu Pro Asp Thr Thr Gly Lys
                125                 130                 135

GGA GCC CTC ATG TTT GTC AAG AGG AGG GAG AGA ATG GAT CAG ATC ACA        904
Gly Ala Leu Met Phe Val Lys Arg Arg Glu Arg Met Asp Gln Ile Thr
            140                 145                 150

GCC CAA AAA GAA GAG GAC AAG GTA GGT GGA ACG CCA AGC AGA GAA CAA        952
Ala Gln Lys Glu Glu Asp Lys Val Gly Gly Thr Pro Ser Arg Glu Gln
        155                 160                 165
```

```
GAT GCT GCC CAG ACC GAT GGC CTG AGA ACC ACG ACT TCT TAC CAA AGA      1000
Asp Ala Ala Gln Thr Asp Gly Leu Arg Thr Thr Thr Ser Tyr Gln Arg
    170                 175                 180

AAG GAG GAA GAG TCG GTA AGA ACG CAG AGC TCT GTG AGC AAA AGC TAC      1048
Lys Glu Glu Glu Ser Val Arg Thr Gln Ser Ser Val Ser Lys Ser Tyr
185                 190                 195                 200

ATC GAG GTG AGT CAT GGT CTT GGC CAT GTT CCC CAA CAG AAT GGC TTC      1096
Ile Glu Val Ser His Gly Leu Gly His Val Pro Gln Gln Asn Gly Phe
                    205                 210                 215

AGT GGG GCA TCT GAG ACA GCA AAC ATC CAG AGG ATG GTC CCC ATG AAT      1144
Ser Gly Ala Ser Glu Thr Ala Asn Ile Gln Arg Met Val Pro Met Asn
                220                 225                 230

AGA ACG GCC AAA CCC TTC CCA GGG TCT GTG AAT CAG CCA GCT ACC CCC      1192
Arg Thr Ala Lys Pro Phe Pro Gly Ser Val Asn Gln Pro Ala Thr Pro
            235                 240                 245

TTC TCG CCA ACC CGA AAC ATG ACG AGT CCC ATT GCT GAC TTT CCT GCA      1240
Phe Ser Pro Thr Arg Asn Met Thr Ser Pro Ile Ala Asp Phe Pro Ala
        250                 255                 260

CCT CCA CCT TAC TCT GCA GTC ACT CCT CCC CCT GAC GCC TTC TCC AGA      1288
Pro Pro Pro Tyr Ser Ala Val Thr Pro Pro Pro Asp Ala Phe Ser Arg
265                 270                 275                 280

GGG GTT TCA AGT CCG ATT GCT GGC CCA GCA CAG CCC CCT CCA TGG CCC      1336
Gly Val Ser Ser Pro Ile Ala Gly Pro Ala Gln Pro Pro Pro Trp Pro
                    285                 290                 295

CAG CCT GCC CCG TGG TCC CAG CCA GCC TTT TAC GAT TCG TCT GAG CGA      1384
Gln Pro Ala Pro Trp Ser Gln Pro Ala Phe Tyr Asp Ser Ser Glu Arg
                300                 305                 310

ATA GCT TCC CGA GAT GAG AGG ATC TCA GTG CCA GCA AAA AGA ACA GGA      1432
Ile Ala Ser Arg Asp Glu Arg Ile Ser Val Pro Ala Lys Arg Thr Gly
            315                 320                 325

ATA TTG CAG GAG GCC AAA AGG AGA AGC ACG ACA AAA CCC ATG TTT ACT      1480
Ile Leu Gln Glu Ala Lys Arg Arg Ser Thr Thr Lys Pro Met Phe Thr
        330                 335                 340

TTT AAA GAG CCC AAA GTA AGC CCA AAT CCT GAA CTC TTG TCA CTC CTT      1528
Phe Lys Glu Pro Lys Val Ser Pro Asn Pro Glu Leu Leu Ser Leu Leu
345                 350                 355                 360

CAA AAT TCA GAA GGC AAA CGG GGC ACT GGA GCT GGA GGT GAT TCC GGA      1576
Gln Asn Ser Glu Gly Lys Arg Gly Thr Gly Ala Gly Gly Asp Ser Gly
                    365                 370                 375

CCG GAA GAA GAC TAC CTC AGC TTG GGG GCA GAG GCT TGT AAT TTC ATG      1624
Pro Glu Glu Asp Tyr Leu Ser Leu Gly Ala Glu Ala Cys Asn Phe Met
                380                 385                 390

CAA AGC TCC TCT GCC AAA CAA AAG ACC CCT CCT CCT GTT GCT CCA AAA      1672
Gln Ser Ser Ser Ala Lys Gln Lys Thr Pro Pro Pro Val Ala Pro Lys
            395                 400                 405

CCT GCA GTC AAG TCC TCA TCC TCC CAA CCA GTA ACT CCA GTT TCC CCA      1720
Pro Ala Val Lys Ser Ser Ser Ser Gln Pro Val Thr Pro Val Ser Pro
        410                 415                 420

GTC TGG TCT CCA GGA GTG GCT CCC ACC CAA CCT CCT GCC TTC CCC ACA      1768
Val Trp Ser Pro Gly Val Ala Pro Thr Gln Pro Pro Ala Phe Pro Thr
425                 430                 435                 440

TCC AAC CCA TCA AAG GGC ACC GTT GTC TCC TCC ATC AAA ATA GCC CAG      1816
Ser Asn Pro Ser Lys Gly Thr Val Val Ser Ser Ile Lys Ile Ala Gln
                    445                 450                 455

CCT TCT TAC CCT CCT GCC CGG CCT GCA AGT ACT TTG AAC GTG GCT GGT      1864
Pro Ser Tyr Pro Pro Ala Arg Pro Ala Ser Thr Leu Asn Val Ala Gly
                460                 465                 470

CCC TTC AAA GGA CCA CAA GCA GCA GTA GCC AGT CAG AAT TAC ACA CCC      1912
Pro Phe Lys Gly Pro Gln Ala Ala Val Ala Ser Gln Asn Tyr Thr Pro
            475                 480                 485
```

```
AAA CCA ACA GTT TCC ACA CCA ACA GTC AAT GCT GTT CAG CCT GGT GCA    1960
Lys Pro Thr Val Ser Thr Pro Thr Val Asn Ala Val Gln Pro Gly Ala
        490                 495                 500

GTG GGA CCA TCC AAT GAG CTT CCA GGA ATG AGT GGG AGA GGA GCT CAG    2008
Val Gly Pro Ser Asn Glu Leu Pro Gly Met Ser Gly Arg Gly Ala Gln
505                 510                 515                 520

CTC TTT GCT AAA AGG CAG TCG AGA ATG GAG AAG TAT GTG GTC GAT TCA    2056
Leu Phe Ala Lys Arg Gln Ser Arg Met Glu Lys Tyr Val Val Asp Ser
                525                 530                 535

GAC ACG GTG CAG GCC CAC GCT GCT CGA GCT CAG TCT CCC ACT CCA TCT    2104
Asp Thr Val Gln Ala His Ala Ala Arg Ala Gln Ser Pro Thr Pro Ser
            540                 545                 550

CTC CCG GCC AGT TGG AAG TAC TCC TCC AAT GTC CGA GCA CCT CCT CCT    2152
Leu Pro Ala Ser Trp Lys Tyr Ser Ser Asn Val Arg Ala Pro Pro Pro
        555                 560                 565

GTG GCC TAT AAT CCT ATC CAC TCG CCG TCT TAC CCA CTG GCT GCT CTC    2200
Val Ala Tyr Asn Pro Ile His Ser Pro Ser Tyr Pro Leu Ala Ala Leu
    570                 575                 580

AAG TCT CAG CCA TCA GCT GCA CAG CCC TCC AAA ATG GGC AAG AAA AAG    2248
Lys Ser Gln Pro Ser Ala Ala Gln Pro Ser Lys Met Gly Lys Lys Lys
585                 590                 595                 600

GGA AAG AAA CCC CTC AAT GCA TTA GAT GTC ATG AAG CAC CAA CCG TAT    2296
Gly Lys Lys Pro Leu Asn Ala Leu Asp Val Met Lys His Gln Pro Tyr
                605                 610                 615

CAG CTC AAT GCA TCC TTG TTT ACT TTC CAA CCT CCA GAT GCA AAG GAT    2344
Gln Leu Asn Ala Ser Leu Phe Thr Phe Gln Pro Pro Asp Ala Lys Asp
            620                 625                 630

GGC CTC CCC CAG AAG TCA TCA GTC AAG GTC AAT TCA GCC CTG GCC ATG    2392
Gly Leu Pro Gln Lys Ser Ser Val Lys Val Asn Ser Ala Leu Ala Met
        635                 640                 645

AAG CAA GCT CTT CCT CCC CGG CCA GTG AAT GCT GCC TCA CCT ACG AAT    2440
Lys Gln Ala Leu Pro Pro Arg Pro Val Asn Ala Ala Ser Pro Thr Asn
    650                 655                 660

GTG CAG GCT TCG TCA GTG TAC TCG GTA CCA GCC TAT ACC TCT CCT CCT    2488
Val Gln Ala Ser Ser Val Tyr Ser Val Pro Ala Tyr Thr Ser Pro Pro
665                 670                 675                 680

TCC TTC TTT GCA GAG GCC TCC TCA CCA GTC AGT GCA TCC CCA GTG CCT    2536
Ser Phe Phe Ala Glu Ala Ser Ser Pro Val Ser Ala Ser Pro Val Pro
                685                 690                 695

GTG GGC ATT CCC ACC TCG CCA AAG CAA GAA TCA GCC TCA TCA TCT TAT    2584
Val Gly Ile Pro Thr Ser Pro Lys Gln Glu Ser Ala Ser Ser Ser Tyr
            700                 705                 710

TTT GTG GCA CCA AGG CCA AAG TTC TCA GCC AAG AAA AGT GGT GTC ACA    2632
Phe Val Ala Pro Arg Pro Lys Phe Ser Ala Lys Lys Ser Gly Val Thr
        715                 720                 725

ATT CAG GTG TGG AAA CCA TCT GTT GTG GAA GAG TAATCTTGTA GCTGAAGCTG  2685
Ile Gln Val Trp Lys Pro Ser Val Val Glu Glu
    730                 735

AGTGTCCACT TTGCTTGAAA TGAATTGTTT GCAGTGTTTC TTGAGTCCCT GAGAATGCCT  2745

AGCAAAGTCC TCAACTTACT TAATTTCAGA TATGTCACCT CCTAATCTGG GTCCAAGGAG  2805

TATAATATTT TTAATGAGTC AAAAATCCAA CTCAGATTGA CCTAAAATAT ATTTATCTTC  2865

TTTGCACACT TAAAAAATCC AGGAGCACCC CAAAATAGAC ATGTACCGTT ATATTAAGTA  2925

AGCAGGAGAC TTAGGATTTG TGCTGTAGCC ACAAGAAAGA CAGTGATCAG TGATATCAAA  2985

CATCAGGAAT CAGCCTTTAT GTAACATAAC AGCTGTCCTC CTATGGTGAA AGGTTCAAAT  3045

GTAGTGAAGG TATAACSTAT ATTGACTGAG ATTTCCCTTT TAGGTAGTGC CTTATCTCTA  3105
```

```
TTACTAGTGT TAAAGGAGGG GGGGCC                                                    3131
```

(2) INFORMATION FOR SEQ ID NO:24:

(i) SEQUENCE CHARACTERISTICS:
        (A) LENGTH: 739 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:24:

```
Met His Gly Ser Gly Gly Ser Glu Ser Leu Ser Glu Lys Gln Val Lys
 1               5                  10                  15

Glu Ala Lys Ser Lys Cys Lys Ser Ile Ala Leu Leu Leu Thr Asp Ala
            20                  25                  30

Pro Asn Pro Asn Ser Lys Gly Val Leu Met Phe Lys Lys Arg Arg Arg
        35                  40                  45

Arg Ala Arg Lys Tyr Thr Leu Val Ser Tyr Gly Thr Gly Glu Leu Glu
50                  55                  60

Arg Glu Ala Asp Glu Glu Glu Gly Asp Lys Glu Asp Thr Cys Glu
65                  70                  75                  80

Val Ala Phe Leu Gly Ala Ser Glu Ser Glu Val Asp Glu Leu Leu
                85                  90                  95

Ser Asp Val Asp Asp Asn Thr Gln Val Val Asn Phe Asp Trp Asp Ser
                100                 105                 110

Gly Leu Val Asp Ile Glu Lys Lys Leu Asn Arg Gly Asp Lys Met Glu
            115                 120                 125

Met Leu Pro Asp Thr Thr Gly Lys Gly Ala Leu Met Phe Val Lys Arg
        130                 135                 140

Arg Glu Arg Met Asp Gln Ile Thr Ala Gln Lys Glu Asp Lys Val
145                 150                 155                 160

Gly Gly Thr Pro Ser Arg Glu Gln Asp Ala Ala Gln Thr Asp Gly Leu
                165                 170                 175

Arg Thr Thr Thr Ser Tyr Gln Arg Lys Glu Glu Glu Ser Val Arg Thr
                180                 185                 190

Gln Ser Ser Val Ser Lys Ser Tyr Ile Glu Val Ser His Gly Leu Gly
            195                 200                 205

His Val Pro Gln Gln Asn Gly Phe Ser Gly Ala Ser Glu Thr Ala Asn
        210                 215                 220

Ile Gln Arg Met Val Pro Met Asn Arg Thr Ala Lys Pro Phe Pro Gly
225                 230                 235                 240

Ser Val Asn Gln Pro Ala Thr Pro Phe Ser Pro Thr Arg Asn Met Thr
                245                 250                 255

Ser Pro Ile Ala Asp Phe Pro Ala Pro Pro Tyr Ser Ala Val Thr
                260                 265                 270

Pro Pro Pro Asp Ala Phe Ser Arg Gly Val Ser Ser Pro Ile Ala Gly
            275                 280                 285

Pro Ala Gln Pro Pro Trp Pro Gln Pro Ala Pro Trp Ser Gln Pro
        290                 295                 300

Ala Phe Tyr Asp Ser Ser Glu Arg Ile Ala Ser Arg Asp Glu Arg Ile
305                 310                 315                 320

Ser Val Pro Ala Lys Arg Thr Gly Ile Leu Gln Glu Ala Lys Arg Arg
                325                 330                 335
```

-continued

```
Ser Thr Thr Lys Pro Met Phe Thr Phe Lys Glu Pro Lys Val Ser Pro
            340                 345                 350
Asn Pro Glu Leu Leu Ser Leu Leu Gln Asn Ser Glu Gly Lys Arg Gly
            355                 360                 365
Thr Gly Ala Gly Gly Asp Ser Gly Pro Glu Glu Asp Tyr Leu Ser Leu
            370                 375                 380
Gly Ala Glu Ala Cys Asn Phe Met Gln Ser Ser Ala Lys Gln Lys
385                 390                 395                 400
Thr Pro Pro Pro Val Ala Pro Lys Pro Ala Val Lys Ser Ser Ser
                    405                 410                 415
Gln Pro Val Thr Pro Val Ser Pro Val Trp Ser Pro Gly Val Ala Pro
            420                 425                 430
Thr Gln Pro Pro Ala Phe Pro Thr Ser Asn Pro Ser Lys Gly Thr Val
            435                 440                 445
Val Ser Ser Ile Lys Ile Ala Gln Pro Ser Tyr Pro Pro Ala Arg Pro
            450                 455                 460
Ala Ser Thr Leu Asn Val Ala Gly Pro Phe Lys Gly Pro Gln Ala Ala
465                 470                 475                 480
Val Ala Ser Gln Asn Tyr Thr Pro Lys Pro Thr Val Ser Thr Pro Thr
                    485                 490                 495
Val Asn Ala Val Gln Pro Gly Ala Val Gly Pro Ser Asn Glu Leu Pro
                    500                 505                 510
Gly Met Ser Gly Arg Gly Ala Gln Leu Phe Ala Lys Arg Gln Ser Arg
            515                 520                 525
Met Glu Lys Tyr Val Val Asp Ser Asp Thr Val Gln Ala His Ala Ala
            530                 535                 540
Arg Ala Gln Ser Pro Thr Pro Ser Leu Pro Ala Ser Trp Lys Tyr Ser
545                 550                 555                 560
Ser Asn Val Arg Ala Pro Pro Val Ala Tyr Asn Pro Ile His Ser
                    565                 570                 575
Pro Ser Tyr Pro Leu Ala Ala Leu Lys Ser Gln Pro Ser Ala Ala Gln
            580                 585                 590
Pro Ser Lys Met Gly Lys Lys Gly Lys Lys Pro Leu Asn Ala Leu
            595                 600                 605
Asp Val Met Lys His Gln Pro Tyr Gln Leu Asn Ala Ser Leu Phe Thr
            610                 615                 620
Phe Gln Pro Pro Asp Ala Lys Asp Gly Leu Pro Gln Lys Ser Ser Val
625                 630                 635                 640
Lys Val Asn Ser Ala Leu Ala Met Lys Gln Ala Leu Pro Arg Pro
                    645                 650                 655
Val Asn Ala Ala Ser Pro Thr Asn Val Gln Ala Ser Ser Val Tyr Ser
                    660                 665                 670
Val Pro Ala Tyr Thr Ser Pro Pro Ser Phe Phe Ala Glu Ala Ser Ser
            675                 680                 685
Pro Val Ser Ala Ser Pro Val Pro Val Gly Ile Pro Thr Ser Pro Lys
            690                 695                 700
Gln Glu Ser Ala Ser Ser Tyr Phe Val Ala Pro Arg Pro Lys Phe
705                 710                 715                 720
Ser Ala Lys Lys Ser Gly Val Thr Ile Gln Val Trp Lys Pro Ser Val
                    725                 730                 735
Val Glu Glu
```

COMPOSITIONS AND METHODS FOR THE DIAGNOSIS, PREVENTION, AND TREATMENT OF NEOPLASTIC CELL GROWTH AND PROLIFERATION

CROSS REFERENCE TO RELATED APPLICATIONS

This application claims priority from provisional application Ser. No. 60/013,438, filed on Mar. 15, 1996.

1. BACKGROUND OF THE INVENTION

The present invention relates to methods and compositions for the diagnosis, prevention, and treatment of neoplastic cell growth and proliferation, i.e., tumors and cancers (e.g., colon cancer) in mammals, for example, humans. Specifically, genes which are differentially expressed in tumor cells relative to normal cells are identified. Among these are certain novel genes.

Malignant tumors, i.e., cancers, are the second leading cause of death in the United States, after heart disease (Boring, et al., *CA Cancer J. Clin.*, 43:7, 1993), and develop in one in three Americans. One of every four Americans dies of cancer. Cancer is characterized primarily by an increase in the number of abnormal, or neoplastic, cells derived from a normal tissue which proliferate to form a tumor mass, the invasion of adjacent tissues by these neoplastic tumor cells, and the generation of malignant cells which spread via the blood or lymphatic system to regional lymph nodes and to distant sites. The latter progression to malignancy is referred to as metastasis.

Cancer can result from a breakdown in the communication between neoplastic cells and their environment, including their normal neighboring cells. Signals, both growth-stimulatory and growth-inhibitory, are routinely exchanged between cells within a tissue. Normally, cells do not divide in the absence of stimulatory signals, and, likewise, will cease dividing in the presence of inhibitory signals. In a cancerous, or neoplastic, state, a cell acquires the ability to "override" these signals and to proliferate under conditions in which normal cells would not grow.

Tumor cells must acquire a number of distinct aberrant traits to proliferate. Reflecting this requirement is the fact that the genomes of certain well-studied tumors carry several different independently altered genes, including activated oncogenes and inactivated tumor suppressor genes. Each of these genetic changes appears to be responsible for imparting some of the traits that, in aggregate, represent the full neoplastic phenotype (Land et al., *Science*, 222:771, 1983; Ruley, *Nature*, 304:602, 1983; Hunter, *Cell*, 64:249, 1991).

Differential expression of the following suppressor genes has been demonstrated in human cancers: a retinoblastoma gene, RB; the Wilms' tumor gene, WT1 (11p); a gene deleted in colon carcinoma, DCC (18q); the neurofibromatosis type 1 gene, NF1 (17q); and a gene involved in familial adenomatous polyposis coli, APC (5q) (Vogelstein, B. and Kinzler, K. W., *Trends Genet.*, 9:138–141, 1993).

2. SUMMARY OF THE INVENTION

The present invention relates to methods and compositions for the diagnosis, prevention, and treatment of tumors and cancers, e.g., colon or lung cancer, in mammals, e.g., humans. The invention is based on the discovery of genes that are differentially expressed in tumor cells relative to normal cells of the same tissue. The genes identified can be used diagnostically or as targets for therapy, and can be used to identify compounds useful in the diagnosis, prevention, and therapy of tumors and cancers (e.g., colon cancer). The genes also can be used in gene therapy, protein synthesis, and to develop antisense nucleic acids.

In general, the invention features an isolated nucleic acid including the nucleotide sequence of any one of SEQ ID NOS: 1, 3 to 7, 9 to 13, 16, 17, or 19 to 23, or an isolated nucleic acid that hybridizes under stringent hybridization conditions to one of these nucleic acids or their complements. The invention also features a genetically engineered host cell containing one of these nucleotide sequences, and an expression vector containing one of these nucleotide sequences operably linked to a nucleotide sequence regulatory element that controls expression of the nucleotide sequence in a host cell.

The invention further features a substantially pure gene product encoded by one of these nucleic acids, e.g., having the amino acid sequence of SEQ ID NO:18. The invention also features an antibody that immunospecifically binds to this gene product.

In another embodiment, the invention features a method of diagnosing a tumor in a mammal by obtaining a test sample of tissue cells, e.g., colon cells, from the mammal; obtaining a control sample of known normal cells from the same type of tissue; and detecting in both the test sample and the control sample the level of expression of any one or more of genes 048, 083, 090, 093, and 097, wherein a level of expression higher in the test sample than in the control sample indicates a tumor in the test sample.

The method of diagnosing a tumor can also be carried out using any one or more of genes 029, 030, 036, 038, 056, 075, 082, 092, 096, or 101, wherein a level of expression lower in the test sample than in the control sample indicates a tumor in the test sample.

The invention further features a method of treating a tumor, e.g., a colon tumor, in a patient, e.g., a mammal such as a human, by administering to the mammal a compound in an amount effective to decrease the level of expression or activity of the gene transcript or gene product of any one or more of genes 048, 083, 090, 093, and 097, to a level effective to treat the tumor.

In this method, the compound can be an antisense or ribozyme molecule that blocks translation of the gene transcript, or a nucleic acid complementary to the 5' region of any one or more of genes 048, 083, 090, 093, and 097, and blocks formation of a gene transcript via triple helix formation. The compound also can be an antibody that neutralizes the activity of the gene product.

In another method of treating a tumor in a mammal, a compound is administered in an amount effective to increase the level of expression or activity of the gene transcript or gene product of any one or more of genes 029, 030, 036, 038, 056, 075, 082, 092, 096, and 101, to a level effective to treat the tumor, e.g., colon tumor. In this method, the compound can be a nucleic acid whose administration results in an increase in the level of expression of any one of genes 029, 030, 036, 038, 056, 075, 082, 092, 096, and 101, thereby ameliorating symptoms of the tumor.

In another aspect, the invention features a method for inhibiting tumors in a mammal by administering to the mammal a normal allele of one or more of genes 029, 030, 036, 038, 056, 075, 082, 092, 096, and 101, so that a gene product is expressed, thereby inhibiting tumors. The invention also covers a method for treating tumors in a mammal by administering to the mammal an effective amount of a gene product of any one or more of genes 029, 030, 036, 038, 056, 075, 082, 092, 096, and 101.

The invention also features a method of monitoring the efficacy of a compound in clinical trials for inhibition of tumors, e.g., colon tumors, in a patient by obtaining a first sample of tumor tissue cells from the patient; administering the compound to the patient; after a time sufficient for the compound to inhibit the tumor, obtaining a second sample of tumor tissue cells from the patient; and detecting in the first and second samples the level of expression of any one or more of genes 048, 083, 090, 093, and 097, wherein a level of expression lower in the second sample than in the first sample indicates that the compound is effective to inhibit a tumor in the patient.

This method can also be carried out using any one or more of genes 029, 030, 036, 038, 056, 075, 082, 092, 096, or 101, wherein a level of expression higher in the second sample than in the first sample indicates that the compound is effective to inhibit a tumor in the patient.

A "tumor," as used herein, refers to all neoplastic cell growth and proliferation, whether malignant or benign, and all precancerous and cancerous cells and tissues.

A "differentially expressed" gene transcript, as used herein, refers to a gene transcript that is found in different numbers of copies, or in activated versus inactivated states, in different cell or tissue types of an organism having a tumor or cancer, e.g., colon cancer, compared to the numbers of copies or state of the gene transcript found in the cells of the same tissue in a healthy organism, or in the cells of the same tissue in the same organism. Multiple copies of gene transcripts may be found in an organism having the tumor or cancer, while only one, or significantly fewer copies, of the same gene transcript are found in a healthy organism or healthy cells of the same tissue in the same organism, or vice-versa.

As used herein, a "differentially expressed gene" refers to (a) a gene containing: at least one of the DNA sequences disclosed herein (as shown in FIGS. 1a to 1p and 2 to 7); (b) any DNA sequence that encodes the amino acid sequences encoded by the DNA sequences disclosed in FIGS. 1a to 1p and 2 to 7; or (c) any DNA sequence that hybridizes to the complement of the sequences disclosed in FIGS. 1a to 1p and 2 to 7 under highly stringent conditions, i.e., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, *Current Protocols in Molecular Biology*, Vol. I, Green Publishing Associates, Inc., and John Wiley & sons, Inc., New York, at p. 2.10.3); or under moderately stringent conditions, i.e., washing in 0.2×SSC/0.1% SDS at 42° C. (Ausubel et al., 1989, supra), yet which still encodes a gene product functionally equivalent to a gene product encoded by a gene of (a) above.

The initial cDNA sequences discovered by the paradigms described below (and shown in FIGS. 1a to 1p) are used to obtain additional cDNA sequences of various lengths up to the full-length cDNA sequences corresponding to individual genes (see FIGS. 2 to 7). The individual genes are referred to by a three digit number, e.g., 029, based on the number of the first DNA sequence found that corresponds to that particular gene. In some instances, the paradigm generated two or more DNA sequences that correspond to overlapping or completely unique portions of the full-length cDNA of a gene. In those instances, the gene is referred to by the number of the first DNA sequence found to correspond to that gene, followed by one or more numbers in parentheses that correspond to the numbers of later sequences that correspond to the same gene.

A "differentially expressed gene," can be a target, fingerprint, or pathway gene. For example, a "fingerprint gene," as used herein, refers to a differentially expressed gene whose expression pattern can be used as a prognostic or diagnostic marker for the evaluation of tumors and cancers, or which can be used to identify compounds useful for the treatment of tumors and cancers, e.g., colon or lung cancer. For example, the effect of a compound on the fingerprint gene expression pattern normally displayed in connection with tumors and cancers can be used to evaluate the efficacy of the compound as a tumor and cancer treatment, or can be used to monitor patients undergoing clinical evaluation for the treatment of tumors and cancer.

A "fingerprint pattern," as used herein, refers to a pattern generated when the expression pattern of a series (which can range from two up to all the fingerprint genes that exist for a given state) of fingerprint genes is determined. A fingerprint pattern can be used in the same diagnostic, prognostic, and compound identification methods as the expression of a single fingerprint gene.

A "target gene," as used herein, refers to a differentially expressed gene in which modulation of the level of gene expression or of gene product activity prevents and/or ameliorates tumor and cancer, e.g., colon cancer, symptoms. Thus, compounds that modulate the expression of a target gene or the activity of a target gene product can be used in the treatment or prevention of tumors and cancers.

"Pathway genes," as used herein, are genes that encode proteins or polypeptides that interact with other gene products involved in tumors and cancers. Pathway genes can also exhibit target gene and/or fingerprint gene characteristics.

By "substantially identical" is meant a polypeptide or nucleic acid having a sequence that has at least 85%, preferably 90%, and more preferably 95%, 98%, 99% or more identity to the sequence of a reference nucleic acid sequence, e.g., the nucleic acid sequence of SEQ ID NO:23.

The nucleic acid molecules of the invention can be inserted into transcription and/or translation vectors, as described below, which will facilitate expression of the insert. The nucleic acid molecules and the polypeptides they encode can be used directly as diagnostic or therapeutic agents, or (in the case of a polypeptide) can be used to generate antibodies that, in turn, are therapeutically useful. Accordingly, expression vectors containing the nucleic acid molecules of the invention, cells transfected with these vectors, the polypeptides expressed, and antibodies generated, against either the entire polypeptide or an antigenic fragment thereof, are among the preferred embodiments.

As used herein, the term "transfected cell" means any cell into which (or into an ancestor of which) has been introduced, by means of recombinant DNA techniques, a nucleic acid encoding a polypeptide of the invention.

By "isolated nucleic acid molecule" is meant a nucleic acid molecule that is separated from the 5' and 3' coding sequences with which it is immediately contiguous in the naturally occurring genome of an organism. Thus, the term "isolated nucleic acid molecule" includes nucleic acid molecule which are not naturally occurring, e.g., nucleic acid molecules created by recombinant DNA techniques.

The term "nucleic acid molecule" encompasses both RNA and DNA, including cDNA, genomic DNA, and synthetic (e.g., chemically synthesized) DNA. Where single-stranded, the nucleic acid may be a sense strand or an antisense strand.

The polypeptides of the invention can also be chemically synthesized, or they can be purified from tissues in which they are naturally expressed, according to standard biochemical methods of purification.

Also included in the invention are "functional polypeptides," which possess one or more of the biological functions or activities of a protein or polypeptide of the invention. These functions or activities include the ability to bind some or all of the proteins which normally bind to gene 036 protein.

The functional polypeptides may contain a primary amino acid sequence that has been modified from those disclosed herein. Preferably these modifications consist of conservative amino acid substitutions, as described herein.

The terms "protein" and "polypeptide" are used herein to describe any chain of amino acids, regardless of length or post-translational modification (for example, glycosylation or phosphorylation). Thus, the term "polypeptide" includes full-length, naturally occurring proteins as well as recombinantly or synthetically produced polypeptides that correspond to a full-length naturally occurring protein or to particular domains or portions of a naturally occurring protein. The term also encompasses mature proteins which have an added amino-terminal methionine to facilitate expression in prokaryotic cells).

The term "purified" as used herein refers to a nucleic acid or peptide that is substantially free of cellular material, viral material, or culture medium when produced by recombinant DNA techniques, or chemical precursors or other chemicals when chemically synthesized.

Polypeptides or other compounds of interest are said to be "substantially pure" when they are within preparations that are at least 60% by weight (dry weight) the compound of interest. Preferably, the preparation is at least 75%, more preferably at least 90%, and most preferably at least 99%, by weight the compound of interest. Purity can be measured by any appropriate standard method, for example, by column chromatography, polyacrylamide gel electrophoresis, or HPLC analysis.

A polypeptide or nucleic acid molecule is "substantially identical" to a reference polypeptide or nucleic acid molecule if it has a sequence that is at least 85%, preferably at least 90%, and more preferably at least 95%, 98%, or 99% identical to the sequence of the reference polypeptide or nucleic acid molecule.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. of course, many other polypeptides will meet the same criteria.

In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

For polypeptides, the length of the reference polypeptide sequence will generally be at least 16 amino acids, preferably at least 20 amino acids, more preferably at least 25 amino acids, and most preferably 35 amino acids, 50 amino acids, or 100 amino acids. For nucleic acids, the length of the reference nucleic acid sequence will generally be at least 50 nucleotides, preferably at least 60 nucleotides, more preferably at least 75 nucleotides, and most preferably 100 nucleotides or 300 nucleotides.

Sequence identity can be measured using sequence analysis software (for example, the Sequence Analysis Software Package of the Genetics Computer Group, University of Wisconsin Biotechnology Center, 1710 University Avenue, Madison, Wis. 53705), with the default parameters as specified therein.

The nucleic acid molecules of the invention can be inserted into a vector, as described below, which will facilitate expression of the insert. The nucleic acid molecules and the polypeptides they encode can be used directly as diagnostic or therapeutic agents, or can be used (directly in the case of the polypeptide or indirectly in the case of a nucleic acid molecule) to generate antibodies that, in turn, are clinically useful as a therapeutic or diagnostic agent. Accordingly, vectors containing the nucleic acid of the invention, cells transfected with these vectors, the polypeptides expressed, and antibodies generated, against either the entire polypeptide or an antigenic fragment thereof, are among the preferred embodiments.

As used herein, the term "transformed cell" means a cell into which (or into an ancestor of which) has been introduced, by means of recombinant DNA techniques, a nucleic acid molecule encoding a polypeptide of the invention.

The invention also features antibodies, e.g., monoclonal, polyclonal, and engineered antibodies, which specifically bind proteins and polypeptides of the invention, e.g., gene 036 protein. By "specifically binds" is meant an antibody that recognizes and binds to a particular antigen, e.g., a gene 036 polypeptide of the invention, but which does not substantially recognize or bind to other molecules in a sample, e.g., a biological sample.

The invention also features antagonists and agonists of gene 036 protein that can inhibit or enhance one or more of the functions or activities of gene 036 protein or other proteins of the invention, respectively. Suitable antagonists can include small molecules (i.e., molecules with a molecular weight below about 500), large molecules (i.e., molecules with a molecular weight above about 500), antibodies that bind and "neutralize" gene 036 protein (as described below), polypeptides which compete with a native form of gene 036 protein for binding to a protein which naturally interacts with gene 036 protein, and nucleic acid molecules that interfere with transcription of a gene of the invention (for example, antisense nucleic acid molecules and ribozymes). Useful agonists also include small and large molecules, and antibodies other than "neutralizing" antibodies.

The invention also features molecules which can increase or decrease the expression of a gene of the invention (e.g., by influencing transcription or translation). Small molecules (i.e., molecules with a molecular weight below about 500), large molecules (i.e., molecules with a molecular weight above about 500), and nucleic acid molecules that can be used to inhibit the expression of a gene of the invention for example, antisense and ribozyme molecules) or to enhance their expression (for example, expression constructs that place nucleic acid sequences encoding proteins of the invention, e.g., gene 036 protein under the control of a strong promoter system), and transgenic animals that express a gene 036 transgene.

The invention also includes nucleic acid molecules, preferably DNA, that hybridize to the DNA sequences (a) through (c), above, of a differentially expressed gene. Hybridization conditions can be highly stringent or moderately stringent, as described above. In instances wherein the nucleic acid molecules are deoxyoligonucleotides ("oligos"), highly stringent conditions are defined as washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules can act as target gene antisense molecules, useful in target gene regulation, or as antisense primers in amplification reactions of target, fingerprint, and/or pathway gene nucleic acid sequences. Further, such sequences can be used as part of ribozyme and/or triple helix sequences, also useful for target gene regulation. Still further, such molecules can be used in diagnostic methods to detect tumors and cancers, e.g., colon cancer, and a patient's predisposition towards tumors or cancers.

The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, "regulatory elements" include, but are not limited to, inducible and non-inducible promoters, enhancers, operators, and other elements known to those skilled in the art that drive and regulate expression. The invention includes fragments of any of the DNA sequences disclosed herein.

A "detectable" RNA expression level, as used herein, means a level that is detectable by the standard techniques of differential display, RT (reverse transcriptase)-coupled polymerase chain reaction (PCR), Northern, and/or RNase protection analyses. The degree to which expression differs need only be large enough to be visualized via standard characterization techniques, such as, for example, the differential display technique described below.

Based on the expression patterns in the paradigm results described below (e.g., Table 1), the following genes 029, 030, 036 (095), 038 (102), 056, 075, 082, 092, 096 (105), and 101 are expressed at a higher level in normal colon tissues than in cancerous colon tissues. Specifically, the data show a correlation between an increase in the expression level of these genes and a decrease in a colon cell's tumor potential. In other words, a reduction of the expression level of these genes in a cell may induce or predispose the cell to become cancerous. Hence, methods that increase the level of expression of these genes may inhibit or slow the progression to tumors and cancers, e.g., colon cancer.

On the other hand, further based on the expression patterns in the paradigm results described below (e.g., Table 1), the following genes 048, 083, 090, 093, and 097 are expressed at a higher level in colon tumor tissues than in normal colon tissues. Specifically, the data show a correlation between an increase in the expression level of these genes and an increase in a colon cell's cancer potential. In other words, a reduction of the expression level of these genes in a cell may induce or predispose that cell to remain normal. Hence, methods that decrease the level of expression of these genes may inhibit or slow the progression to tumors and cancers, e.g., colon cancer.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

3. BRIEF DESCRIPTION OF THE DRAWINGS

FIGS. 1a to 1p are a series of DNA sequence fragments (SEQ ID NOs:1 to 16) from genes detected by the paradigms described herein.

FIG. 2 is a DNA sequence (SEQ ID NO:17) from gene 082 and the amino acid sequence (SEQ ID NO:18) encoded by gene 082.

FIG. 3 is a DNA sequence (SEQ ID NO:19) from gene 048.

FIG. 4 is a DNA sequence (SEQ ID NO:20) from gene 090.

FIG. 5 is a DNA sequence (SEQ ID NO:21) from gene 093.

FIG. 6 is a DNA sequence (SEQ ID NO:22) from gene 101.

FIG. 7 is the DNA (SEQ ID NO:23) of a gene 036 cDNA and the amino acid sequence (SEQ ID NO:24) encoded by the gene 036 cDNA.

4. DETAILED DESCRIPTION

This invention is based, in part, on systematic search strategies involving a biological specimen paradigm of tumors and cancers, coupled with sensitive and high-throughput gene expression assays, to identify genes differentially expressed in tumor cells relative to normal cells of the same organ or tissue (either within the same individual, or in different organisms, one with a tumor and other healthy). In contrast to approaches that merely evaluate the expression of a given gene product presumed to play a role in one or another type of cancer, the search strategies and assays used herein permit the identification of all genes, whether known or novel, that are differentially expressed in tumor cells relative to normal cells. Further, the method is independent of gene copy number, and thus allows detection of even low copy number genes that are differentially expressed.

This comprehensive approach and evaluation permits the discovery of novel genes and gene products, as well as the identification of an array of genes and gene products (whether novel or known) involved in novel pathways that play a major role in tumor pathology. Thus, the present invention allows the identification and characterization of targets useful for prognosis, diagnosis, monitoring, rational drug design, and/or other therapeutic intervention of tumors and cancers.

The Examples below demonstrate the successful use of search strategies of the invention to identify genes that are differentially expressed in colon tumor cells relative to normal colon cells. These genes, referred to herein by different numbers, include novel and known genes which are expressed at a many-fold higher or lower level in tumor cells relative to their expression in normal cells of same tissue.

4.1. Identification of Differentially Expressed Genes

There exist a number of levels or stages at which the differential expression of differentially expressed genes can be exhibited. For example, differential expression can occur in tumor cells versus normal cells, or in tumor cells in different stages of progression. For example, genes can be identified that are differentially expressed in pre-neoplastic versus neoplastic cells. Such genes can, for example, promote unhindered cell proliferation or tumor cell invasion of adjacent tissue, both of which are viewed as hallmarks of the neoplastic state. Further, differential expression can occur among cells within any one of different states, e.g., pre-neoplastic, neoplastic, and metastatic, and can indicate, for example, a difference in severity or aggressiveness of one cell relative to that of another cell within the same state.

4.1.1. Paradigms for the Identification of Differentially Expressed Genes

Different paradigms can be used to identify particular genes. One such paradigm, referred to herein as the "specimen paradigm," uses surgical and biopsy samples. For example, such samples can represent normal colon tissue or primary, secondary, or metastasized colon tumor tissue obtained from patients having undergone surgical treatment for colon cancer.

Surgical samples can be procured under standard conditions involving freezing and storing in liquid nitrogen (see, for example, Karmali et al., *Br. J. Cancer*, 48:689–696, 1983). RNA from sample cells is isolated by, for example, differential centrifugation of homogenized tissue, and analyzed for differential expression relative to other specimen cells, preferably cells obtained from the same patient.

In another paradigm, referred to herein as the "in vitro" paradigm, cell lines, rather than tissue samples, can be used to identify genes that are differentially expressed in tumors and cancers (e.g., lung or colon cancer). Differentially expressed genes are detected, by comparing the pattern of gene expression between experimental and control conditions. In such a paradigm, genetically matched colon tumor and normal colon cell lines, e.g., variants of the same cell line, are used, one. of which exhibits a tumorous phenotype, while the other exhibits a normal colon cell phenotype.

In accordance with this aspect of the invention, the sample cells are harvested, and RNA is isolated and analyzed for differentially expressed genes, as described in detail in Section 4.1.2. Examples of cell lines that can be used in the in vitro paradigm include but are not limited to variants of human colon cell lines, such as, for example Caco-2 (ATCC HTB-37), a human colon adenocarcinoma cell line, and HT-29 (ATCC HTB-38), a moderately well-differentiated grade II human colon adenocarcinoma cell line.

In a third paradigm, referred to herein as the in viva paradigm, animal models of tumors and cancers (e.g., colon cancer) can be used to discover differentially expressed gene sequences. The in vivo nature of such models can prove to be especially predictive of the analogous responses in patients. A variety of tumor and cancer animal models can be used in the in vivo paradigms. For example, animal models of colon cancer can be generated by passaging tumor cells in animals, e.g., mice, leading to the appearance of tumors within these animals. See, e.g., the description of an orthotopic transplant model of human colon cancer in nude mice in Wang et al., *Cancer Research*, 54:4726–4728 (1994) and Togo et al., *Cancer Research*, 55:681–684 (1995). This mouse model is based on the so-called "METAMOUSE™" sold by AntiCancer, Inc. (San Diego, Calif.).

Additional animal models, some of which may exhibit differing tumor and cancer characteristics, can be generated from the original animal models described above. For example, the tumors that arise in the original animals can be removed and grown in vitro. Cells from these in vitro cultures can then be passaged in animals, and tumors resulting from this passage can be isolated. RNA from pre-passage cells, and cells isolated after one or more rounds of passage can be isolated and analyzed for differential expression. Such passaging techniques can use any known tumor or cancer cell lines. Additionally, animal models for tumors and cancers that can be used in the in vivo paradigm include any of the animal models described in Section 4.7.1.

Compounds known to have an ameliorative effect on tumor and cancer (e.g., colon cancer) symptoms, e.g., alkylating agents such as semustine (N-(2-chloroethyl)-N'-4-methylcyclohexyl)-N-nitrosourea) and lomustine (N-(2-chloroethyl)-N'-cyclohexyl-N-nitrosourea (CCNU)), also can be used in the paradigms to detect differentially expressed genes. For example, tumor cells that are cultured can be exposed to one of these compounds and analyzed for differential gene expression with respect to untreated tumor cells, according to the methods described below in Section 4.1.2. In principle, however, according to the paradigm, any cell type involved in a tumor or cancer can be treated by these compounds at any stage of the tumor process.

Cells involved in tumors and cancers can also be compared to unrelated cells, e.g., fibroblasts, that have been treated with the compound, such that any generic effects on gene expression that might not be related to the disease or its treatment can be identified. Such generic effects might be manifest, for example, by changes in gene expression that are common to the test cells and the unrelated cells upon treatment with the compound.

By these methods, the genes and gene products upon which these compounds act can be identified and used in the assays described below to identify novel therapeutic compounds for inhibition and treatment of tumors and cancers (e.g., colon cancer).

4.1.2. Analysis of Paradigm Material

To identify differentially expressed genes, total RNA is isolated from cells utilized in the paradigms described above. Any RNA isolation technique that does not select against the isolation of mRNA can be utilized for the purification of such RNA samples. See, for example, Ausubel, F. M. et al., eds., *Current Protocols in Molecular Bioloqy*, John Wiley & Sons, Inc. New York (1987–1993). Additionally, large numbers of tissue samples can be processed using techniques well known to those of skill in the art, e.g., the single-step RNA isolation process of Chomczynski, U.S. Pat. No. 4,843,155 (1989).

Transcripts within the collected RNA samples which represent RNA produced by differentially expressed genes can be identified by using a variety of methods that are well known to those of skill in the art. For example, differential screening (Tedder et al., *Proc. Natl. Acad. Sci. USA*, 85:208–212, 1988), subtractive hybridization (Hedrick et al., *Nature*, 308:149–153, 1984; Lee et al., *Proc. Natl. Acad. Sci. USA*, 88:2825, 1984), and, preferably, differential display (Pardee et al., U.S. Pat. No. 5,262,311, 1993), can be utilized to identify nucleic acid sequences derived from genes that are differentially expressed.

Differential screening involves the duplicate screening of a cDNA library in which one copy of the library is screened with a total cell cDNA probe corresponding to the mRNA population of one cell type, while a duplicate copy of the cDNA library is screened with a total cDNA probe corresponding to the mRNA population of a second cell type. For example, one cDNA probe corresponds to a total cell cDNA probe of a cell type or tissue derived from a control (healthy) subject, while the second cDNA probe corresponds to a total cell cDNA probe of the same cell type derived from an experimental subject, e.g., with a tumor or cancer (e.g., colon cancer), or from tumorous cells or tissue in the same subject. Those clones that hybridize to one probe but not to the other potentially represent clones derived from genes differentially expressed in the cell type of interest in control versus experimental subjects.

Subtractive hybridization techniques generally involve the isolation of mRNA taken from two different sources, e.g., control and experimental tissue, the hybridization of the mRNA or single-stranded cDNA reverse-transcribed from the isolated mRNA, and the removal of all hybridized, and therefore double-stranded, sequences. The remaining non-hybridized, single-stranded cDNAs, potentially represent clones derived from genes that are differentially expressed in the two mRNA sources. Such single-stranded cDNAs are then used as the starting material for the construction of a library comprising clones derived from differentially expressed genes.

The differential display technique is a procedure using the well-known polymerase chain reaction (PCR) described in Mullis, U.S. Pat. No. 4,683,202 (1987), which enables the identification of sequences derived from differentially expressed genes. First, isolated RNA is reverse-transcribed into single-stranded cDNA by standard techniques. Primers for the reverse transcriptase reaction can include, but are not limited to, oligo dT-containing primers, preferably of the 3' primer type of oligonucleotides described below.

Next, this technique uses pairs of PCR primers, as described below, which allow for the amplification of clones representing a random subset of the RNA transcripts present within any given cell. Each of the mRNA transcripts present in a cell can be amplified by using different pairs of primers. Among such amplified transcripts can be identified those which have been produced from differentially expressed genes.

The 3' oligonucleotide primer of the primer pairs can contain an oligo dT stretch of 10–13, preferably 11, dT nucleotides at its 5' end, which hybridizes to the poly(A) tail of mRNA or to the complement of a cDNA reverse transcribed from an mRNA poly(A) tail. Second, the 3' primer can contain one or more, preferably two, additional nucleotides at its 3' end to increase its specificity. Because, statistically, only a subset of the mRNA-derived sequences in the sample will hybridize to such primers, the additional nucleotides allow the primers to amplify only a subset of the mRNA-derived sequences present in the sample of interest. This is preferred because it allows more accurate and complete visualization and characterization of each of the bands representing amplified sequences.

The 5' primer can contain a nucleotide sequence expected, statistically, to hybridize to cDNA sequences derived from the tissues of interest. The nucleotide sequence can be an arbitrary one, and the length of the 5' oligonucleotide primer can range from about 9 to about 15 nucleotides, with about 13 nucleotides being preferred. Additionally, arbitrary primer sequences cause the lengths of the amplified partial cDNAs produced to be variable, thus allowing different clones to be separated by standard denaturing sequencing gel electrophoresis.

PCR reaction conditions should optimize amplified product yield and specificity and produce amplified products of lengths that can be resolved using standard gel electrophoresis techniques. Such reaction conditions are well known to those of skill in the art, and important reaction parameters include, for example, length and nucleotide sequence of oligonucleotide primers, and annealing and elongation step temperatures and reaction times.

The pattern of clones resulting from the reverse transcription and amplification of the mRNA of two different cell types is displayed via sequencing gel electrophoresis and compared. Differences in the two banding patterns indicate potentially differentially expressed genes.

Once potentially differentially expressed gene sequences have been identified by such bulk techniques, the differential expression should be corroborated. Corroboration can be accomplished, e.g., by such well-known techniques as Northern analysis, quantitative RT-coupled PCR, or RNase protection.

Also, amplified sequences of differentially expressed genes can be used to isolate the full-length clones of the corresponding gene. The full-length coding portion of the gene can be readily isolated by molecular biological techniques well known in the art. For example, the isolated, amplified fragment can be labeled and used to screen a cDNA or genomic library.

PCR technology also can be used to isolate full-length cDNA sequences. As described in this section above, the isolated amplified gene fragments (of about at least 10 nucleotides, preferably longer, of about 15 nucleotides) have their 5' terminal end at some random point within the gene, and have 3' terminal ends at a position corresponding to the 3' end of the transcribed portion of the gene. Once nucleotide sequence information from an amplified fragment is obtained, the remainder of the gene, i.e., the 5' end of the gene, when utilizing differential display, can be obtained using, for example, RT PCR.

In one embodiment of such a procedure for the identification and cloning of full-length gene sequences, RNA is isolated, following standard procedures, from an appropriate tissue or cellular source. A reverse transcription reaction is then performed on the RNA using an oligonucleotide primer complementary to the mRNA that corresponds to the amplified cloned fragment, for the priming of first strand synthesis. Because the primer is anti-parallel to the mRNA, extension will proceed toward the 5' end of the mRNA. The resulting RNA/DNA hybrid is then "tailed" with guanines using a standard terminal transferase reaction, the hybrid is digested with RNAase H, and second strand synthesis is then primed with a poly-C primer.

Using the two primers, the 5' portion of the gene is then amplified using PCR. Sequences obtained are then isolated and recombined with previously isolated sequences to generate a full-length cDNA of the differentially expressed genes of the invention. For a review of suitable cloning strategies and recombinant DNA techniques, see, e.g., Sambrook et al., *Molecular Cloning, A Laboratory Manual*, (Cold Springs Harbor Press, N.Y., 1989); and Ausubel et al., *Current Protocols in Molecular Biology*, (Green Publishing Associates and Wiley Interscience, N.Y., 1989).

4.2. Methods for the Identification of Pathway Genes

Any method suitable for detecting protein-protein interactions can be employed to identify pathway gene products by identifying. interactions between gene products and gene products known to be involved in tumors and cancers, e.g., those involved in colon cancer as described herein. Such known gene products can be cellular or extracellular proteins. Those gene products that interact with known gene products represent pathway gene products and the genes which encode them represent pathway genes.

Among the traditional methods that can be employed to identify pathway gene products are cross-linking, co-immunoprecipitation, and co-purification through gradients or chromatographic columns. Once identified, a pathway gene product can be used with standard techniques to identify its corresponding pathway gene. For example, at least a portion of the amino acid sequence of the pathway gene product can be ascertained using techniques well known to those of skill in the art, such as via the Edman degradation technique (see, e.g., Creighton, *Proteins: Structures and Molecular Principles*, (W. H. Freeman & Co., N.Y., 1983), pp. 34–49). The amino acid sequence obtained can be used as a guide for the generation of oligonucleotide mixtures that can be used to screen for pathway gene sequences. Screening can be accomplished, for example, by standard hybridization or PCR techniques. Techniques for the generation of oligonucleotide mixtures and the screening are well known (see, e.g., Ausubel, supra, and Innis et al. (eds.), *PCR Protocols: A Guide to Methods and Applications*, (Academic Press, Inc., New York, 1990)).

Additionally, methods can be employed to simultaneously identify pathway genes that encode a protein interacting with a protein related to a tumor or cancer (e.g., colon cancer). These methods include, for example, probing expression libraries with a labeled protein that is known or suggested to be involved in a tumor or cancer, e.g., a protein encoded by the differentially expressed genes described herein, using this protein in a manner similar to the well known technique of antibody probing of λgt11 libraries.

One method that detects protein interactions in vivo, the yeast two-hybrid system, is described in detail below for illustration only and not by way of limitation. One version of this system has been described in Chien et al., *Proc. Natl. Acad. Sci. USA*, 88:9578–9582 (1991), and is commercially available from Clontech (Palo Alto, Calif.).

Briefly, utilizing such a system, plasmids are constructed that encode two hybrid proteins: the first hybrid protein consists of the DNA-binding domain of a transcription factor, e.g., activation protein, fused to a known protein, in this case, a protein known to be involved in a tumor or cancer, and the second hybrid protein consists of the transcription factor's activation domain fused to an unknown protein that is encoded by a cDNA which has been recombined into this plasmid as part of a cDNA library. The plasmids are transformed into a strain of the yeast Saccharomyces cerevisiae that contains a reporter gene, e.g., lacZ, whose expression is regulated by the transcription factor's binding site.

Either hybrid protein alone cannot activate transcription of the reporter gene. The DNA binding hybrid protein cannot activate transcription because it does not provide the activation domain function, and the activation domain hybrid protein cannot activate transcription because it lacks the domain required for binding to its target site, i.e., it cannot localize to the transcription activator protein's binding site. Interaction between the DNA binding hybrid protein and the library encoded protein reconstitutes the functional transcription factor and results in expression of the reporter gene, which is detected by an assay for the reporter gene product.

The two-hybrid system or similar methods can be used to screen activation domain libraries for proteins that interact with a known "bait" gene product. By way of example, and not by way of limitation, gene products, e.g., of the genes described herein, known to be involved in a particular tumor or cancer, e.g., colon cancer, can be used as the bait gene products. Total genomic or cDNA sequences are fused to the DNA encoding an activation domain. This library and a plasmid encoding a hybrid of the bait gene product fused to the DNA-binding domain are cotransformed into a yeast reporter strain, and the resulting transformants are screened for those that express the reporter gene. For example, and not by way of limitation, the bait gene can be cloned into a vector such that it is translationally fused to the DNA encoding the DNA-binding domain of the GAL4 protein. The colonies are purified and the (library) plasmids responsible for reporter gene expression are isolated. The inserts in the plasmids are sequenced to identify the proteins encoded by the cDNA or genomic DNA.

A cDNA library of a cell or tissue source that expresses proteins predicted to interact with the bait gene product can be made using methods routinely practiced in the art. According to the particular system described herein, the library is generated by inserting the cDNA fragments into a vector such that they are translationally fused to the activation domain of GAL4. This library can be co-transformed along with the bait gene-GAL4 fusion plasmid into a yeast strain which contains a lacZ gene whose expression is controlled by a promoter which contains a GAL4 activation sequence. A cDNA encoded protein, fused to GAL4 activation domain, that interacts with the bait gene product will reconstitute an active GAL4 transcription factor and thereby drive expression of the lacZ gene. Colonies that express lacZ can be detected by their blue color in the presence of X-gal. cDNA containing plasmids from such a blue colony can then be purified and used to produce and isolate the bait gene product interacting protein using techniques routinely practiced in the art.

4.3. Characterization of Differentially Expressed and Pathway Genes

Differentially expressed genes, such as those identified via the methods discussed above in Section 4.1, and pathway genes, such as those identified via the methods discussed above in Section 4.2, as well as genes identified by alternative means, can be further characterized by using methods such as those discussed herein. Such genes will be referred to herein as "identified genes."

Any of the differentially expressed genes whose modulation of the gene's expression, or a modulation of the gene product's activity can inhibit tumors and cancers will be designated "target genes," as defined above. Any of the differentially expressed genes or pathway genes whose modulation does not positively affect tumors and cancers, but whose expression pattern contributes to a gene expression "fingerprint" pattern correlative of tumors and cancers will be designated "fingerprint genes." Each of the target genes can also function as a fingerprint gene, as can all or a portion of the pathway genes.

A variety of techniques can be used to further characterize the identified genes. First, the nucleotide sequence of the identified genes, which can be obtained by standard techniques, can be used to further characterize such genes. For example, the sequence of the identified genes can reveal homologies to one or more known sequence motifs which can yield information regarding the biological function of the identified gene product.

Second, the tissue and/or cell type distribution of the mRNA produced by the identified genes can be analyzed using standard techniques, e.g., Northern analyses, RT-coupled PCR, and RNase protection techniques. Such analyses provide information as to whether the identified genes are expressed in tumorous tissues, e.g., in colon cancer. Such analyses can also provide quantitative information regarding steady state mRNA regulation. Additionally, standard in situ hybridization techniques can be used to provide information regarding which cells within a given tissue express the identified gene.

Third, the sequences of the identified genes can be localized onto genetic maps, e.g., mouse (Copeland et al., *Trends in Genetics*, 7:113–118, 1991) and human genetic maps (Cohen, et al., *Nature*, 366:698–701, 1993). Such mapping information can yield information regarding the genes' importance to human disease by, for example, identifying genes that map within genetic regions to which known tumors and cancers map. For example, Vogelstein et al., *Science*, 244:207–211 (1989), describes allelic deletions in different chromosomes associated with colorectal carcinomas in humans.

Fourth, the biological function of the identified genes can be more directly assessed in relevant in vivo and in vitro systems. In vivo systems can include, but are not limited to, animals that naturally exhibit symptoms of tumors or cancers, or animals engineered to exhibit such symptoms. For example, colon cancer animal models can be generated by injecting animals, such as mice, with colon tumor cells, some of which will give rise to tumors.

The role of identified gene products, e.g., gene products of the genes identified:herein, can be determined by transfecting cDNAs encoding these gene products into appropriate cell lines, such as, for example, Caco-2 and HT29, and analyzing the effect on tumor (e.g., colon cancer) characteristics. For example, the role and function of genes important in the progression of human colon cancer are assessed using the cells implanted into nude mice ceca and the number of tumors that develop are determined. Tumor volume and number of metastases are also determined. Tumor growth can also be observed in vitro in soft agar, which typically does not support growth of normal cells. The function of genes isolated using human colorectal tumors and their hepatic metastases are assessed by expressing the gene in the appropriate model, e.g., the METAMOUSE™ model described above.

4.4. Differentially Expressed and Pathway Genes

The differentially expressed and pathway genes of the invention are listed below in Table 1. Nucleotide sequences corresponding to differentially expressed genes are shown in FIGS. 1a to 1p and FIGS. 2 to 7. Specifically, FIGS. 1a to 1p depict the nucleotide sequences of the amplified cDNA sequences initially identified via differential display analysis. FIGS. 2 to 7 depict longer nucleotide sequences corresponding to several of the genes of the invention.

Table 1 summarizes information regarding the further characterization of the differentially expressed genes of the invention detected in the specimen paradigm. Table 1 lists SEQ ID NOs, figure numbers, chromosome location (where determined), and references to similar or identical sequences found in nucleic acid databases ("Database Hits"). No references are listed for novel genes, i.e., where no identical gene sequences were found in published databases.

Further in Table 1, in the column headed "Higher Expression In," "N" indicates that gene expression was higher in normal (e.g., non-tumorous) cells, i.e., there was a greater steady state amount of detectable mRNA produced by a given gene in the normal cells than in tumor cells, while "T" indicates that gene expression was higher in tumor cells, i.e., there was a higher steady state amount of detectable mRNA produced by a given gene in the tumor colon cells than in the normal colon cells. Table 1 also shows the results of RT-PCR. "Nd" indicates "not done."

In the table, numbers in parenthesis in the "RT-PCR" column show the number of positive samples, i.e., samples that confirmed the results of the expression pattern in the differential display specimen paradigm, over the, number of total samples (8 or 12) assayed. A "+" indicates a positive result. When relevant, the number/name of the human chromosome to which the cDNA sequence mapped is given.

The full-length cDNA sequences of the genes listed in Table 1 can be obtained using methods well known to those skilled in the art, including, but not limited to, the use of appropriate probes to detect the genes within an appropriate cDNA or gDNA (genomic DNA) library (see, for example, Sambrook et al., *Molecular Cloning: A Laboratory Manual, Cold Spring Harbor Laboratories*, 1989). Another technique for obtaining a full-length cDNA that can be used instead of, or in conjunction with, library screening is the so-called "RACE" technique, which stands for rapid amplification of cDNA ends.

Oligonucleotide probes corresponding to the DNA sequences reported herein can be synthesized, using techniques well known to those of skill in the art, based on the DNA sequences disclosed herein in FIGS. 1a to 1p and FIGS. 2 to 7. The probes can be used to screen cDNA libraries prepared from an appropriate cell or cell line in which the gene is transcribed. For example, PCR primers based on the nucleotide sequences. in FIGS. 1a to 1p and FIGS. 2 to 7 can be used to probe human tissue libraries to determine if a given gene is present. Then, labelled probes are used to screen the libraries to obtain the desired gene.

In particular, useful human tissue cDNA libraries are available from, e.g., Clontech (Palo Alto, Calif.), and include: brain (HL1065a), colon (HL1034a), colon cancer (HL1148a), liver (HL1115a), lung (HL1158a), and kidney (HL1033a) libraries. A human muscle cDNA library is available from Stratagene (La Jolla, Calif.). These or other human tissue cDNA libraries are screened using probes based on the DNA fragments of FIGS. 1a to 1p and 2 to 7. Duplicate filters with a total of one million phage from the cDNA library are hybridized in 5×SSCPE, 5×Denhard's solution, and 50% formamide with about $10^6$ cpm per ml of radiolabeled DNA probe. The filters are washed to a final stringency of 0.5×SSCPE and 0.1% SDS at 65° C. and exposed to Kodak XPR film at −80° C. with an intensifying screen. λ phage hybridizing to the probe on duplicate filters are plaque-purified and their cDNA inserts sequenced using standard techniques.

Another standard technique for obtaining full-length cDNAs from a known DNA sequence is the RACE technique. This technique can be carried out using Clontech's MARATHON™ ready cDNAs (e.g., Human Lung, Cat# 7408-1, Human Brain, Cat#7400-1) and Adaptor primers (AP1 and AP2)(Clontech, Palo Alto, Calif.). In this method, two nested 30–35 mer gene-specific oligos are generated from a known cDNA sequence (with orientation specific for generating either 3 or 5' RACE products), and are used to extend the ends of the known sequence.

RACE was performed for a variety of the cDNA fragments described in FIGS. 1a to 1p using MARATHON-ready cDNA as a template, the distal gene-specific primer,. the AP1 adaptor primer, ExTaq DNA polymerase (PanVera, Madison Wis.) and a TaqStart antibody (Clontech, Palo Alto, Calif.). Reaction conditions were as follows: 94° C. for 1 minutes, then 5 cycles of 94° C. for 30 seconds, 72° C. for 4 minutes, then 5 cycles of 94° C. for 30 seconds, 70° C. for 4 minutes, then 20 cycles of 94° C. for 20 seconds, then 68° C. for 4 minutes.

1/50th of the initial PCR reaction was used as template with the nested gene-specific primer and the AP2 adaptor primer, using the same conditions. All products were analyzed by electrophoresis, and resultant bands were gel-isolated and cloned directly, or the separated PCR products were Southern blotted and hybridized with another gene-specific oligo to determine which products were of interest.

To clone human genomic DNA corresponding to a full-length cDNA, a cDNA fragment can be used to probe human high density PAC filters from Genome Systems, Inc. (St. Louis, Mo., Catalog No. FPAC-3386). The probe is random prime-labelled using the Prime-It kit (Stragagene; Catalog No. 300392). The hybridization is carried out in Amersham Rapid-hyb buffer according to the manufacturer's recommendations. The filters are then washed in 2×SSC/1% SDS at 65° C. and exposed to Kodak film at −80° C. Grid positions of positive PAC clones are identified, and the corresponding clones can be obtained from Genome Systems, Inc. The genomic clones are important for designing diagnostic reagents, e.g., by providing intron/exon boundaries.

symptoms. Mutant alleles and mutant allele products can then be used in the therapeutic and diagnostic assay systems described below.

A cDNA of a mutant gene can be isolated, for example, by using PCR. In this case, the first cDNA strand can be synthesized by hybridizing an oligo-dT oligonucleotide to mRNA isolated from tissue, e.g., colon tissue, in an individual known or suspected of carrying the mutant allele, and by extending the new strand with reverse transcriptase. The second strand of the cDNA can then be synthesized using an oligonucleotide that hybridizes specifically to the 5'—end of the normal gene. Using these two primers, the product is then amplified via PCR, cloned into a suitable vector, and subjected to DNA sequence analysis through methods well-known to one skilled in the art. By comparing the DNA sequence of the mutant gene to that of the normal gene, the mutation(s) responsible for the loss or alteration of function of the mutant gene product can be determined.

Alternatively, a genomic or cDNA library can be constructed and screened using DNA or RNA, respectively, from a tissue known to or suspected of expressing the gene of interest in an individual suspected of or known to carry the mutant allele. The normal gene or any suitable fragment thereof can then be labeled and used as a probe to identify the corresponding mutant allele in the library. The clone containing this gene can then be purified through routine methods and subjected to sequence analysis as described in this Section.

TABLE 1

Differentially Expressed and Pathway Genes

| Gene | SEQ ID NOs | Higher Expression In | Chromosome | RT-PCR | Database Hits | FIG. Nos. |
|---|---|---|---|---|---|---|
| 029 | 1 | N | nd | (8/12) | no | 1a |
| 030 | 2 | N | nd | + | human MAL | 1b |
| 036, 095 | 3 13 24 | N | 4 | (11/12) | EST B4E07 | 1c 1m 7 |
| 038, 102 | 4 | N | nd | (7/12) | no | 1d |
| 048 | 5 19 | T | 17 | (10/12) | no | 1e 3 |
| 056 | 6 | N | (10) | (8/8) | human calcium activated potassium chanel mRNA hSlo | 1f |
| 075 | 7 | N | nd | (5/8) | no | 1g |
| 082 | 8 17 | N | 19 | (4/8) | human protocadherin (pc42) | 1h 2 |
| 083 | 9 | T | X | (6/12) | no | 1i |
| 090 | 10 20 | T | 15 | (6/12) | no | 1j 4 |
| 092 | 11 | N | 4 | (10/12) | no | 1k |
| 093 | 12 21 | T | 12 | (11/12) | no | 1l 5 |
| 096, 105 | 14 | N | nd | (5/8) | bovine GTP-binding regulatory protein gamma-6 subunit | 1n |
| 097 | 15 | T | nd | (10/12) | human translationally controlled tumor protein | 1o |
| 101 | 16 22 | N | 4 | (7/12) | no | 1p 6 |

In cases where the differentially expressed or pathway gene identified is a normal, or wild type, gene, this gene can be used to isolate mutant alleles of the gene. Such an isolation is preferable in processes and disorders which are known or suspected of having a genetic basis. Mutant alleles can be isolated from individuals either known or suspected of having a genotype that contributes to tumor or cancer Additionally, an expression library can be constructed utilizing DNA isolated from or cDNA synthesized from a tissue known to express, or suspected of expressing, the gene of interest in an individual suspected of carrying, or known to carry, the mutant allele. In this manner, gene products made by the putatively mutant tissue can be expressed and screened using standard antibody screening techniques in conjunction with antibodies raised against the normal gene product as described below (for screening techniques, see, for example, Harlow et al. (eds.), *Antibodies: A Laboratory Manual*, (Cold Spring Harbor Press, Cold Spring Harbor, 1988).

In cases where the mutation results in an expressed gene product with altered function, e.g., as a result of a missense mutation, a polyclonal set of antibodies is likely to cross-react with the mutant gene product. Library clones detected via their reaction with such labeled antibodies can be purified and subjected to sequence analysis as described in this Section.

4.5. Differentially Expressed and Pathway Gene Products

Differentially expressed and pathway gene products include those peptides encoded by the differentially expressed and pathway gene sequences described in Section 4.2.1, above. Specifically, differentially expressed and pathway gene products can include differentially expressed and pathway gene polypeptides encoded by the differentially expressed and pathway gene sequences contained in the coding regions of the genes corresponding to the DNA sequences in FIGS. 1a through 1p and FIGS. 2 to 7.

In addition, differentially expressed and pathway gene products can include peptides and proteins that represent functionally equivalent gene products. Such an equivalent gene products can contain deletions, additions, or substitutions of amino acid residues, but which result in a silent change, thus producing a functionally equivalent product. Amino acid substitutions can be made on the basis of similarity in polarity, charge, solubility, hydrophobicity, hydrophilicity, and/or the amphipatic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent," as used herein, refers to either a peptide that exhibits a substantially similar in vivo activity as the endogenous differentially expressed or pathway gene products encoded by the differentially expressed or pathway gene sequences described in Section 4.2.1, above. Alternatively, when used as part of assays such as those described, herein, "functionally equivalent" can refer to peptides capable of interacting with other cellular or extracellular molecules in a manner substantially similar to the way in which the corresponding portion of the endogenous differentially expressed or pathway gene product would.

The differentially expressed or pathway gene products can be produced by synthetic techniques or via standard recombinant DNA technology. Methods for preparing the differentially expressed or pathway gene peptides of the invention by expressing nucleic acid encoding differentially expressed or pathway gene sequences are described herein. Methods well known to those skilled in the art can be used to construct expression vectors containing differentially expressed or pathway gene protein coding sequences and appropriate transcriptional/translational control signals. These methods include, for example, in vitro recombinant DNA techniques, synthetic techniques, and in vivo recombination/genetic recombination. See, for example, the techniques described in Maniatis et al., *Molecular Cloning A Laboratory Manual* (Cold Spring Harbor Laboratory, N.Y., 1989), and Ausubel, 1989, supra. Alternatively, RNA capable of encoding differentially expressed or pathway gene protein sequences can be chemically synthesized using, for example, synthesizers. See, for example, the techniques described in Gait, M. J. ed., *Oligonucleotide Synthesis*, (IRL Press, Oxford, 1984).

A variety of host-expression vector systems can be used to express the differentially expressed or pathway gene coding sequences of the invention. Such host-expression systems represent vehicles by which the coding sequences of interest can be produced and subsequently purified, but also represent cells that can, when transformed or transfected with the appropriate nucleotide coding sequences, exhibit the differentially expressed or pathway gene protein of the invention in situ. These include, but are not limited to, microorganisms such as bacteria, e.g., *E. coli* or, *B. subtilis*, transformed with recombinant bacteriophage DNA, plasmid or cosmid DNA expression vectors containing differentially expressed or pathway gene protein coding sequences; yeast, e.g., Saccharomyces or Pichia, transformed with recombinant yeast expression vectors containing the differentially expressed or pathway gene protein coding sequences; insect cell systems infected with recombinant virus expression vectors, e.g., baculovirus, containing the differentially expressed or pathway gene protein coding sequences; plant cell systems infected with recombinant virus expression vectors, e.g., cauliflower mosaic virus (CaMV) or tobacco mosaic virus (TMV), or transformed with recombinant plasmid expression vectors, e.g., Ti plasmids, containing differentially expressed or pathway gene protein coding sequences; or mammalian cell systems, e.g., COS, CHO, BHK, 293 or 3T3, harboring recombinant expression constructs containing promoters derived from the genome of mammalian cells, e.g., metallothionein promoter, or from mammalian viruses, e.g., the adenovirus late promoter or the vaccinia virus 7.5K promoter.

When used as a component in assay systems such as those described herein, the differentially expressed or pathway gene protein can be labeled, either directly or indirectly, to facilitate detection of a complex formed between the differentially expressed or pathway gene protein and a test substance. Any of a variety of suitable labeling systems can be used including but not limited to radioisotopes such as $^{125}$I; enzyme labelling systems that generate a detectable calorimetric signal or light when exposed to substrate; and fluorescent labels.

Where recombinant DNA technology is used to produce the differentially expressed or pathway gene protein for such assay systems, it can be advantageous to engineer fusion proteins that can facilitate labeling, solubility, immobilization, and/or detection.

Indirect labeling involves the use of a third protein, such as a labeled antibody, which specifically binds to either a differentially expressed or pathway gene product. Such antibodies include but are not limited to polyclonal, monoclonal, chimeric, single chain, Fab fragments, and fragments produced by a Fab expression library.

4.6. Antibodies Specific for Differentially Expressed or Pathway Gene Products Antibodies that specifically bind to one or more differentially expressed or pathway gene epitopes can be produced by a variety of methods. Such antibodies can include, but are not limited to, polyclonal antibodies, monoclonal antibodies (mAbs), humanized or chimeric antibodies, single chain antibodies, Fab fragments, F(ab')$_2$ fragments, fragments produced by a FAb expression library, anti-idiotypic (anti-Id) antibodies, and epitope-binding fragments of any of the above.

Such antibodies can be used, for example, in the detection of a fingerprint, target, or pathway gene in a biological sample, or, alternatively, in a method for the inhibition of abnormal target gene activity. Thus, such antibodies can be used in treatment methods for tumors and cancers (e.g., colon cancer), and/or in diagnostic methods whereby patients can be tested for abnormal levels of fingerprint, target, or pathway gene proteins, or for the presence of abnormal forms of such proteins.

To produce antibodies to a differentially expressed or pathway gene protein, a host animal is immunized with the protein, or a portion thereof. Such host animals can include but are not limited to rabbits, mice, and rats. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin (KLH), dinitrophenol (DNP), and potentially useful human adjuvants such as BCG (bacille Calmette-Guerin) and *Corynebacterium parvum*.

Monoclonal antibodies, which are homogeneous populations of antibodies to a particular antigen, can be obtained by any technique which provides for the production of antibody molecules by continuous cell lines in culture. These include, but are not limited to the hybridoma technique of Kohler and Milstein, (*Nature*, 256:495–497, 1975; and U.S. Pat. No. 4,376,110), the human B-cell hybridoma technique (Kosbor et al., *Immunology Today*, 4:72, 1983; Cole et al., *Proc. Natl. Acad. Sci. USA*, 80:2026–2030, 1983), and the BV-hybridoma technique (Cole et al., *Monoclonal Antibodies And Cancer Therapy* (Alan R. Liss, Inc. 1985), pp. 77–96. Such antibodies can be of any immunoglobulin class including IgG, IgM, IgE, IgA, IgD and any subclass thereof. The hybridoma producing the mAb of this invention can be cultivated in vitro or in vivo. Production of high titers of mAbs in vivo makes this the presently preferred method of production.

In addition, techniques developed for the production of "chimeric antibodies" can be made by splicing the genes from a mouse antibody molecule of appropriate antigen specificity together with genes from a human antibody molecule of appropriate biological activity (see, Morrison et al., *Proc. Natl. Acad. Sci.*, 81:6851–6855, 1984; Neuberger et al., *Nature*, 312:604–608, 1984; Takeda et al., *Nature*, 314:452–454, 1985; and U.S. Pat. No. 4,816,567). A chimeric antibody is a molecule in which different portions are derived from different animal species, such as those having a variable region derived from a murine mAb and a constant region derived from human immunoglobulin.

Alternatively, techniques described for the production of single chain antibodies (e.g., U.S. Pat. No. 4,946,778; Bird, *Science*, 242:423–426, 1988; Huston et al., *Proc. Natl. Acad. Sci. USA*, 85:5879–5883, 1988; and Ward et al., *Nature*, 334:544–546, 1989), and for making humanized monoclonal antibodies (U.S. Pat. No. 5,225,539), can be used to produce anti-differentially expressed or anti-pathway gene product antibodies.

Antibody fragments that recognize specific epitopes can be generated by known techniques. For example, such fragments include but are not limited to: the F(ab')$_2$ fragments that can be produced by pepsin digestion of the antibody molecule, and the Fab fragments that can be generated by reducing the disulfide bridges of the F(ab')$_2$ fragments. Alternatively, Fab expression libraries can be constructed (Huse et al., *Science*, 246:1275–1281, 1989) to allow rapid and easy identification of monoclonal Fab fragments with the desired specificity.

4.7. Cell- and Animal-Based Model Systems

Cell- and animal-based model systems for tumors and cancers (e.g., colon cancer) can be used to identify differentially expressed genes via the paradigms described in Section 4.1.1. Such systems can also be used to further characterize differentially expressed and pathway genes as described in Section 4.3. In addition, an unknown compound's ability to ameliorate symptoms in these models can be used to identify drugs, pharmaceuticals, therapies, and interventions effective in treating tumors and cancers. Animal models also can be used to determine the LD$_{50}$ and the ED$_{50}$ of a compound, and such data can be used to determine the in vivo efficacy of potential anti-colon tumor or cancer treatments.

4.7.1. Animal Models

Animal models of tumors and cancers (e.g., colon cancer) include both non-recombinant as well as recombinantly engineered transgenic animals. Non-recombinant animal models for cancer include, for example, murine models. Such models can be generated, for example, by introducing tumor cells into syngeneic mice using techniques such as subcutaneous injection, tail vein injection, spleen implantation, intraperitoneal implantation, implantation under the renal capsule, or orthotopic implantation, e.g., colon cancer cells implanted in colonic tissue. See the discussion of the METAMOUSE™ above. After an appropriate period of time, the tumors resulting from these injections can be counted and analyzed. Cells that can be used in such animal models are cells derived from tumors and cancers (e.g., colon cancer), or cell lines such as Caco-2 or HT-29.

The role of identified gene products, e.g., encoded by genes described herein, can be determined by transfecting cDNAs encoding such gene products into the appropriate cell line and analyzing its effect on the cells' ability to induce tumors and cancers in an animal model. The role of the identified gene products can be further analyzed by culturing cells derived from the tumors which develop in the animal models, introducing these cultured cells into animals, and subsequently measuring the level of identified gene product present in the resulting tumor cells. In this manner, cell line variants are developed that can be used in analyzing the role of quantitative and/or qualitative differences in the expression of the identified genes on the cells' ability to induce tumors and cancers.

Additionally, recombinant animal models exhibiting tumor and cancer characteristics and/or symptoms, can be engineered by using, for example, target gene sequences such as those described in Section 4.4, in conjunction with standard techniques for producing transgenic animals. For example, target gene sequences are introduced into, and overexpressed in, the genome of the animal of interest, or, if endogenous target gene sequences are present, they are either overexpressed or, alternatively, are disrupted to underexpress or inactivate target gene expression.

To overexpress a target gene sequence, the coding portion of the target gene sequence can be ligated to a regulatory sequence which can drive gene expression in the animal and cell type of interest. Such regulatory regions are well known to those of skill in the art.

To underexpress an endogenous target gene sequence, such a sequence can be introduced into the genome of the animal of interest such that the endogenous target gene alleles will be inactivated. Preferably, an engineered sequence including at least part of the target gene sequence is used and introduced, via gene targeting, such that the endogenous target sequence is disrupted upon integration of the engineered target gene sequence into the animal's genome. Gene targeting is discussed below.

Animals of many species, including, but not limited to, mice, rats, rabbits, guinea pigs, pigs, micro-pigs, goats, and non-human primates, e.g., baboons, monkeys, and chimpanzees, can be used to generate animal models of tumors and cancers (e.g., colon, liver, stomach, or lung cancer).

Techniques known in the art can be used to introduce a target gene transgene into animals to produce the founder lines of transgenic animals. Such techniques include, but are not limited to, pronuclear microinjection (Hoppe, P. C. and Wagner, T. E., U.S. Pat. No. 4,873,191, 1989); retrovirus mediated gene transfer into germ-lines (Van der Putten et al., *Proc. Natl. Acad. Sci., USA*, 82:6148–6152, 1985); gene targeting in embryonic stem cells (Thompson et al., *Cell*, 56:313–321, 1989); electroporation of embryos (Lo, *Mol Cell. Biol.*, 3:1803–1814, 1983); and sperm-mediated gene transfer (Lavitrano et al., *Cell*, 57:717–723, 1989). For a review of such techniques, see, e.g., Gordon, *Transgenic Animals, Intl. Rev. Cytol.*, 115:171–229, 1989. See also Leder et al., U.S. Pat. No. 4,736,866 (Transgenic Non-Human Mammal).

The present invention includes transgenic animals that carry the transgene in all their cells, as well as animals that carry the transgene in some, but not all their cells, i.e., mosaic animals. The transgene can be integrated, either as a single transgene or in concatamers, e.g., head-to-head or head-to-tail tandems. The transgene can also be selectively introduced into and activated in a particular cell type by following, for example, the technique of Lasko et al. *Proc. Natl. Acad. Sci. USA*, 89:6232–6236, 1992. The regulatory sequences required for such a cell type-specific activation depend upon the particular cell type of interest.

When it is desired that the target gene transgene be integrated into the chromosomal site of the endogenous target gene, gene targeting is preferred. Briefly, for this technique, vectors containing some nucleotide sequences homologous to the endogenous target gene of interest are designed for the purpose of integrating, via homologous recombination with chromosomal sequences, into and disrupting the function of, the nucleotide sequence of the endogenous target gene. The transgene can also be selectively introduced into a particular cell type, thus inactivating the endogenous gene of interest in only that cell type, by following, for example, the techniques of Gu et al., *Science*, 265:103–106, 1994). The regulatory sequences required for such a cell type-specific inactivation depend upon the particular cell type of interest, and are apparent to those of skill in the art.

Once transgenic animals have been generated, the expression of the recombinant target gene and protein can be assayed by standard techniques. Initial screening can be accomplished by Southern blot analysis or PCR techniques to analyze animal tissues to assay whether integration of the transgene has taken place. The level of mRNA expression of the transgene in the tissues of the transgenic animals can also be assessed using techniques such as Northern blot analysis of tissue samples obtained from the animal, in situ hybridization analysis, and RT-coupled PCR. Samples of target gene-expressing tissue can also be evaluated immunocytochemically using antibodies specific for the transgenic product of interest.

The target gene transgenic animals that express target gene mRNA or target gene transgene peptide (detected immunocytochemically, using antibodies directed against target gene product epitopes) at easily detectable levels should then be further evaluated to identify those animals which display tumor or cancer characteristics. For example, colon tumor characteristics and/or symptoms can include, for example, those associated with the progressive formation of intestinal polyps, adenomas, adenocarcinoma, and metastic lesions.

4.7.2. Cell-Based Systems

Cells that contain and express target gene sequences that encode target gene peptides and exhibit cellular phenotypes associated with tumors and cancers (e.g., colon cancer) can be used to identify compounds that prevent and/or ameliorate tumors and cancers. Further, the fingerprint pattern of gene expression of cells of interest can be analyzed and compared to the normal fingerprint pattern. Those compounds that cause cells exhibiting cellular phenotypes of tumors and cancers to produce a fingerprint pattern more closely resembling a normal fingerprint pattern for the cell of interest are considered candidates for further testing.

Cells for such assays can include non-recombinant colon cell lines, such as, but not limited to, human colon adenocarcinoma cell lines Caco-2 and HT29. In addition, purified primary or secondary tumor cells derived from either transgenic or non-transgenic tumor cells can be used.

Further, cells for such assays can also include recombinant, transgenic cell lines. For example, the tumor or cancer animal models of the invention can be used to generate cell lines, containing one or more cell types involved in tumors or cancers, that can be used as cell culture models for this disorder. While primary cultures derived from tumors or cancers in transgenic animals of the invention can be used, the generation of continuous cell lines is preferred. For examples of techniques that can be used to derive a continuous cell line from a transgenic animal, see Small et al., *Mol. Cell Biol.*, 5:642–648, 1985.

Alternatively, cells of a cell type known to be involved in a particular tumor or cancer can be transfected with sequences that increase or decrease the amount of target gene expression within the cell. For example, target gene sequences can be introduced into, and overexpressed in, the genome of the cell of interest, or, if endogenous target gene sequences are present, they can either be overexpressed or, alternatively, be disrupted to underexpress or inactivate target gene expression. These techniques are well known in the art and are discussed above.

Transfection of target gene sequence nucleic acid also can be accomplished by standard techniques. See, for example, Ausubel, 1989, supra. Transfected cells should be evaluated for the presence of the recombinant target gene sequences, for expression and accumulation of target gene mRNA, and for the presence of recombinant target gene protein production. When a decrease in target gene expression is desired, standard techniques can be used to demonstrate whether a decrease in endogenous target gene expression and/or in target gene product production is achieved.

4.8. Screening Assays for Compounds that Interact with the Target Gene Product The following assays are designed to identify compounds that bind to target gene products or to cellular proteins that interact with a target gene product, and compounds that interfere with the interaction of the target gene product with other cellular proteins.

Specifically, such compounds can include, but are not limited to, peptides, such as, soluble peptides, e.g., Ig-tailed fusion peptides, comprising extracellular portions of target gene product transmembrane receptors, and members of random peptide libraries (see, e.g., Lam et al., *Nature*, 354:82–84, 1991; Houghton et al., *Nature*, 354:84–86, 1991), made of D- and/or L-configuration amino acids, phosphopeptides (including, but not limited to, members of random or partially degenerate phosphopeptide libraries; see, e.g., Songyang et al., *Cell*, 72:767–778, 1993), antibodies (including, but not limited to, polyclonal, monoclonal, humanized, anti-idiotypic, chimeric or single chain antibodies, and FAb, F(ab')$_2$, and FAb expression library fragments, and epitope-binding fragments thereof), and small organic or inorganic molecules.

4.8.1. In Vitro Screening Assays for Compounds That Specifically Bind to a Target Gene Product In vitro assay systems can identify compounds that specifically bind to the target gene products of the invention. The assays all involve the preparation of a reaction mixture of a target gene protein and a test compound under conditions and for a time sufficient to allow the two components to interact and bind, thus forming a complex that can be removed and/or detected in the reaction mixture. These assays can be conducted in a variety of ways. For example, one method involves anchoring target gene product or the test substance to a solid phase, and detecting target gene product/test compound complexes anchored to the solid phase at the end of the reaction. In one embodiment of such a method, the target gene product can be anchored onto a solid surface, and the test compound, which is not anchored, can be labeled, either directly or indirectly.

In practice, microtiter plates can be used as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

To conduct the assay, the non-immobilized component is added to the coated surface containing the anchored component. After the reaction is complete, unreacted components are removed, e.g., by washing, and complexes anchored on the solid surface are detected. Where the previously immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with a labeled anti-Ig antibody).

Alternatively, the reaction can be conducted in a liquid phase, the reaction products separated from unreacted components, and complexes detected, e.g., using an immobilized antibody specific for a target gene or the test compound to anchor any complexes formed in solution, and a labeled antibody specific for the other component of the possible complex to detect anchored complexes.

4.8.2. Assays for Cellular Proteins that Interact with the Target Gene Products

Any method suitable for detecting protein-protein interactions can be used to identify novel target product-cellular or extracellular protein interactions. These methods are outlined in Section 4.1.3., supra, for the identification of pathway genes, and can be used to identify proteins that interact with target proteins. In such a case, the target gene serves as the known "bait" gene.

4.8.3. Assays for Compounds that Interfere with Gene/Cellular Product Interactions The target gene products of the invention can interact in vivo with one or more cellular or extracellular macromolecules, such as proteins and nucleic acid molecules. Such cellular and extracellular macromolecules are referred to herein as "binding partners." Compounds that disrupt such interactions can be used to regulate the activity of the target gene product, especially mutant target gene products. Such compounds can include, but are not limited to, molecules such as antibodies and peptides.

The assay systems all involve the preparation of a reaction mixture containing the target gene product, and the binding partner under conditions and for a time sufficient to allow the two products to interact and bind, thus forming a complex. To test a compound for inhibitory activity, the reaction mixture is prepared in the presence and absence of the test compound. The test compound can be initially included in the reaction mixture, or can be added at a time subsequent to the addition of a target gene product and its cellular or extracellular binding partner. Control reaction mixtures are incubated without the test compound or with a placebo. The formation of complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases in which it is desirable to identify compounds that disrupt interactions of mutant but not normal target gene products.

The assays can be conducted in a heterogeneous or homogeneous format. Heterogeneous assays involve anchoring either the target gene product or the binding partner to a solid phase and detecting complexes anchored to the solid phase at the end of the reaction, as described above. In homogeneous assays, the entire reaction is carried out in a liquid phase, as described below. In either approach, the order of addition of reactants can be varied to obtain different information about the compounds being tested.

For example, test compounds that interfere with the interaction between the target gene products and the binding partners, e.g., by competition, can be identified by conducting the reaction in the presence of the test substance; i.e., by adding the test substance to the reaction mixture prior to or simultaneously with the target gene product and interactive cellular or extracellular binding partner. Alternatively, test compounds that disrupt preformed complexes, e.g., compounds with higher binding constants that displace one of the components from the complex, can be tested by adding the test compound to the reaction mixture after complexes have been formed.

In a homogeneous assay, a preformed complex of the target gene product and the interactive cellular or extracellular binding partner product is prepared in which either the target gene products or their binding partners are labeled, but the signal generated by the label is quenched due to complex formation (see, e.g., Rubenstein, U.S. Pat. No. 4,109,496, which uses this approach for immunoassays). The addition of a test substance that competes with and displaces one of the species from the preformed complex will result in the generation of a signal above background. In this way, test substances that disrupt target gene product/cellular or extracellular binding partner interactions can be identified.

In a particular embodiment, the target gene product can be prepared for immobilization using recombinant DNA techniques described above. For example, the target gene coding region can be fused to a glutathione-S-transferase (GST) gene using a fusion vector such as pGEX-5X-1, in such a manner that its binding activity is maintained in the resulting fusion product. The interactive cellular or extracellular product is purified and used to raise a monoclonal antibody, using methods routinely practiced in the art. This antibody can be labeled with the radioactive isotope $^{125}$I, for example, by methods routinely practiced in the art.

In a heterogeneous assay, the GST-Target gene fusion product is anchored, e.g., to glutathione-agarose beads. The interactive cellular or extracellular binding partner is then added in the presence or absence of the test compound in a manner that allows interaction and binding to occur. At the end of the reaction period, unbound material is washed away, and the labeled monoclonal antibody can be added to the system and allowed to bind to the complexed components. The interaction between the target gene product and the interactive cellular or extracellular binding partner is detected by measuring the amount of radioactivity that remains associated with the glutathione-agarose beads. A successful inhibition of the interaction by the test compound will result in a decrease in measured radioactivity.

Alternatively, the GST-target gene fusion product and the interactive cellular or extracellular binding partner can be mixed together in liquid in the absence of the solid glutathione-agarose beads. The test compound is added either during or after the binding partners are allowed to interact. This mixture is then added to the glutathione-agarose beads and unbound material is washed away. Again, the extent of inhibition of the binding partner interaction can be detected by adding the labeled antibody and measuring the radioactivity associated with the beads.

In another embodiment of the invention, these same techniques are employed using peptide fragments that correspond to the binding domains of the target gene product and the interactive cellular or extracellular binding partner (where the binding partner is a product), in place of one or both of the full-length products. Any number of methods routinely practiced in the art can be used to identify and isolate the protein's binding site. These methods include, but are not limited to, mutagenesis of one of the genes encoding one of the products and screening for disruption of binding in a co-immunoprecipitation assay.

In addition, compensating mutations in the gene encoding the second species in the complex can be selected. Sequence analysis of the genes encoding the respective products will reveal mutations that correspond to the region of the product involved in interactive binding. Alternatively, one product can be anchored to a solid surface using methods described above, and allowed to interact with and bind to its labeled binding partner, which has been treated with a proteolytic enzyme, such as trypsin. After washing, a short, labeled peptide comprising the binding domain can remain associated with the solid material, which can be isolated and identified by amino acid sequencing. Also, once the gene coding for the cellular or extracellular binding partner product is obtained, short gene segments can be engineered to express peptide fragments of the product, which can then be tested for binding activity and purified or synthesized.

4.8.4. Assays for Amelioration of Colon Cancer Symptoms

Any of the binding compounds, e.g., those identified in the foregoing assay systems, can be tested for the ability to prevent and/or ameliorate symptoms of tumors and cancers (e.g., colon cancer). Cell-based and animal model-based assays for the identification of compounds exhibiting an ability to prevent and/or ameliorate tumors and cancers symptoms are described below.

First, cell-based systems such as those described in Section 4.7.2, can be used to identify compounds that ameliorate symptoms of tumors and cancers. For example, such cell systems can be exposed to a compound suspected of ameliorating colon tumor or cancer symptoms, at a sufficient concentration and for a time sufficient to elicit such an amelioration in the exposed cells. After exposure, the cells are examined to determine whether one or more tumor or cancer phenotypes has been altered to resemble a more normal or more wild-type, non-cancerous phenotype.

For colon cancer, cell-based systems using the Caco-2 and HT-29 cell lines can be used. Upon exposure to such cell systems, compounds can be assayed for their ability to reduce the cancerous potential of such cells. Further, the level of all gene expression within these cells may be assayed. Presumably, an increase in the observed level of expression of genes 29, 30, 36 (095), 38 (102), 56, 75, 82, 92, 96 (105), and 101, and a decrease in the level of expression of genes 48, 83, 90, 93, and 97, would indicate an amelioration of tumors and cancers (e.g., colon cancer).

In addition, animal models, such as those described, above, in Section 4.7.1, can be used to identify compounds capable of ameliorating symptoms of tumors and cancers. Such animal models can be used as test substrates for the identification of drugs, pharmaceuticals, and therapies which can be effective in treating tumors and cancers. For example, animal models can be exposed to a compound suspected of exhibiting an ability to ameliorate tumor or cancer symptoms, at a sufficient concentration and for a time sufficient to elicit such an amelioration in the exposed animals. The response of the animals to the exposure can be monitored by assessing the reversal of disorders associated with the tumor or cancer. Any treatments which reverse any symptom of tumors and cancers should be considered as candidates for human therapy. Dosages of test agents can be determined by deriving dose-response curves, as discussed in Section 4.10.

Fingerprint patterns can be characterized for known cell states, e.g., normal or known pre-neoplastic (e.g., polyps), neoplastic (e.g., adenomas or adenocarcinomas), or metastatic states, within the cell- and/or animal-based model systems. Subsequently, these known fingerprint patterns can be compared to ascertain the effect a test compound has to modify such fingerprint patterns, and to cause the pattern to more closely resemble that of a normal fingerprint pattern.

For example, administration of a compound can cause the fingerprint pattern of a cancerous model system to more closely resemble a control, normal system. Administration of a compound can, alternatively, cause the fingerprint pattern of a control system to begin to mimic tumors and cancers (e.g., colon cancer).

4.8.5. Monitoring of Effects During Clinical Trials

The influence of compounds on tumors and cancers can be monitored not only in basic drug screening, but also in clinical trials. In such clinical trials, the expression of a panel of genes that has been discovered in any one of the paradigms of Section 4.1.1 can be used as a "read out" of the tumor or cancer state of a particular cell.

For example, in a clinical. trial, tumor cells can be isolated from colon tumors removed by surgery, and RNA prepared and analyzed by Northern blot analysis or RT-PCR as described herein, or alternatively by measuring the amount of protein produced. In this way, the fingerprint profiles can serve as putative biomarkers indicative of colon tumors or cancers. Thus, by monitoring the level of expression of the differentially expressed genes described herein, a protocol for suitable chemotherapeutic anticancer drugs can be developed.

4.9. Compounds and Methods for Treatment of Tumors

Symptoms of tumors and cancers can be ameliorated by, e.g., target gene modulation, and/or by a depletion of the cancerous cells. Target gene modulation can be of a positive or negative nature, depending on the specific situation involved, but each modulatory event yields a net result in which tumor and cancer (e.g., colon cancer) symptoms are ameliorated.

"Negative modulation," as used herein, refers to a reduction in the level and/or activity of target gene product relative to the level and/or activity of the target gene product in the absence of the modulatory treatment. "Positive modulation," as used herein, refers to an increase in the level and/or activity of target gene product relative to the level and/or activity of target gene product in the absence of modulatory treatment.

It is possible that tumors and cancers can be brought about, at least in part, by an abnormal level of gene product, or by the presence of a gene product exhibiting abnormal activity. As such, the reduction in the level and/or activity of such gene products would bring about the amelioration of tumor and cancer symptoms. For example, an increase in the level of expression of gene numbers 048, 083, 090, 093 and 097 correlates with tumors and cancers (e.g., colon cancer). Therefore, a negative modulatory technique that decreases the expression of these genes in tumors and cancers (e.g., colon cancer) should result in a decrease in cancer symptoms.

Alternatively, it is possible that tumors and cancers can be brought about, at least in part, by the absence or reduction of the level of gene expression, or a reduction in the level of a gene product's activity. As such, an increase in the level of gene expression and/or the activity of such gene products would bring about the amelioration of tumors and cancers symptoms. For example, as demonstrated in the Examples presented below, a reduction in the level of expression of gene numbers 029, 030, 036 (095), 038 (102), 056, 075, 082, 092, 095, 096 (105), and 101 correlates with tumors and cancers (e.g., colon cancer). A positive modulatory technique that increases expression of these genes in tumor and cancer cells should, therefore, act to ameliorate the cancer symptoms.

4.9.1. Negative Modulatory Techniques

As discussed above, tumors and cancers can be treated by techniques that inhibit the expression or activity of target gene products. For example, compounds that exhibit negative modulatory activity can be used in accordance with the invention to prevent and/or ameliorate symptoms of tumors and cancers (e.g., colon cancer). Such molecules can include, but are not limited to peptides, phosphopeptides, small organic or inorganic molecules, or antibodies (including, for example, polyclonal, monoclonal, humanized, anti-idiotypic, chimeric or single chain antibodies, and FAb, F(ab')$_2$ and FAb expression library fragments, and epitope-binding fragments thereof).

Further, antisense and ribbzyme molecules that inhibit expression of the target gene can also be used to reduce the level of target gene expression, thus effectively reducing the level of target gene activity. Still further, triple helix molecules can be used in reducing the level of target gene activity.

4.9.1.1. Negative Modulatory Antisense, Ribozyme and Triple Helix Approaches Compounds that can prevent and/or ameliorate symptoms of tumors and cancers include antisense, ribozyme, and triple helix molecules. Such molecules can be designed to reduce or inhibit either wild type, or if appropriate, mutant target gene activity. For example, anti-sense RNA and DNA molecules act to directly block the translation of TmRNA by hybridizing to targeted mRNA and preventing protein translation. With respect to antisense DNA, oligodeoxyribonucleotides derived from the translation initiation site, e.g., between the −10 and +10 regions of the target gene nucleotide sequence of interest, are preferred.

Ribozymes are enzymatic RNA molecules capable of catalyzing the specific cleavage of RNA. For a review, see, for example, Rossi, *Current Biology*, 4:469–471 (1994). The mechanism of ribozyme action involves sequence-specific hybridization of the ribozyme molecule to complementary target RNA, followed by an endonucleolytic cleavage. A composition of ribozyme molecules must include one or more sequences complementary to the target gene mRNA, and must include a well-known catalytic sequence responsible for mRNA cleavage. For this sequence, see U.S. Pat. No. 5,093,246, which is incorporated by reference herein in its entirety. As such, the present invention includes engineered hammerhead motif ribozyme molecules that specifically and efficiently catalyze endonucleolytic cleavage of RNA sequences encoding target gene proteins.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site can be evaluated for predicted structural features, such as secondary structure, that can render an oligonucleotide sequence unsuitable. The suitability of candidate sequences can also be evaluated by testing their accessibility to hybridization with complementary oligonucleotides, using ribonuclease protection assays.

Nucleic acid molecules in triple helix formations used to inhibit transcription should be single-stranded and composed of deoxynucleotides. The base composition of these oligonucleotides must be designed to promote triple helix formation via Hoogsteen base pairing rules, which generally require sizeable stretches of either purines or pyrimidines on one strand of a duplex. Nucleotide sequences can be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molecules can be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation can be increased by creating a so called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines on one strand of a duplex.

In instances wherein the antisense, ribozyme, and/or triple helix molecules described herein are used to reduce or inhibit mutant gene expression, it is possible that they can also efficiently reduce or inhibit the transcription (triple helix) and/or translation (antisense, ribozyme) of mRNA produced by normal target gene alleles such that the concentration of normal target gene product present can be lower than is necessary for a normal phenotype. In such cases, to ensure that substantially normal levels of target gene activity are maintained, nucleic acid molecules that encode and express target gene polypeptides exhibiting normal target gene activity can be introduced into cells via gene therapy methods such as those described herein that do not contain sequences susceptible to whatever antisense, ribozyme, or triple helix treatments are being used. Alternatively, when the target gene encodes an extracellular protein, it may be preferable to coadminister normal target gene protein into the cell or tissue to maintain the requisite level of cellular or tissue target gene activity.

Anti-sense RNA and DNA, ribozyme, and triple helix molecules of the invention can be prepared by standard methods known in the art for the synthesis of DNA and RNA molecules. These include techniques for chemically synthesizing oligodeoxyribonucleotides and oligoribonucleotides well known in the art such as, for example, solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors which also include suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules can be introduced as a means of increasing intracellular stability and half-life. Possible modifications include, but are not limited to, the addition of flanking sequences of ribo- or deoxy- nucleotides to the 5' and/or 3' ends of the molecule, or the use of phosphorothioate or 2' O-methyl rather than phospho-diesterase linkages within the oligodeoxyribonucleotide backbone.

4.9.1.2. Neqative Modulatory Antibody Techniques

Antibodies can be generated which are both specific for a target gene product and which reduce target gene product activity. Therefore, such antibodies can be administered when negative modulatory techniques are appropriate for the treatment of tumors and cancers (e.g., colon cancer). Antibodies can be generated using standard techniques described in Section 4.6, against the proteins themselves or against peptides corresponding to portions of the proteins.

In instances where the target gene protein to which the antibody is directed is intracellular, and whole antibodies are used, internalizing antibodies are preferred. However, lipofectin or liposomes can be used to deliver the antibody, or a fragment of the Fab region which binds to the target gene epitope, into cells. Where fragments of an antibody are used, the smallest inhibitory fragment which specifically binds to the target protein's binding domain is preferred. For example, peptides having an amino acid sequence corresponding to the domain of the variable region of the antibody that specifically-binds to the target gene protein can be used. Such peptides can be synthesized chemically or produced by recombinant DNA technology using methods well known in the art (e.g., see Creighton, 1983, supra; and Sambrook et al., 1989, supra).

Alternatively, single chain neutralizing antibodies that bind to intracellular target gene product epitopes can also be administered. Such single chain antibodies can be administered, for example, by expressing nucleotide sequences encoding single-chain antibodies within the target cell population by using, for example, techniques such as those described in Marasco et al. *Proc. Natl. Acad. Sci. USA*, 90:7889–7893 (1993).

When the target gene protein is extracellular, or is a transmembrane protein, any of the administration techniques described in Section 4.10 which are appropriate for peptide administration can be used to effectively administer inhibitory target gene antibodies to their site of action.

4.9.2. Positive Modulatory Techniques

As discussed above, tumor and cancer symptoms also can be treated by increasing the level of target gene expression or by increasing the activity of a target gene product. For example, a target gene protein can be administered to a patient at a level sufficient to ameliorate tumor and cancer (e.g., lung or colon cancer) symptoms. Any of the techniques discussed in Section 4.10, can be used for such administration. One of skill in the art will know how to determine the concentration of effective, non-toxic doses of the normal target gene protein, using techniques such as those described in Section 4.10.1.

Where the compound to be administered is a peptide, DNA sequences encoding the peptide can, alternatively, be directly administered to a patient exhibiting tumor or cancer symptoms, at a concentration sufficient to generate the production of an amount of target gene product adequate to ameliorate the tumor or cancer symptoms. Any techniques that achieve intracellular administration can be used for the administration of such DNA molecules.

DNA molecules that encode peptides that act extracellularly can be taken up and expressed by any cell type, so long as a sufficient circulating concentration of peptide results in a reduction in tumor or cancer symptoms. DNA molecules that encode peptides that act intracellularly must be taken up and expressed by cells involved in the tumors and cancers at a sufficient level to bring about the reduction of tumor or cancer symptoms.

Further, patients can be treated for symptoms of tumors or cancers by gene replacement therapy. One or more copies of a normal target gene, or a portion of the gene that directs the production of a normal target gene protein with target gene function, can be inserted into cells, using vectors that include, but are not limited to, adenovirus, adeno-associated virus, and retrovirus vectors, in addition to other particles that introduce DNA into cells, such as liposomes. Techniques such as those described above can be utilized for the introduction of normal target gene sequences into human cells.

In instances wherein the target gene encodes an extracellular, secreted gene product, such gene replacement techniques may be accomplished either in vivo or in vitro. For such cases, the cell type expressing the target gene is less important than achieving a sufficient circulating concentration of the extracellular molecules to ensure amelioration of tumor and cancer symptoms. In vitro, target gene sequences can be introduced into autologous cells. Those cells expressing the target gene sequence of interest can then be reintroduced, preferably by intravenous administration, into the patient such that there results an amelioration of tumor and cancer symptoms.

In instances wherein the gene replacement involves a gene that encodes a product which acts intracellularly, it is preferred that gene replacement be accomplished in vivo. Further, because the cell type in which the gene replacement must occur is the cell type involved in a tumor or cancer, such techniques must successfully target tumor and cancer cells.

Taking the 082 gene as an example, an increase in gene expression can serve to ameliorate tumor and cancer, e.g., colon cancer, symptoms. Therefore, any positive modulation described herein that increases the 082 gene product or gene product activity to a level sufficient to ameliorate tumor and cancer symptoms represents a successful tumor and cancer therapeutic treatment.

4.10. Pharmaceutical Preparations and Methods of Administration

The identified compounds that inhibit target gene expression, synthesis, and/or activity can be administered to a patient at therapeutically effective doses to prevent, treat, or ameliorate a tumor or cancer. A therapeutically effective dose refers to that amount of the compound sufficient to result in a viable or measurable decrease in tumor or cancer symptoms.

4.10.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to uninfected cells and, thereby, reduce side effects.

The data obtained from the cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any compound used in the method of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography.

4.10.2. Formulations and Use

Pharmaceutical compositions for use in the present invention can be formulated by standard techniques using one or more physiologically acceptable carriers or excipients.

Thus, the compounds and their physiologically acceptable salts and solvates can be formulated for administration by inhalation or insufflation (either through the mouth or the nose, or oral, buccal, parenteral, or rectal administration.

For oral administration, the pharmaceutical compositions can take the form of tablets or capsules prepared by conventional means with pharmaceutically acceptable excipients such as binding agents, e.g., pregelatinised maize starch, polyvinylpyrrolidone, or hydroxypropyl methylcellulose; fillers, e.g., lactose, microcrystalline cellulose, or calcium hydrogen phosphate; lubricants, e.g., magnesium stearate, talc, or silica; disintegrants, e.g., potato starch or sodium starch glycolate; or wetting agents, e.g., sodium lauryl sulphate. The tablets can be coated by methods well known in the art.

Liquid preparations for oral administration can take the form of solutions, syrups, or suspensions, or they can be presented as a dry product for constitution with water or other suitable vehicle before use. Such liquid preparations can be prepared by conventional means with pharmaceutically acceptable additives such as suspending agents, e.g., sorbitol syrup, cellulose derivatives, or hydrogenated edible fats; emulsifying agents, e.g., lecithin or acacia; non-aqueous vehicles, e.g., almond oil, oily esters, ethyl alcohol, or fractionated vegetable oils; and preservatives, e.g., methyl or propyl-p-hydroxybenzoates or sorbic acid. The preparations can also contain buffer salts, flavoring, coloring, and/or sweetening agents as appropriate.

Preparations for oral administration can be suitably formulated to give controlled release of the active compound.

For administration by inhalation, the compounds are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions, or emulsions in oily or aqueous vehicles, and can contain formulatory agents such as suspending, stabilizing, and/or dispersing agents. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration.

4.11. Diaqnosis of Tumors or Cancers

A variety of methods can be employed to diagnose tumors and cancers, e.g., lung, liver, or colon cancer. Such methods can, for example, use reagents such as fingerprint gene nucleotide sequences or antibodies directed against differentially expressed and pathway gene peptides. Specifically, such reagents can be used for the detection of the presence of target gene mutations, or the detection of either over- or under-expression of a target gene in RNA.

4.11.1. Detection of Fingerprint Gene Nucleic Acids

DNA or RNA from the cell type or tissue to be analyzed can be easily isolated using standard procedures. Diagnostic procedures can also be performed "in situ" directly upon tissue sections (fixed and/or frozen) of patient tissue obtained from biopsies or resections, such that no nucleic acid purification is necessary. Nucleic acid reagents such as those described herein can be used as probes and/or primers for such in situ procedures (see, for example, Nuovo, G. J., *PCR in situ hybridization: Protocols and Applications*, Raven Press, N.Y., 1992).

Fingerprint gene nucleotide sequences, either RNA or DNA, can, for example, be used in hybridization or amplification assays of biological samples to detect gene structures and expression associated with tumors and cancers, e.g., colon cancer. Such assays can include, but are not limited to, Southern or Northern analyses, single stranded conformational polymorphism analyses, in situ hybridization assays, and polymerase chain reaction analyses. Such analyses can reveal both quantitative aspects of the expression pattern of a fingerprint gene, and qualitative aspects of the fingerprint gene expression and/or gene composition. That is, such techniques can include, for example, point mutations, insertions, deletions, chromosomal rearrangements, and/or activation or inactivation of gene expression.

Preferred diagnostic methods for the detection of fingerprint gene-specific nucleic acid molecules involve contacting and incubating nucleic acids derived from the cell type or tissue being analyzed with one or more labeled nucleic acid reagents, under conditions favorable for the specific annealing of these reagents to their complementary sequences within the nucleic acid molecule of interest. Preferably, the lengths of these nucleic acid reagents are at least 15 to 30 nucleotides. After incubation, all non-annealed nucleic acids are removed from the nucleic acid:fingerprint RNA molecule hybrid. The presence of nucleic acids from the target tissue which have hybridized, if any such molecules exist, is then detected. Using such a detection scheme, the nucleic acid from the tissue or cell type of interest can be immobilized, for example, to a solid support such as a membrane, or a plastic surface such as that on a microtitre plate or polystyrene beads. In this case, after incubation, non-annealed, labeled fingerprint nucleic acid reagents are easily removed. Detection of the remaining, annealed, labeled nucleic acid reagents is accomplished using standard techniques.

Alternative diagnostic methods for the detection of fingerprint gene specific nucleic acid molecules can involve their amplification, e.g., by PCR (see Mullis, U.S. Pat. No. 4,683,202, 1987), ligase chain reaction (Barany, *Proc. Natl. Acad. Sci. USA*, 88:189–193, 1991), self-sustained sequence replication (Guatelli et al., *Proc. Natl. Acad. Sci. USA*, 87:1874–1878, 1990), transcriptional amplification system (Kwoh et al., *Proc. Natl. Acad. Sci. USA*, 86:1173–1177, 1989), Q-Beta replicase (Lizardi et al., *Bio/Technology*, 6:1197, 1988), or any other nucleic acid amplification method, followed by the detection of the amplified molecules using standard techniques. These detection schemes are especially useful for the detection of nucleic acid molecules if such molecules are present in very low numbers.

In one embodiment of such a detection scheme, a cDNA molecule is obtained from an RNA molecule of interest, e.g., by reverse transcription of the RNA molecule into cDNA. Cell types or tissues from which such RNA can be isolated include any tissue in which a wild type fingerprint gene is known to be expressed. A sequence within the cDNA is then used as the template for a nucleic acid amplification reaction, such as a PCR amplification reaction, or the like. The nucleic acid reagents used as synthesis initiation reagents, e.g., primers, in the reverse transcription and nucleic acid amplification steps of this method are chosen from among the fingerprint gene nucleic acid reagents describe above. The preferred lengths of such nucleic acid reagents are at least 19–30 nucleotides. For detection of the amplified product, the nucleic acid amplification can be performed using labeled nucleotides. Alternatively, enough amplified product can be made such that the product can be visualized by standard ethidium bromide staining or by utilizing any other suitable nucleic acid staining method.

In addition to methods that focus primarily on the detection of one nucleic acid sequence, fingerprint profiles can also be assessed in such detection schemes.

4.11.2. Detection of Target Gene Peptides

Antibodies directed against wild type or mutant fingerprint gene peptides can also be used, e.g., in immunoassays, for tumor and cancer diagnostics and prognostics. Such diagnostic methods can be used to detect abnormalities in the level of fingerprint gene protein expression, or abnormalities in the structure and/or tissue, cellular, or subcellular location of fingerprinting gene protein. Structural differences can include, for example, differences in the size, electronegativity, or antigenicity of the mutant fingerprint gene protein relative to the normal fingerprint gene protein.

Protein from the tissue or cell type to be analyzed can easily be isolated using standard techniques, e.g., as described in Harlow and Lane, *Antibodies: A Laboratory Manual* (Cold Spring Harbor Laboratory Press, Cold Spring Harbor, N.Y. 1988).

For example, antibodies, or fragments of antibodies, such as those described herein, can be used to quantitatively or qualitatively detect the presence of wild type or mutant fingerprint gene peptides. This can be accomplished, for example, by immunofluorescence techniques employing a fluorescently labeled antibody (see below) coupled with light microscopic, flow cytometric, or fluorimetric detection. Such techniques are especially preferred if the fingerprint gene peptides are expressed on the cell surface.

The antibodies (or fragments thereof) useful in the present invention can, additionally, be employed histologically, as in immunofluorescence or immunoelectron microscopy, for in situ detection of target gene peptides. In situ detection can be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the fingerprint gene peptides, but also their distribution in the examined tissue. Using the present invention, those of ordinary skill will readily perceive that any of a wide variety of histological methods (such as staining procedures) can be modified to achieve such in situ detection.

Immunoassays for wild type or mutant fingerprint gene peptides typically comprise incubating a biological sample, such as a biological fluid, a tissue extract, freshly harvested cells, or cells which have been incubated in tissue culture, in the presence of a detectably labeled antibody capable of identifying fingerprint gene peptides, and detecting the bound antibody by any of a number of techniques well-known in the art.

The biological sample can be brought in contact with and immobilized on a solid phase support or carrier such as nitrocellulose, or other solid support which is capable of immobilizing cells, cell particles, or soluble proteins. The support can then be washed with suitable buffers followed by treatment with the detectably labeled fingerprint gene specific antibody. The solid phase support can then be washed with the buffer a second time to remove unbound antibody. The amount of bound label on the solid support can then be detected by conventional means.

One of the ways in which the fingerprint gene peptide-specific antibody can be detectably labeled is by linking the same to an enzyme, e.g., horseradish peroxidase, alkaline phosphatase, or glucoamylase, and using it in an enzyme immunoassay (EIA) (see, e.g., Voller, A., "The Enzyme Linked Immunosorbent Assay (ELISA)," *Diagnostic Horizons*, 2:1–7 (1978); Voller et al., *J. Clin. Pathol.*, 31:507–520 (1978); Butler, J. E., *Meth. Enzymol.*, 73:482–523 (1981); Maggio, E. (ed.), *Enzyme Immunoassay* (CRC Press, Boca Raton, Fla., 1980); Ishikawa et al. (eds.), *Enzyme Immunoassay* (Kgaku Shoin, Tokyo, 1981)). The enzyme bound to the antibody will react with an appropriate substrate, preferably a chromogenic substrate, in such a manner as to produce a chemical moiety that can be detected, for example, by spectrophotometric, fluorimetric or by visual means.

5. EXAMPLE

Identification and Characterization of Novel Genes That Inhibit or Induce Tumors or Cancer In this Example, the "specimen paradigm" described above was used to identify a number of genes, designated herein as numbered genes, that are differentially expressed in colon cancer cells compared to normal colon cells. Specifically, gene numbers 048, 083, 090, 093, and 097 are expressed in colon cancer cells at a rate which is many-fold higher than they are expressed in normal colon cells, and gene numbers 029, 030, 036, 038, 056, 075, 082, 092, 095, 096, and 101 are expressed in normal colon cells at a rate that is many-fold higher than they are expressed in cancerous colon cells. Given the differential gene expression patterns revealed in this Section, the products of this second set of genes represent peptides having tumor suppressor or inhibitor function.

5.1. Materials and Methods
5.1.1. Differential Display

Differential mRNA display was carried out as described above. Details of the differential display are given below.
RNA Isolation Primary colon tumors and adjacent normal colon tissue were obtained as surgical biopsies from twelve independent colon cancer patients. These samples were snap frozen in liquid nitrogen and stored at −80° C. until used for RNA extraction. Total RNA was extracted from these samples using RNAzol. Isolated RNA was resuspended in DEPC treated dH$_2$O and quantitated by spectrophotometry at OD$_{260}$. An aliquot of each RNA sample was then treated with RNAse-free DNAse I to remove contaminating chromosomal DNA. Fifty μg of RNA in 50 μl DEPC-treated dH$_2$O were mixed with 5.7 μl 10×PCR buffer (Perkin-Elmer/Cetus) and 1 μl RNAse inhibitor (40 units/μl; Boehringer Mannheim, Germany). After addition of 2 μg RNAse-free DNAse I (10 units/μl; Boehringer Mannheim, Germany), the reaction was incubated for 30 minutes at 37° C. The total volume was brought to 200 μl with DEPC-treated dH$_2$O and extracted once with phenol/chloroform. The treated RNA sample was then precipitated by addition of 20 μl 3M NaOAc, pH 4.8, and 500 μl absolute ETOH, followed by incubation on dry ice for one hour. RNA was collected by centrifugation for 15 minutes and washed once with 75% ETOH. The pellet was dried and resuspended in 50 μl DEPC treated dH$_2$O.

First Strand cDNA Synthesis

For each sample, 2 μg of RNA in a total volume of 10 μl were added to 2 μl of T11GG 3' primer (10 mM; Operon). The mixture was incubated at 70° C. for 10 minutes to denature the RNA and then placed on ice. The following components were added to each denatured RNA/primer sample: 4 μl 5×First Strand Buffer (Gibco/BRL, Gaithersburg, Md.), 2 μl 0.1 M DTT (Gibco/BRL), 1 μl RNAse inhibitor (40 units/μl; Boehringer Mannheim), 2 μl 200 mM dNTP mix (diluted from 20 mM stock; Pharmacia), and 1 μl SuperScript reverse transcriptase (200 units/μl; Gibco/BRL). The reactions were gently mixed and incubated for 30 minutes at 42° C., and then 5 minutes at 85° C. Samples were diluted ten-fold in dH$_2$O before use in PCR.

PCR Reactions

The diluted first strand cDNAs were used as PCR templates for matched pairs of normal and tumor samples from eight independent patients. Specifically, 13 μl of reaction mix was added to each tube of a 96 well plate on ice. The reaction mix contained 6.4 μl H$_2$O, 2 μl 10×PCR Buffer (Perkin-Elmer), 2 μl 20 μM dNTPs, 0.4 μl $^{35}$S OATP (12.5 μCi/μl; 50 μCi total, Dupont/NEN) or 1.0 μl $^{33}$P dATP (10.0 μCi/μl; Dupont/NEN), 2 μl 5' primer OPE4 (5'GTGACATGCC-3'; 10 μM; Operon), and 0.2 μl AmpliTaq™ Polymerase (5 units/μl; Perkin-Elmer). Next, 2 μl of 3' primer (T$_{11}$CC, 10 μM) were added to the side of each tube, followed by 5 μl of cDNA, also to the sides of the tubes, which were still on ice. Tubes were capped and mixed, and brought up to 1000 rpm in a centrifuge, then immediately returned to ice. A Perkin-Elmer 9600 or MJ Research PTC-200 thermal cycler was used, and programmed as follows:

| | |
|---|---|
| 94° C. | 2 min. |
| *94° C. | 15 sec. |
| *40° C. | 2 min.    * = x 40 |
| *ramp 72° C. | 1 min. |
| *72° C. | 30 sec. |
| 72° C. | 5 min. |
| 4° C. | hold |

When the thermal cycler initially reached 94° C., the 96 well plate was removed from ice and placed directly into the cycler. Following the amplification reaction, 15 μl of loading dye, containing 80% formamide, 10 mM EDTA, 1 mg/ml xylene cyanole, 1 mg/ml bromphenol blue were added. The loading dye and reaction were mixed, incubated at 85° C. for 5 minutes, cooled on ice, centrifuged, and placed on ice. Approximately 4 μl from each tube was loaded onto a pre-run (60 V) 6% denaturing acrylamide gel. The gel was run at approximately 80V until top dye front was about 1 inch from bottom. The gel was transferred to 3 MM paper (Whatman Paper, England) and dried under vacuum. Bands were visualized by autoradiography.

These cDNA bands are referred to as RADE bands (for Rapid Analysis Differential Expression) and were analyzed to select cDNAs that were present in colon cancer tissue but not normal colon tissue from the same individual, or in normal colon tissue and not colon cancer tissue from the same individual. cDNA bands that were differentially expressed in at least 4 of the 8 matched normal/tumor pairs (>50%) were identified for further characterization.

5.1.2. Other Techniques Amplified cDNA Band Isolation and Amplification

PCR bands determined to be of interest in the differential display analysis were recovered from the gel and reamplified.

Briefly, differentially expressed bands were excised from the dried gel with a razor blade and placed into a microfuge tube with 100 µl $H_2O$ and heated at 100° C. for 5 minutes, vortexed, heated again to 100° C. for 5 minutes, and vortexed again. After cooling, 100 µl $H_2O$, 20 µl 3M NaOAc, 1 µl glycogen (20 mg/ml), and 500 µl ethanol were added and the sample was precipitated on dry ice. After centrifugation, the pellet was washed and resuspended in 10 µl $H_2O$.

DNA isolated from the excised differentially expressed bands were then reamplified by PCR using the following reaction conditions:

| | |
|---|---|
| 5 µl | $H_2O$ |
| 10 µl | 10x PCR Buffer (see above) |
| 10 µl | 200 µM dNTPs |
| 10 µl | 10 µM 3' primer (see above) |
| 10 µl | 10 µM 5' primer (see above) |
| 1.5 µl | amplified band |
| 0.5 µl | AmpliTaq ® polymerase (5 units/µl) |

PCR conditions were the same as the initial conditions used to generate the original amplified band, as described, above. After reamplification, glycerol loading dyes were added and samples were loaded onto a 2% preparative TAE/Biogel (Bio101, La Jolla, Calif.) agarose gel and eluted. Bands were then excised from the gel with a razor blade and vortexed for 15 minutes at r.t., and purified using the Mermaid™ kit from Bio101 by adding 3 volumes of Mermaid™ high salt binding solution and 8 µl of resuspended glassfog in a microfuge tube. Glassfog was then pelleted, washed 3 times with ethanol wash solution, and then DNA was eluted twice in 10 µl at 50° C.

Direct Sequencing of Isolated, Amplified cDNA Bands

Each gel-purified PCR-amplified cDNA band was directly sequenced using the T11GG 3' primer and/or the arbitrary 10 mer 5' primer as sequencing primers with the fmol sequencing kit (Promega). The sequencing primers were end labelled by adding 10 pmol of each primer to 1 µl of 10xpolynucleotide kinase buffer (Promega), 1 µl of P33-γ-ATP (10 mCi/µl, NEN), and 1 µl of polynucleotide kinase (10 units/µl; Promega) in a total volume of 10 µl. The reactions were incubated for 30 minutes at 37° C. followed by a 5 minute incubation at 95° C. to inactivate the PNK enzyme. For each sequencing reaction the following components were mixed together: 0.5–1 ng of isolated, amplified cDNA band, 5 µl of 5xfmol buffer (Promega), 1.5 µl of end-labeled primer, $H_2O$ to a volume of 16 µl, and then 1 µl of sequencing grade Taq DNA polymerase (5 units/µl; Promega). Four µl of this sequencing reaction mix were added to each of the four wells of a microtiter plate containing 2 µl of ddNTP termination mix (ddA, ddC, ddG, and ddT; Promega). The plate of PCR sequencing reactions was briefly centrifuged at 500xg to collect the reactions at the bottom of the wells, and then subjected to the following conditions:

| | | |
|---|---|---|
| 95° C. | 2 minutes | |
| *95° C. | 30 seconds | * = x 30 |
| *40° C. | 1 minute and 30 seconds | |
| *70° C. | 1 minute | |
| 4° C. | Hold indefinitely | |

The reactions were terminated by the addition of 4 µl of formamide stop solution (Promega), and denatured by heating at 80° C. for five minutes. The samples were electorphoresed at 60 Watts on an 8% acrylamide/urea sequencing gel until the bromophenol blue dye front reached the bottom of the gel. The gel was transferred to 3 MM Whatmann Chromotography paper and dried. The dried gel was exposed to X-ray film (Kodak) for 16 hours at room temperature. The sequence was determined by manual reading of the sequencing gel.

Subcloning and Sequencing

The TA cloning kit (Invitrogen, San Diego, Calif.) was used to subclone the amplified bands. The ligation reaction typically consisted of 4 µl sterile $H_2O$, 1 µl ligation buffer, 2 µl TA cloning vector, 2 µl PCR product, and 1 µl T4 DNA ligase. The volume of PCR product can vary, but the total volume of PCR product plus $H_2O$ was always 6 µl. Ligations (including vector alone) were incubated overnight at 12° C. before bacterial transformation. TA cloning kit competent bacteria (INVαF': enda1, recAl, hsdRl7(r−k, m+k), supE44, λ-, thi-1, gyrA, relA1, φ80lacZαΔM15Δ(lacZYA-argF), deoR+, F') were thawed on ice and 2 µl of 0.5 M β-mercaptoethanol were added to each tube. Two µl from each ligation were added to each tube of competent cells (50 µl), mixed without vortexing, and incubated on ice for 30 minutes. Tubes were then placed in 42° C. bath for exactly 30 sec., before being returned to ice for 2 minutes. Four hundred-fifty µl of SOC media (Sambrook et al., 1989, supra) were then added to each tube which were then shaken at 37° C. for 1 hour. Bacteria were then pelleted, resuspended in approximately 200 µl SOC and plated on Luria broth agar plates containing X-gal and 60 µg/µl ampicillin and incubated overnight at 37° C. White colonies were then picked and screened for inserts using PCR.

A master mix containing 2 µl 10xPCR buffer, 1.6 µl 2.5 mM dNTP's, 0.1 µl 25 MM $MgCl_2$, 0.2 µl M13 reverse primer (100 ng/µl), 0.2 µl M13 forward primer (100 ng/µl), 0.1 µl AmpliTaq® (Perkin-Elmer), and 15.8 µl $H_2O$ was made. Forty µl of the master mix were aliquoted into tubes of a 96 well plate, and whole bacteria were added with a pipette tip prior to PCR. The thermal cycler was programmed for insert screening as follows:

| | | |
|---|---|---|
| 94° C. | 2 min. | |
| *94° C. | 15 sec. | |
| *47° C. | 2 min. | * = x 35 |
| *ramp 72° C. | 30 sec. | |
| *72° C. | 30 sec. | |
| 72° C. | 10 min. | |
| 4° C. | hold | |

Reaction products were eluted on a 2% agarose gel and compared to vector control. Colonies with vectors containing inserts were purified by streaking onto LB/Amp plates. Vectors were isolated from such strains and subjected to sequence analysis, using an Applied Biosystems Automated Sequencer (Applied Biosystems, Inc. Seattle, Wash.).

Northern Analysis

Northern analysis was performed to confirm the differential expression of the genes corresponding to the amplified bands, as described below.

Twelve μg of total RNA sample, 1.5×RNA loading dyes (60% formamide, 9% formaldehyde, 1.5×MOPS, 0.075% XC/BPB dyes) at a final concentration of 1× and $H_2O$ to a final volume of 40 μl were mixed. The tubes were heated at 65° C. for 5 minutes and then cooled on ice. The RNA samples analyzed were loaded onto a denaturing 1% agarose gel. The gel was run overnight at 32V in 1×MOPS buffer.

A 300 μl denaturing 1% agarose gel was made as follows. Three grams of agarose (SeaKem™ LE, FMC BioProducts, Rockland, Me.) and 60 μl of 5×MOPS buffer (0.1M MOPS [pH 7.0], 40 mM NaOAc, 5 mM EDTA [pH 8.0]) were added to 210 μl sterile $H_2O$. The mixture was heated until melted, then cooled to 50° C., at which time 5 μl ethidium bromide (5 mg/μl) and 30 μl of 37% formaldehyde were added to the melted gel mixture. The gel was swirled quickly to mix, and then poured immediately.

After electrophoresis, the gel was photographed with a fluorescent ruler, then was washed three times in DEPC $H_2O$, for 20 minutes per wash, at room temperature, with shaking. The RNA was then transferred from the gel to Hybond-N® membrane (Amersham), according to the methods of Sambrook et al., 1989, supra, in 20×SSC overnight.

The probes used to detect mRNA were typically synthesized as follows: 2 μl amplified cDNA band (~30 ng), 7 μl $H_2O$, and 2 μl 10×Hexanucleotide mix (Boehringer-Mannheim) were mixed and heated to 95° C. for 5 minutes, and then allowed to cool on ice. The volume of the amplified band can vary, but the total volume of the band plus $H_2O$ was always 9 μl. 3 μl dATP/dGTP/dTTP mix (1:1:1 of 0.5 mM each), 5 μl $\alpha^{32}P$ dCTP 3000 Ci/mM (50 μCi total; Amersham, Arlington Heights, Ill.), and 1 μl Klenow (2 units; Boehringer-Mannheim) were mixed and incubated at 37° C. After 1 hour, 30 μl TE were added and the reaction was loaded onto a Biospin-6™ column (Biorad, Hercules, Calif.), and centrifuged. A 1 μl aliquot of eluate was used to measure incorporation in a scintillation counter with scintillant to ensure that $10^6$ cpm/μl of incorporation was achieved.

For pre-hybridization, the blot was placed into a roller bottle containing 10 ml of rapid-hyb solution (Amersham), and placed into 65° C. incubator for at least 1 hour. For hybridization, 1×$10^7$ cpm of the probe was then heated to 95° C., chilled on ice, and added to 10 ml of rapid-hyb solution. The prehybridization solution was then replaced with probe solution and incubated for 16 hours at 65° C. The following day, the blot was washed once for 20 minutes at room temperature in 2×SSC/0.1% SDS and twice for 15 minutes at 65° C. in 0.1×SSC/0.1% SDS before being covered in plastic wrap and put down for exposure.

In other Northern assays, 20 μg of total RNA per sample was run on a 0.9% agarose gel containing 7% formaldehyde. Following electrophoresis, the gel was rinsed in 20×SSC and then the RNA was transferred to Hybond N+ membrane (Amersham) in 20×SSC overnight. The filter was prehybridized in 7% SDS, 0.5 M $NaHPO_4$, 1 mM EDTA, 1% BSA at 65°, then hybridized overnight in the same solution containing 25 ng of probe fragment labeled with the Prime-It Kit (Stratagene) and $^{32}P$ dCTP. The filter was then washed at 65° with three changes of 1% SDS, 40 mM $NaHPO_4$, 1 mM EDTA, blotted dry, and exposed to Hyperfilm (Amersham) at 80° with intensifying screens.

Chromosomal Mapping

DNAs isolated from 24 human/rodent somatic cell hybrids (Coriell Cell Repositories) were used for PCR templates. Each somatic cell hybrid DNA contains one human chromosome, although the entire chromosome may not be represented. A pair of oligonucleotide 20 mer primers were generated for each cDNA sequence for use in PCR; those oligonucleotide pairs which could amplify a product of the predicted size from human DNA templates were tested against the somatic cell hybrid DNA panel. Thirty nanograms of each hybrid DNA sample (and parental cell DNA samples) were mixed with 20 pmoles each cDNA specific oligonucleotide primers, 3 μl 10×PCR buffer (Perkin-Elmer), 2 μl of 2 μM dNTPs (DATP, dCTP, dGTP, dTTP), and 1 μl AmpliTaq™ polymerase (5 units/μl) in a total volume of 30 μl. Reactions were subjected to the following conditions:

| | | |
|---|---|---|
| 95° C. | 2 min. | |
| *95° C. | 20 sec. | |
| *Tm − 5° C. | 1 min. | * = x 30 cycles |
| *72° C. | 30 sec. | |
| *72° C. | 5 min. | |
| 4° C. | hold | | and then the products were resolved on 2% agarose gels. Primers which gave a band of the correct size in the human DNA control and only one of the hybrid DNA samples was scored as a positive result and the cDNA mapped to the human chromosome contained in that somatic cell hybrid.

5.2. Results

To identify and isolate genes potentially involved in human colorectal carcinoma, differences in gene expression between normal colon cells and colon tumor (adenocarcinomas) cells were examined by differential display. Total RNA was isolated from frozen surgical specimens of normal colons and colon tumors. The RNA samples were treated with RNAse-free DNAse I, reverse transcribed, and used for differential display analysis as described in Materials and Methods. Matched pairs of normal and tumor samples from eight independent patients were compared. PCR was performed on each cDNA sample using 228 separate arbitrary 10-mer 5' primers in combination with the T11GG 3' primer, and the reaction products were separated on a denaturing sequencing gel and autoradiographed. In a typical comparison of one such primer pair, the eight normal colon PCR samples were run side by side, followed by the eight colon tumor PCR samples. cDNA bands which showed differential expression in at least 4 of the 8 matched normal/tumor pairs (>50%) were identified for further characterization.

One hundred and seven separate bands meeting the above criteria were excised and reamplified. The reamplified bands were directly sequenced with the fmol kit; they were also subcloned into the pCRII vector (Invitrogen) and sequenced as described in Materials and Methods. Pairs of oligonucleotide 20 mer primers based on the sequence of the cDNAs were generated and used for RT-PCR to confirm the expression pattern seen during differential display. After such analysis, 18 cDNA bands were chosen for further characterization. Two sequences appeared twice (038 and 102, and 096 and 105), each independently isolated with two different primer pairs, and are considered as one cDNA sequence, each pair corresponding to one gene (038 and 096). Another pair of sequences (036 and 095) was later shown to be part of the same gene (herein gene 036; described in Section 7). Thus, 16 separate cDNA sequences and 15 genes are discussed below. The cDNA sequences of the differential display patterns of the RADE bands are presented in FIGS. 1a to 1p.

Table 1 shows that five of the cDNA sequences have increased expression in colon tumor RNA samples as compared to normal colon RNA samples, while ten sequences were more prominent in normal colon RNA. These tumor-specific genes are potentially useful for diagnostic purposes, and their gene products may be involved in tumor formation or progression, thereby making them potential therapy targets. Loss of gene expression can also lead to carcinogenesis, as has been demonstrated for many tumor suppressor genes. In such cases, replacement of the missing gene product can reverse the transformed phenotype.

Eleven cDNA sequences corresponding to ten genes showed higher expression in normal colon versus colon tumor RNA samples (Table 1), and are therefore candidate tumor suppressor genes. The 16 cDNA sequences were further characterized by Northern analysis, mapping to human chromosomes, and full-length cDNA isolation. The summarized data for each sequence are presented in Table 1.

Table 1 shows summarized data for genes with homologies to known genes, and genes with novel sequences. In the table, numbers in parenthesis in the "RT-PCR" column show the number of positive samples, i.e., samples that confirmed the results of the expression pattern in the differential display specimen paradigm, over the number of total samples (8 or 12) assayed. When relevant, the number/name of the human chromosome to which the cDNA band maps is given.

Longer cDNA sequences from genes 082 (SEQ ID NO:17, FIG. 2), 048 (SEQ ID NO:19, FIG. 3), 090 (SEQ ID NO:20, FIG. 4), 093 (SEQ ID NO:21, FIG. 5), 036 (described in greater detail in Section 7), and 101 (SEQ ID NO:22, FIG. 6) were obtained. In particular, cDNA SEQ ID NO:17 was obtained from human heart cDNA libraries (Stratagene and Clontech), and cDNA SEQ ID NO:22 was obtained from a human prostate cDNA library (Clontech).

A BLASTN (Altschul et al., *J. Mol. Biol.*, 215:403–410, 1990) database search was performed with the nucleotide sequences SEQ ID NO:2 (030), SEQ ID NO:6 (056), SEQ ID NO:8 (082), SEQ ID NO:14 (096), SEQ ID NO:15 (097), and SEQ ID NO:3 (036). A BlastX database search was performed with the nucleotide sequence SEQ ID NO:8 (082).

Five of the cDNA sequences were homologous or identical to known genes (Table 1). SEQ ID NO:2 of gene 030 showed a 99% sequence identity with a portion of the 3' end of the cDNA for human maturation associated lymphocyte (MAL) protein, which is thought to be an integral membrane protein (Alonso et al., *Proc. Natl. Acad. Sci., U.S.A.*, 84:1997–2001, 1987) of unknown function. The human MAL protein gene mRNA is shown in Weissman et al., U.S. Pat. No. 4,835,255. The nucleotide sequence of the MAL cDNA and the deduced amino acid sequence of the MAL protein are shown in Alonso et al. (1987).

SEQ ID NO:6 of gene 056 showed a 99% sequence identity with a coding portion of a human calcium-activated potassium channel mRNA gene, hSlo, located on chromosome 10 (Pallanck et al., *Hum. Mol. Genet.*, 3:1239–1243, 1994), which is normally expressed by smooth muscle cells and hippocampal cells. The deduced amino acid sequence of hSlo is shown in Pallanck et al. (1994).

SEQ ID NO:8 of gene 082 showed a 67% sequence similarity with a portion of the human protocadherin 42 (pc42) gene, which is one of a family of protocadherins with characteristic extracellular cadherin motif repeats (Sano et al., *EMBO J.*, 12:2249–2256, 1993). Sano et al. shows the deduced amino acid sequences of human pc42 and pc43 aligned with the sequences of mouse M-cadherin and *Drosophila fat* gene. In the amino acid sequence encoded by gene 082 (SEQ ID NO:18), as shown in FIG. 2, there are at least three cadherin domains at about amino acid locations 111–121 (VKVGDTNDNPP, SEQ ID NO:24), about 215–226 (VQVADKNDNDP, SEQ ID NO:25), and about 318–328 (LFVMDENDNAP, SEQ ID NO:26). The 082 gene product shown in FIG. 2 also has a transmembrane domain at about amino acid locations 466–489 (LSIVIGVVAGIMTVILI-ILIVVMA, SEQ ID NO:27).

SEQ ID NO:8 of gene 082 also showed a similarity to a portion of the mouse muscle M-cadherin gene (Donalies et al., *Proc. Nat'l. Acad. Sci., USA*, 88:8024–8028, 1991). Donalies et al. compares the protein sequences of M-, N-, E-, and P-cadherins. Further, SEQ ID NO:8 of gene 082 showed a 98% identity to portions of two human cDNA clones, EST 165834 (GenBank Accession No. R86707) and EST 166286 (GenBank Accession No. R87599), which are both said to relate to a FAT-DROME P33450 Cadherin-related tumor suppresosr precursor.

Cadherins are involved in cellular differentiation, adherence, and intercellular communication (e.g., homotypic protein-protein interactions between the cadherin domains on cell-surface cadherins of different cells), and loss of cadherin function has been correlated with tumors and metastatic potential. Takeichi et al., *Curr. Opin. Cell Biol.*, 5:806–811 (1993). Protocadherins have some homology to cadherins in the extracellular domain and may also function as cell adhesion molecules.

A human "Multiple Tissue Northern" (MTN) Blot (Clontech, Palo Alto, Calif.; Catalog Nos. 7759-1 and 7760-1) analysis of gene 082 showed that this gene was expressed in various human tissues including spleen, prostate, testis, ovary, small intestine, colon mucosa, heart, brain, and muscle. Four separate mRNA transcripts of about 5.0, 6.5, 8.0, and 9.0 kilobases in length were detected.

SEQ ID NO:14 of gene 096 showed a very high sequence similarity (89%) to a portion of the 3' untranslated region of the bovine GTP-binding regulatory protein gamma-6 subunit mRNA (Robishaw et al., *J. Biol. Chem.*, 264:15758–15761, 1989). Robishaw et al. shows partial amino acid sequences of bovine brain G protein subunit gamma-6, nucleotide and amino acid sequences of bovine brain and adrenal G proteins, and predicted amino acid sequences of the gamma-6 subunit of bovine brain and retina G proteins. These different sequences show significant variability.

Finally, SEQ ID NO:15 of gene 097 showed a 99% sequence identity with a portion of a human mRNA which putatively encodes a translationally controlled tumor protein, by virtue of its homology to a murine gene, growth-related mouse tumor protein p23 (Gross et al., *Nucleic Acids Res.*, 17(20):8367, 1989). Northern analysis of SEQ ID NO:15 expression in normal human colon and human colon tumor samples showed a prominent band of about 1 kb, and a less intense band of about 1.3 kb in size.

Of the remaining cDNA sequences, one is homologous to an EST sequence, and eleven showed no homologies to any database sequences (Table 1). SEQ ID NO: 3 of gene 036 showed virtual sequence identity (96%) to the EST clone B4E07, which was isolated from a muscle cDNA library.

Northern analysis of other cDNA sequences showed that SEQ ID NO:1 of gene 029 hybridized to a message of 2.4 kb in normal colon total RNA. Northern analysis of expression of SEQ ID NO:16 of gene 101 showed strong expression in several message sizes between about 2.0 and 9.0 kb in skeletal muscle tissue. Messages were also present in heart, and weakly in placenta and pancreas. Analysis of expression of SEQ ID NO:12 of gene 093 showed a single message of about 4.4 kb in muscle tissue.

6. EXAMPLE

Use of Fingerprint Genes as Surrogate Markers in Clinical Trials

The expression pattern of the fingerprint genes of the invention can be used as surrogate markers to monitor clinical human trials of drugs being tested for their efficacy as tumor or cancer treatments, and can also be used to monitor patients undergoing clinical evaluation for the treatment of tumors and cancers. Either individual "fingerprint gene" expression patterns, or "fingerprint patterns," as defined above, can be analyzed.

The effect of the compound on the fingerprint gene expression normally displayed in connection with tumors and cancers, e.g., colon cancer, can be used to evaluate the efficacy of the compound as a treatment. Additionally, fingerprint gene expression can be used to monitor patients undergoing clinical evaluation for the treatment of tumors or cancers.

According to the invention, any fingerprint gene expression and fingerprint pattern derived from one of the paradigms described in Section 4.1.1. can be used to monitor clinical trials of drugs in human:patients. The paradigms described in Section 4.1.1., and illustrated in the Example of Section 5, for example, provide the fingerprint pattern of colon cancer and normal colon cells. This profile gives an indicative reading, therefore, of the cancerous and non-cancerous states of colon cells. Accordingly, the influence of anticancer chemotherapeutic agents on colon cancer cells can be measured by performing differential display on colon cells of patients undergoing clinical tests.

6.1. Treatment of Patients and Procurement of Tumor Cells or Biopsies

Compounds suspected of anti-tumor activity are administered to patients, whereas a placebo is administered to control patients. Tumor cells or biopsies are drawn from each patient after a determined period of treatment, e.g., 1 week, and RNA is isolated as described in Section 5.1., above.

6.2. Analysis of Samples

RNA is analyzed by Northern blots and RT-PCT. A decrease in colon cancer symptoms is indicated by an increase in the intensity of the bands corresponding to gene numbers 029, 030, 036, 038 (102), 056, 075, 082, 092, 095, 096 (105), or 101, as described in Section 5.2 above.

7. A NOVEL GENE EXPRESSED AT A HIGHER LEVEL IN NORMAL CELLS THAN IN TUMOR CELLS

As noted above, further cloning and sequence analysis demostrated that the gene 036 (SEQ ID NO: 3) and the gene 095 (SEQ ID NO: 13). Because gene 036 is a gene that is expressed at a higher level in normal cells than in tumor cells it may be a tumor suppressor gene. A human MTN Blot (Clontech, Palo Alto, Calif.; Catalog Nos. 7759-1 and 7760-1) analysis of gene 036 showed that this gene was expressed in various human tissues including heart, brain, placenta, lung, and muscle. Four separate mRNA transcripts of about 4.0, 5.5, 7.0, and 9.0 kilobases in length were detected. Northern analysis of expression of gene 036 in normal human colon and human colon tumor samples showed two messages of about 4.0 kb and about 7.0 kb in normal colon cells and in a few colon tumors.

Gene 036 encodes a protein having 740 amino acids. The nucleic acid sequence of a cDNA clone of gene 036 is shown in FIG. 7, along with the deduced amino acid sequence of the protein encoded by gene 036. As noted above, genes that are expressed at a higher level in normal cells than tumor cells are candidate tumor suppressor genes. Accordingly gene 036 and the protein it encodes can be used to interfere with the growth of tumors, particularly colon tumors. Various methods for using tumor suppressor genes are describe in U.S. Pat. Nos. 5,532,220; 5,527,676; and 5,552,283.

The gene 036 nucleic acid molecules of the invention can be cDNA, genomic DNA, synthetic DNA, or RNA, and can be double-stranded or single-stranded (i.e., either a sense or an antisense strand). Fragments of these molecules are also considered within the scope of the invention, and can be produced, for example, by the polymerase chain reaction (PCR) or generated by treatment with one or more restriction endonucleases. A ribonucleic acid (RNA) molecule can be produced by in vitro transcription. Preferably, the nucleic acid molecules encode polypeptides that, regardless of length, are soluble under normal physiological conditions.

The nucleic acid molecules of the invention can contain naturally occurring sequences, or sequences that differ from those that occur naturally, but, due to the degeneracy of the genetic code, encode the same polypeptide (for example, the polypeptide of SEQ ID NO:24). In addition, these nucleic acid molecules are not limited to sequences that only encode polypeptides, and thus, can include some or all of the non-coding sequences that lie upstream or downstream from a coding sequence.

The nucleic acid molecules of the invention can be synthesized (for example, by phosphoramidite-based synthesis) or obtained from a biological cell, such as the cell of a mammal. Thus, the nucleic acids can be those of a human, mouse, rat, guinea pig, cow, sheep, horse, pig, rabbit, monkey, dog, or cat. Combinations or modifications of the nucleotides within these types of nucleic acids are also encompassed.

In addition, the isolated nucleic acid molecules of the invention encompass fragments that are not found as such in the natural state. Thus, the invention encompasses recombinant molecules, such as those in which a nucleic acid molecule (for example, an isolated nucleic acid molecule encoding gene 036 protein) is incorporated into a vector (for example, a plasmid or viral vector) or into the genome of a heterologous cell (or the genome of a homologous cell, at a position other than the natural chromosomal location). Recombinant nucleic acid molecules and uses therefor are discussed further below.

In the event the nucleic acid molecules of the invention encode or act as antisense molecules, they can be used for example, to regulate translation of gene 036 mRNA. Techniques associated with detection or regulation of gene 036 expression are well known to skilled artisans and can be used to diagnose and/or treat inflammation or disorders associated with cellular proliferation.

The invention also encompasses nucleic acid molecules that hybridize under stringent conditions to a nucleic acid molecule encoding a gene 036 polypeptide. The gene 036 cDNA sequence described herein (SEQ ID NO:23) can be used to identify these nucleic acids, which include, for example, nucleic acids that encode homologous polypeptides in other species, and splice variants of the gene in humans or other mammals. Accordingly, the invention features methods of detecting and isolating these nucleic acid molecules. Using these methods, a sample (for example, a nucleic acid library, such as a cDNA or genomic library) is contacted (or "screened") with a gene 036-specific probe (for example, a fragment of SEQ ID NO:23 that is at least 12 nucleotides long). The probe will selectively hybridize to nucleic acids encoding related polypeptides (or to complementary sequences thereof). The probe, which can contain at least 12 (for example, 15, 25, 50, 100, or 200 nucleotides) can be produced using any of several standard methods (see, for example, Ausubel et al., "Current Protocols in Molecular Biology, Vol. I," Green Publishing Associates, Inc., and John Wiley & Sons, Inc., N.Y., 1989). For example, the probe can be generated using PCR amplification methods in which oligonucleotide primers are used to amplify a specific nucleic acid sequence that can be used as a probe to screen a nucleic acid library, as described in Example 1 below, and thereby detect nucleic acid molecules (within the library) that hybridize to the probe.

One single-stranded nucleic acid is said to hybridize to another if a duplex forms between them. This occurs when one nucleic acid contains a sequence that is the reverse and complement of the other (this same arrangement gives rise to the natural interaction between the sense and antisense strands of DNA in the genome and underlies the configuration of the "double helix"). Complete complementarity between the hybridizing regions is not required in order for a duplex to form; it is only necessary that the number of paired bases is sufficient to maintain the duplex under the hybridization conditions used.

Typically, hybridization conditions are of low to moderate stringency. These conditions favor specific interactions between completely complementary sequences, but allow some non-specific interaction between less than perfectly matched sequences to occur as well. After hybridization, the nucleic acids can be "washed" under moderate or high conditions of stringency to dissociate duplexes that are bound together by some non-specific interaction (the nucleic acids that form these duplexes are thus not completely complementary).

As is known in the art, the optimal conditions for washing are determined empirically, often by gradually increasing the stringency. The parameters that can be changed to affect stringency include, primarily, temperature and salt concentration. In general, the lower the salt concentration and the higher the temperature, the higher the stringency. Washing can be initiated at a low temperature (for example, room temperature) using a solution containing a salt concentration that is equivalent to or lower than that of the hybridization solution. Subsequent washing can be carried out using progressively warmer solutions having the same salt concentration. As alternatives, the salt concentration can be lowered and the temperature maintained in the washing step, or the salt concentration can be lowered and the temperature increased. Additional parameters can also be altered. For example, use of a destabilizing agent, such as formamide, alters the stringency conditions.

In reactions where nucleic acids are hybridized, the conditions used to achieve a given level of stringency will vary. There is not one set of conditions, for example, that will allow duplexes to form between all nucleic acids that are 85% identical to one another; hybridization also depends on unique features of each nucleic acid. The length of the sequence, the composition of the sequence (for example, the content of purine-like nucleotides versus the content of pyrimidine-like nucleotides) and the type of nucleic acid (for example, DNA or RNA) affect hybridization. An additional consideration is whether one of the nucleic acids is immobilized (for example, on a filter).

An example of a progression from lower to higher stringency conditions is the following, where the salt content is given as the relative abundance of SSC (a salt solution containing sodium chloride and sodium citrate; 2×SSC is 10-fold more concentrated than 0.2×SSC). Nucleic acids are hybridized at 42° C. in 2×SSC/0.1% SDS (sodium dodecylsulfate; a detergent) and then washed in 0.2×SSC/0.1% SDS at room temperature (for conditions of low stringency); 0.2×SSC/0.1% SDS at 42° C. (for conditions of moderate stringency); and 0.1×SSC at 68° C. (for conditions of high stringency). Washing can be carried out using only one of the conditions given, or each of the conditions can be used (for example, washing for 10–15 minutes each in the order listed above. Any or all of the washes can be repeated. As mentioned above, optimal conditions will vary and can be determined empirically.

A second set of conditions that are considered "stringent conditions" are those in which hybridization is carried out at 50° C. in Church buffer (7% SDS, 0.5% NaHPO$_4$, 1 M EDTA, 1% BSA) and washing is carried out at 50° C. in 2×SSC.

Once detected, the nucleic acid molecules can be isolated by any of a number of standard techniques (see, for example, Sambrook et al., "Molecular Cloning, A Laboratory Manual," 2nd Ed. Cold Spring Harbor Laboratory Press, Cold Spring Harbor, N.Y., 1989).

The invention also encompasses: (a) expression vectors that contain any gene 036 protein-related coding sequences and/or their complements (that is, "antisense" sequence); (b) expression vectors that contain any of the foregoing gene 036 protein-related coding sequences operatively associated with a regulatory element (examples of which are given below) that directs the expression of the coding sequences; (c) expression vectors containing, in addition to sequences encoding a gene 036 polypeptide, nucleic acid sequences that are unrelated to nucleic acid sequences encoding gene 036 polypeptide, such as molecules encoding a reporter or marker; and (d) genetically engineered host cells that contain any of the foregoing expression vectors and thereby express the nucleic acid molecules of the invention in the host cell.

Recombinant nucleic acid molecule can contain a sequence encoding a soluble gene 036 polypeptide, mature gene 036 polypeptide, or gene 036 polypeptide having a signal sequence. These polypeptides may be fused to additional polypeptides.

The regulatory elements referred to above include, but are not limited to, inducible and non-inducible promoters, enhancers, operators and other elements, which are known to those skilled in the art, and which drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage λ, the control regions of fd coat protein, the promoter for 3-phosphoglycerate kinase, the promoters of acid phosphatase, and the promoters of the yeast α-mating factors.

Similarly, the nucleic acid can form part of a hybrid gene encoding additional polypeptide sequences, for example, sequences that function as a marker or reporter. Examples of marker or reporter genes include β-lactamase, chloramphenicol acetyltransferase. (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter. Generally, the hybrid polypeptide will include a first portion and a second portion; the first portion being a gene 036 polypeptide and the second portion being, for example, the reporter described above or an immunoglobulin constant region.

The expression systems that may be used for purposes of the invention include, but are not limited to, microorganisms such as bacteria (for example, E. coli and B. subtilis) transformed with recombinant bacteriophage DNA, plasmid DNA, or cosmid DNA expression vectors containing the nucleic acid molecules of the invention; yeast (for example, Saccharomyces and Pichia) transformed with recombinant yeast expression vectors containing the nucleic acid molecules of the invention (e.g., SEQ ID NO:23); insect cell systems infected with recombinant virus expression vectors (for example, baculovirus) containing the nucleic acid molecules of the invention; plant cell systems infected with recombinant virus expression vectors (for example, cauliflower mosaic virus (CaMV) and tobacco mosaic virus (TMV)) or transformed with recombinant plasmid expression vectors (for example, Ti plasmid). containing gene 036 nucleotide sequences; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter).

In bacterial systems, a number of expression vectors may be advantageously selected depending upon the use intended for the gene product being expressed. For example, when a large quantity of such a protein is to be produced, for the generation of pharmaceutical compositions containing gene 036 polypeptides or for raising antibodies to those polypeptides, vectors that are capable of directing the expression of high levels of fusion protein products that are readily purified may be desirable. Such vectors include, but are not limited to, the E. coli expression vector pUR278 (Ruther et al., EMBO J. 2:1791, 1983), in which the coding sequence of the insert may be ligated individually into the vector in frame with the lacZ coding region so that a fusion protein is produced; pIN vectors (Inouye and Inouye, Nucleic Acids Res. 13:3101–3109, 1985; Van Heeke and Schuster, J. Biol. Chem. 264:5503–5509, 1989); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhidrosis virus (AcNPV) can be used as a vector to express foreign genes. The virus grows in Spodoptera frugiperda cells. The coding sequence of the insert may be cloned individually into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (for example, see Smith et al., J. Virol. 46:584, 1983; Smith, U.S. Pat. No. 4,215,051),.

In mammalian host cells, a number of viral-based expression systems may be utilized. In cases where an adenovirus is used as an expression vector, the nucleic acid molecule of the invention may be ligated to an adenovirus transcription/translation control complex, for example, the late promoter and tripartite leader sequence. This chimeric gene may then be inserted in the adenovirus genome by in vitro or in vivo recombination. Insertion in a non-essential region of the viral genome (for example, region E1 or E3) will result in a recombinant virus that is viable and capable of expressing a gene 036 gene product in infected hosts (for example, see Logan and Shenk, Proc. Natl. Acad. Sci. USA 81:3655–3659, 1984). Specific initiation signals may also be required for efficient translation of inserted nucleic acid molecules. These signals include the ATG initiation codon and adjacent sequences. In cases where an entire gene or cDNA, including its own initiation codon and adjacent sequences, is inserted into the appropriate expression vector, no additional translational control signals may be needed. However, in cases where only a portion of the coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:516–544, 1987).

In addition, a host cell strain may be chosen which modulates the expression of the inserted sequences, or modifies and processes the gene product in the specific fashion desired. Such modifications (for example, glycosylation) and processing (for example, cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. The mammalian cell types listed above are among those that could serve as suitable host cells.

For long-term, high-yield production of recombinant proteins, stable expression is preferred. For example, cell lines which stably express the gene 036 protein and polypeptide sequences described above may be engineered. Rather than using expression vectors which contain viral origins of replication, host cells can be transformed with DNA controlled by appropriate expression control elements (for example, promoter, enhancer sequences, transcription terminators, polyadenylation sites, etc.), and a selectable marker. Following the introduction of the foreign DNA, engineered cells may be allowed to grow for 1–2 days in an enriched media, and then switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express gene 036 protein. Such engineered cell lines may be particularly useful in screening and evaluation of compounds that affect the endogenous activity of the gene product.

A number of selection systems can be used. For example, the herpes simplex virus thymidine kinase (Wigler, et al., *Cell* 11:223, 1977), hypoxanthine-guanine phosphoribosyltransferase (Szybalska and Szybalski, *Proc. Natl. Acad. Sci. USA* 48:2026, 1962), and adenine phosphoribosyltransferase (Lowy, et al., *Cell* 22:817, 1980) genes can be employed in tk⁻, hgprt⁻ or aprt⁻ cells, respectively. Also, anti-metabolite resistance can be used as the basis of selection for the following genes: dhfr, which confers resistance to methotrexate (Wigler et al., *Proc. Natl. Acad. Sci. USA* 77:3567, 1980; O'Hare et al., *Proc. Natl. Acad. Sci. USA* 78:1527, 1981); gpt, which confers resistance to mycophenolic acid (Mulligan and Berg, *Proc. Natl. Acad. Sci. USA* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al., *Gene* 30:147, 1984).

Alternatively, any fusion protein may be readily purified by utilizing an antibody specific for the fusion protein being expressed. For example, a system described by Janknecht et al. allows for the ready purification of non-denatured fusion proteins expressed in human cell lines (*Proc. Natl. Acad. Sci. USA* 88: 8972–8976, 1991). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$·nitriloacetic acid-agarose columns and histidine-tagged proteins are selectively eluted with imidazole-containing buffers.

Gene 036 Polypeptides

The gene 036 polypeptides described herein are those encoded by any of the nucleic acid molecules described above and include gene 036 protein fragments, mutants, truncated forms, and fusion proteins. These polypeptides can be prepared for a variety of uses, including but not limited to the generation of antibodies, as reagents in diagnostic assays, for the identification of other cellular gene products or compounds that can modulate expression or activity of gene 036 protein.

The invention also encompasses polypeptides that are functionally equivalent to gene 036 protein. These polypeptides are equivalent to gene 036 protein in that they are capable of carrying out one or more of the functions of gene 036 protein in a biological system. Preferred gene 036 polypeptides have 20%, 40%, 50%, 75%, 80%, or even 90% of the activity of the full-length, mature human form of gene 036 protein described herein. Such comparisons are generally based on an assay of biological activity in which equal concentrations of the polypeptides are used and compared. The comparison can also be based on the amount of the polypeptide required to reach 50% of the maximal stimulation obtainable.

Functionally equivalent proteins can be those, for example, that contain additional or substituted amino acid residues. Substitutions may be made on the basis of similarity in polarity, charge, solubility, hydrophobicity, hydrophilicity, and/or the amphipiathic nature of the residues involved. Amino acids that are typically considered to provide a conservative substitution for one another are specified in the summary of the invention.

Polypeptides that are functionally equivalent to gene 036 protein (SEQ ID NO:2) can be made using random mutagenesis techniques well known to those skilled in the art (and the resulting mutant gene 036 proteins can be tested for activity). It is more likely, however, that such polypeptides will be generated by site-directed mutagenesis (again using techniques well known to those skilled in the art). These polypeptides may have an increased function, i.e., a greater ability to inhibit cellular proliferation, or to evoke an inflammatory response. Such polypeptides can be used to protect progenitor cells from the effects of chemotherapy and/or radiation therapy.

To design functionally equivalent polypeptides, it is useful to distinguish between conserved positions and variable positions. This can be done by aligning the sequence of gene 036 cDNAs that were obtained from various organisms. Skilled artisans will recognize that conserved amino acid residues are more likely to be necessary for preservation of function. Thus, it is preferable that conserved residues are not altered.

Mutations within the gene 036 protein coding sequence can be made to generate gene 036 proteins that are better suited for expression in a selected host cell. For example, N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur (in N—X—S or N—X—), and/or an amino acid deletion at the second position of any one or more of such recognition sequences, will prevent glycosylation at the modified tripeptide sequence (see, for example, Miyajima et al., *EMBO J.* 5:1193, 1986).

The polypeptides of the invention can be expressed fused to another polypeptide, for example, a marker polypeptide or fusion partner. For example, the polypeptide can be fused to a hexa-histidine tag to facilitate purification of bacterially expressed protein or a hemagglutinin tag to facilitate purification of protein expressed in eukaryotic cells. The gene 036 polypeptides of the invention, or a portion thereof, can also be altered so that it has a longer circulating half-life by fusion to an immunoglobulin Fc domain (Capon et al., *Nature* 337:525–531, 1989). Similarly, a dimeric form of the gene 036 protein polypeptide can be produced, which has increased stability in vivo.

The polypeptides of the invention can be chemically synthesized (for example, see Creighton, "Proteins: Structures and Molecular Principles," W.H. Freeman & Co., N.Y., 1983), or, perhaps more advantageously, produced by recombinant DNA technology as described herein. For additional guidance, skilled artisans may consult Ausubel et al. (supra), Sambrook et al. ("Molecular Cloning, A Laboratory Manual," Cold Spring Harbor Press, Cold Spring Harbor, N.Y., 1989), and, particularly for examples of chemical synthesis Gait, M. J. Ed. ("Oligonucleotide Synthesis," IRL Press, Oxford, 198.4).

The invention-also features polypeptides that interact with gene 036 protein (and the genes that encode them) and thereby alter the function of gene 036 protein. Interacting polypeptides can be identified using methods known to those skilled in the art. One suitable method is the "two-hybrid system," which detects protein interactions in vivo (Chien et al., *Proc. Natl. Acad. Sci. USA*, 88:9578, 1991). A kit for practicing this method is available from Clontech (Palo Alto, Calif.).

Gene 036 and the protein encoded by gene 036, can be used in any of the applications described herein. In addition, portions of the 036 gene, e.g., the portion described on identified as SEQ ID NO: 3 or the portion identified as SEQ ID NO: 13, can be used in any of the applications described herein.

Gene 036 and the protein encoded by gene 036 can be used in screening assays to identify compounds that alter the expression or activity of the protein encoded by gene 036. In such screening assays the level of expression or activity is measured in the presence and absence of a selected compound. These two measurements are then compared to determine whether the selected compound alters expression or activity. Similar assays can be used to compare the effect of a selected compound on expression or activity to the effect of a compound known to alter expression or activity.

Compounds which alter the expression of the gene 036 protein can be used therapeutically for treatment of disorders associated with aberrant expression of gene 036.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule consisting of the nucleotide sequence of SEQ ID NO:3.

2. An isolated nucleic acid molecule consisting of the nucleotide sequence of SEQ ID NO:13.

3. An isolated nucleic acid molecule consisting of the nucleotide sequence of SEQ ID NO:23.

4. An isolated nucleic acid molecule consisting of the nucleotide sequence of SEQ ID NO:3 and at least one flanking heterologous nucleotide sequence.

5. An isolated nucleic acid molecule consisting of the nucleotide sequence of SEQ ID NO:13 and at least one flanking heterologous nucleotide sequence.

6. An isolated nucleic acid molecule comprising the nucleotide sequence of SEQ ID NO:23.

7. An isolated nucleic acid molecule consisting of a fragment of the isolated nucleic acid molecule of claim 3 wherein the fragment comprises the nucleotide sequence of SEQ ID NO:3.

8. An isolated nucleic acid molecule consisting of a fragment of the isolated nucleic acid molecule of claim 3 wherein the fragment comprises the nucleotide sequence of SEQ ID NO:13.

9. An isolated nucleic acid molecule consisting of a fragment of the isolated nucleic acid molecule of claim 3 and at least one flanking heterologous nucleotide sequence wherein the fragment comprises the nucleotide sequence of SEQ ID NO:3.

10. An isolated nucleic acid molecule consisting of a fragment of the nucleic acid molecule of claim 3 and at least one flanking heterologous nucleotide sequence wherein the fragment comprises the nucleotide sequence of SEQ ID NO:13.

11. An isolated nucleic acid probe which hybridizes along its entire length to a nucleici acid molecule consisting of the nucleotide sequence of SEQ ID NO:3 under conditions of hybridization in 0.5 M $NaHPO_4$/7% SDS/1 mM EDTA at 65° C. followed by washing in 0.1×SSC/0.1% SDS at 68° C., the isolated nucleic acid probe comprising at least 100 nucleotides.

12. An isolated nucleic acid probe which hybridizes along its entire length to a nucleic acid molecule consisting of the nucleotide sequence of SEQ ID NO:13 under conditions of hybridization in 0.5 M $NaHPO_4$/7% SDS/1 mM EDTA at 65° C. followed by washing in 0.1×SSC/0.1% SDS at 68° C., the isolated nucleic acid probe comprising at least 100 nucleotides.

13. An isolated nucleic acid probe which hybridizes along its entire length to a nucleic acid molecule consisting of the nucleotide sequence of SEQ ID NO:23 under conditions of hybridization in 0.5 M $NaHPO_4$/7% SDS/1 mM EDTA at 65° C. followed by washing in 0.1×SSC/0.1% SDS at 68° C., the isolated nucleic acid probe comprising at least 100 nucleotides.

14. An isolated nucleic acid molecule which hybridizes along its entire length to a nucleic acid molecule consisting of the nucleotide sequence of SEQ ID NO:23 under conditions of hybridization in 0.5 M $NaHPO_4$/7% SDS/1 mM EDTA at 65° C. followed by washing in 0.1×SSC/0.1% SDS at 68° C., the isolated nucleic acid molecule comprising at least 100 nucleotides.

15. An isolated nucleic acid molecule consisting of a fragment of a nucleic acid molecule consisting of the nucleotide sequence of SEQ ID NO:3, the fragment comprising at least 100 contiguous nucleotides of the nucleotide sequence of SEQ ID NO:3.

16. An isolated nucleic acid molecule consisting of a fragment of a nucleic acid molecule consisting of the nucleotide sequence of SEQ ID NO:13, the fragment comprising at least 100 contiguous nucleotides of the nucleotide sequence of SEQ ID NO:13.

17. An isolated nucleic acid molecule consisting of a fragment of a nucleic acid molecule consisting of the nucleotide sequence of SEQ ID NO:23, the fragment comprising at least 100 contiguous nucleotides of the nucteotide sequence of SEQ ID NO:23.

18. An isolated nucleic acid molecule consisting of: (a) a fragment of a nucleic acid molecule consisting of the nucleotide sequence of SEQ ID NO:3, the fragment comprising at least 100 contiguous nucleotides of the nucleotide sequence of SEQ ID NO:3 and (b) at least one flanking heterologous nucleotide sequence.

19. An isolated nucleic acid molecule consisting of: (a) a fragment of a nucleic acid molecule consisting of the nucleotide sequence of SEQ ID NO:13, the fragment comprising at least 100 contiguous nucleotides of the nucleotide sequence of SEQ ID NO:13 and (b) at least one flanking heterologous nucleotide sequence.

20. An isolated nucleic acid molecule consisting of: (a) a fragment of a nucleic acid molecule consisting of the nucleotide sequence of SEQ ID NO:3, the fragment comprising at least 100 contiguous nucleotides of the nucleotide sequence of SEQ ID NO:23 and (b) at least one flanking heterologous nucleotide sequence.

21. A host cell genetically engineered to contain the isolated nucleic acid molecule of any of claims 1–20.

22. A nucleic acid vector comprising the nucleic acid molecule of any of claims 1–20.

23. The nucleic acid vector of claim 22, further comprising a regulatory element.

24. The vector of claim 23, wherein the regulatory element is selected from the group consisting of the cytomegalovirus hCMV immediate early gene, the early promoter of SV40 adenovirus, the late promoter of SV40 adenovirus, the lac system, the trp system, the TAC system, the TRC system, the major operator and promoter regions of phage λ, the control regions of fd coat protein, the promoter for 3-phosphoglycerate kinase, the promoters of acid phosphatase, and the promoters of the yeast α-mating factors.

25. The vector of claim 22, wherein the vector is a plasmid.

26. The vector of claim 22, wherein the vector is a virus.

27. The vector of claim 26, wherein the virus is a retrovirus.

* * * * *